United States Patent
Deng et al.

(10) Patent No.: US 11,873,523 B2
(45) Date of Patent: Jan. 16, 2024

(54) **ACONITIC ACID EXPORTER (AEXA) INCREASES ORGANIC ACID PRODUCTION IN *ASPERGILLUS***

(71) Applicant: Battelle Memorial Institute, Richland, WA (US)

(72) Inventors: Shuang Deng, Richland, WA (US); Jon K. Magnuson, Richland, WA (US); Joonhoon Kim, Berkeley, CA (US); Kyle R. Pomraning, Richland, WA (US); Ziyu Dai, Richland, WA (US); Beth A. Hofstad, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 17/347,109

(22) Filed: Jun. 14, 2021

(65) Prior Publication Data
US 2021/0388399 A1  Dec. 16, 2021

Related U.S. Application Data

(60) Provisional application No. 63/039,241, filed on Jun. 15, 2020.

(51) Int. Cl.
| | |
|---|---|
| C12P 7/46 | (2006.01) |
| C12N 1/14 | (2006.01) |
| C12R 1/69 | (2006.01) |

(52) U.S. Cl.
CPC ............. *C12P 7/46* (2013.01); *C12N 1/145* (2021.05); *C12R 2001/69* (2021.05)

(58) Field of Classification Search
CPC ............ C12P 7/46; C12N 1/145; C12N 9/88; C12N 15/52; C12R 2001/69; C12R 2001/66; C12Y 401/01006; C07K 14/38
See application file for complete search history.

(56) References Cited

U.S. PATENT DOCUMENTS

| | | |
|---|---|---|
| 4,123,459 A | 10/1978 | Gutierrez et al. |
| 4,740,464 A | 4/1988 | Holdom et al. |

(Continued)

FOREIGN PATENT DOCUMENTS

| | | |
|---|---|---|
| CN | 110527637 A | 12/2019 |
| WO | WO 2018/213349 A1 | 11/2018 |

OTHER PUBLICATIONS

Quistgaard, E., Löw, C., Guettou, F. et al. Understanding transport by the major facilitator superfamily (MFS): structures pave the way. Nat Rev Mol Cell Biol 17, 123-132 (2016). https://doi.org/10.1038/nrm.2015.25 (Year: 2016).*

(Continued)

*Primary Examiner* — Lora E Barnhart Driscoll
*Assistant Examiner* — Candice Lee Swift
(74) *Attorney, Agent, or Firm* — KLARQUIST SPARKMAN, LLP

(57) ABSTRACT

Recombinant *Aspergillus* genetically modified to increase expression of g8846, renamed herein as aconitic acid exporter (aexA), are provided, which in some examples are also genetically inactivated for an endogenous cis-aconitic acid decarboxylase (cadA) gene. Such recombinant *Aspergillus* produce more aconitic acid as compared to native *Aspergillus*. Also provided are methods of using such recombinant *Aspergillus* to increase production of aconitic acid and other organic acids, such as citric acid, itaconic acid, and 3-hydroxypropionic acid (3-HP).

25 Claims, 6 Drawing Sheets
(3 of 6 Drawing Sheet(s) Filed in Color)
Specification includes a Sequence Listing.

(56) References Cited

U.S. PATENT DOCUMENTS

| | | |
|---|---|---|
| 10,947,548 B2 | 3/2021 | Deng et al. |
| 2008/0199926 A1 | 8/2008 | Burgard et al. |
| 2015/0267228 A1 | 9/2015 | Borodina et al. |
| 2021/0163966 A1 | 6/2021 | Deng et al. |

OTHER PUBLICATIONS

Clustal Omega; https://www.ebi.ac.uk/Tools/msa/clustalo/; accessed Jul. 18, 2023 (Year: 2022).*

Tao, L., "Engineering the Production of Itaconic Acid in *Escherichia coli*," Dissertation, Rice University, 2011 (75 pages).

Bruce, W.F, in Organic Syntheses (Ed.: H. A. Blatt), John Wiley and Sons, Inc., New York, 1943, pp. 12-14.

Cao et al., "A novel hyperbranched polyester made from aconitic acid (B3) and di(ethylene glycol) (A2)," *Polym Int.* 60:630-634, 2011.

Deng et al., "Deletion analysis of the itaconic acid biosynthesis gene cluster components in Aspergillus pseudoterreus ATCC32359," *Appl Microbiol Biotechnol.* 104:3981-3992, 2020.

Deng et al., "Deletion Analysis of the Itaconic Acid Production Gene Cluster Components in *Aspergillus pseudoterreus ATCC32359*," Poster presented at 40th Symposium on Biotechnology for Fuels and Chemicals, Apr. 29-May 2, 2018, Clearwater, Florida.

GenBank Database Accession No. AB326105, Aug. 2008 (2 pages).

Kobayashi et al., "Bioproduction of trans-Aconitic Acid from Citric Acid by Whole-Cell Reaction of *Escherichia coli* Heterologously Expressing the Aconitate Isomerase Gene from *Pseudomonas* sp. WU-0701," *ChemistrySelect* 1:1467-1471, 2016.

Kumar and Raveendiran, "Synthesis, Characterisation, Biological and Molecular Docking Studies of Aconitic Acid Based Co-Polyester," *Asian J Research Chem.* 11:723-730, 2018.

Li et al., "A clone-based transcriptomics approach for the identification of genes relevant for itaconic acid production in Aspergillus," *Fungal Genet Biol.* 48:602-611, 2011.

Nielsen, J., "Metabolic Engineering," *Appl Microbial Biotechnol.* 55:263-283, 2001.

Rodrigues et al., "Exploring the Brazilian diversity of *Aspergillus* sp. strains for lovastatin and itaconic acid production," *Fungal Genet Biol.* 138:103367, 2020 (11 pages).

Samson et al., "New species in *Aspergillus* section *terrei*," *Stud Mycol.* 69:39-55, 2011.

Samson et al., "Phylogeny, identification and nomenclature of the genus *Aspergillus*," *Stud Mycol.* 78:141-173, 2014.

Steiger et al., "Biochemistry of microbial 1tacon1c acid production," *Frontiers Microbial.* 4:23, 2013 (5 pages).

UniProt Database Accession No. B3IUN8, Oct. 2017 (2 pages).

Van der Straat et al., "Expression of the *Aspergillus terreus* itaconic acid biosynthesis cluster in *Aspergillus niger*," Microb. Cell Fae. 13:11, 2014 (9 pages).

* cited by examiner

FIG. 5

ACONITIC ACID EXPORTER (AEXA) INCREASES ORGANIC ACID PRODUCTION IN *ASPERGILLUS*

CROSS REFERENCE TO RELATED APPLICATION

This application claims priority to U.S. Provisional Application No. 63/039,241 filed Jun. 15, 2020, herein incorporated by reference in its entirety.

ACKNOWLEDGMENT OF GOVERNMENT SUPPORT

This disclosure was made with Government support under Contract DE-AC05-76RL0 1830 awarded by the U.S. Department of Energy. The Government has certain rights in the invention.

FIELD

Recombinant *Aspergillus* genetically modified to increase expression of aconitic acid exporter (aexA) are provided, which in some examples are also genetically inactivated for an endogenous cis-aconitic acid decarboxylase (cadA) gene. Also provided are methods of using such recombinant *Aspergillus* to increase production of aconitic acid and other organic acid products such as citric acid, itaconic acid, and 3-hydroxypropionic acid (3-HP).

BACKGROUND

Aconitic acid (AA) is one of the top 30 potential building block candidates (Werpy and Petersen 2004). It is a 6-carbon unsaturated tricarboxylic acid and there are two isomer, cis- and trans-. In nature, it can be extracted from plants such as sugar cane, beet root and sorghum. It is used as artificial flavor in the food industry. It can also be used as plasticizer to increase flexibility in making polymer. Trans-AA can be used to make polymers (Cao et al. 2011), especially the biomaterials in biomedical field (Kumar and Raveendiran 2018).

However, industrial processes proposed for aconitic acid synthesis give low yields, require energy intensive high temperatures, utilize harmful reagents and generate hazardous byproducts (Gutierrez; Eddie N. 1978), which is not a sustainable approach. Recently, the first bio-based trans-AA was produced by metabolic engineering aconitase isomerase from *Pseudomonas* sp. WU-0701 into *E. coli* (Kobayashi 2016). However, the substrate for the recombinant *E. coli* to produce trans-AA is citric acid, which has to be first generated from other fermentation processes.

Previously, a fungal platform was produced for the production of AA from lingocellulosic biomass by deleting cis-aconitate decarboxylase (cadA) gene in *Aspergillus pseudoterreus* (Deng et al. 2020). *Aspergillus pseudoterreus* naturally produces large amount of itaconic acid (see FIGS. 4A-4C). cis aconitic acid is converted to itaconic acid with the presence of cadA. By deleting the cadA gene, the new strain no longer produced itaconic acid, instead producing AA at about 10 g/L at day 7 (see FIG. 4A). However, compared with wild type, AA yield is only ⅕ of itaconic acid (see FIGS. 4A-4C).

SUMMARY

Using comparative proteomics analysis of an *Aspergillus pseudoterreus* cadA wild type strain vs an *Aspergillus pseudoterreus* cadA mutant strain, a specific aconitic acid exporter (aexA, g8846 gene in *Aspergillus pseudoterreus*) was identified. It is shown herein that overexpression of aexA in *Aspergillus* results in high production of aconitic acid.

Based on this discovery, provided herein are isolated recombinant *Aspergillus* fungi having at least one exogenous nucleic acid molecule that encodes aconitic acid exporter (aexA) operably linked to an exogenous promoter (such as a strong promoter), thereby overexpressing the aexA in the *Aspergillus*. The sequence encoding aexA (as well as the aexA protein produced) may be native to the particular strain or species of *Aspergillus*, but it is operably linked to a non-native promoter, making the resulting construct (which may be a vector) non-native to the recombinant *Aspergillus*. The recombinant *Aspergillus* can further include other genetic modifications, such as a genetically inactivated endogenous cis-aconitic acid decarboxylase (cadA) gene. In some examples, the recombinant *Aspergillus* furthers includes one or more additional exogenous nucleic acid molecules that encode proteins that allow the *Aspergillus* to produce other products. For example, the recombinant *Aspergillus* can include exogenous nucleic acid molecules encoding aspartate 1-decarboxylase (panD), a β-alanine-pyruvate aminotransferase (BAPAT), and 3-hydroxypropionate dehydrogenase (3-HPDH), thereby permitting the *Aspergillus* to produce 3-HP.

Also provided are isolated nucleic acid molecules encoding an aexA protein operably linked to a heterologous promoter. Such isolated nucleic acid molecules can be part of a vector, such as a plasmid.

Compositions that include one or more disclosed recombinant *Aspergillus* are provided, as are compositions that include one or more disclosed isolated nucleic acid molecules encoding an aexA protein operably linked to a heterologous promoter. In some examples the compositions include other materials, such as a growth media or a pharmaceutically acceptable carrier, such as water or saline.

Kits are also provided that include one or more disclosed recombinant *Aspergillus* and a growth media for culturing or growing the *Aspergillus*. In some examples the *Aspergillus* is in a container, such as a glass or plastic vial, which may also include growth media. Kits are also provided that include disclosed isolated nucleic acid molecules encoding an aexA protein operably linked to a heterologous promoter. In some examples, a kit also includes one or more reagents to allow transformation of *Aspergillus*, such as protoplast isolation buffer, osmotic wash buffer, polyethylene glycol, filtration material (such as miracloth), antibiotic (e.g., hygromicin), or combinations thereof.

Also provided are methods of making AA. Such methods can include culturing a recombinant *Aspergillus* fungus provided herein that overexpresses aexA (and in some examples also has a genetically inactivated endogenous cadA gene) under conditions that permit the fungus to make AA, thereby producing AA. Similar methods can be used to produce citric acid and itaconic acid. Also provided are methods of making 3-hydroxypropionic acid (3-HP). Such methods can include culturing a recombinant *Aspergillus* fungus provided herein that overexpresses aexA (and in some examples also has a genetically inactivated endogenous cadA gene), along with panD, BAPAT, and 3-HPDH, under conditions that permit the fungus to produce 3-HP, thereby making 3-HP.

The foregoing and other objects and features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 5:
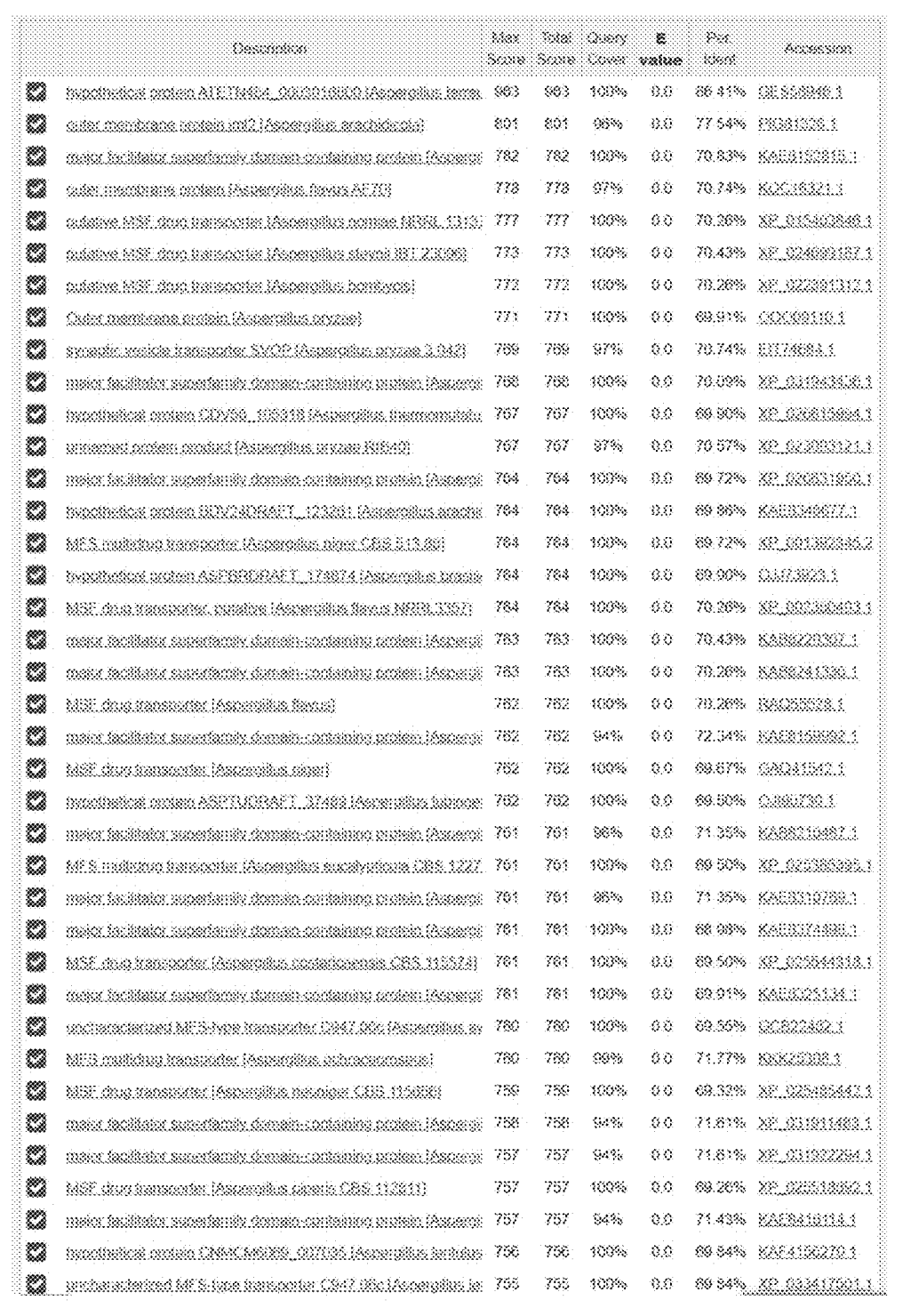

FIG. 5 shows the results of the blastp program to identify homologs of SEQ ID NO: 2. Thus, the GenBank accession nos. provided disclosed aexA sequences that can be overexpressed in *Aspergillus*, for example in combination endogenous cad deleted (Δcad).

SEQUENCE LISTING

Figure 1:
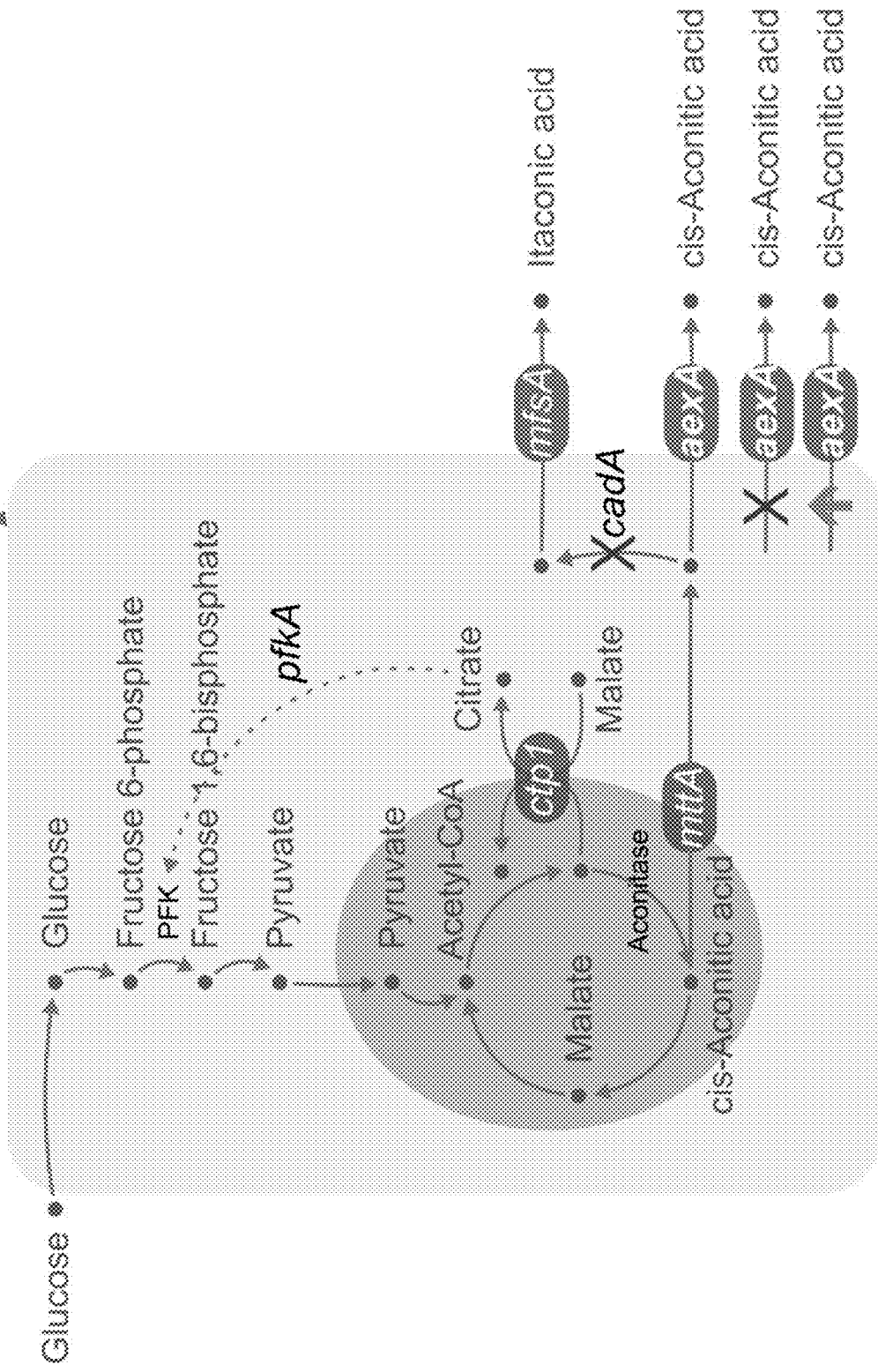
FIG. 1 is a schematic drawing of the aconitic acid biosynthetic and transport pathway. Aconitic acid and itaconic acid share the same biosynthesis pathway, but use different transporters to export outside the cell. Itaconic acid is secreted through mfsA transporter. Deletion of cadA results in accumulation of aconitic acid, which is secreted from the cell via a specific aexA transporter.

The nucleic acid sequences listed in the accompanying sequence listing are shown using standard abbreviations for nucleotide bases and amino acids, as defined in 37 C.F.R. 1.822. Only one strand of each nucleic acid sequence is shown, but the complementary strand is understood as included by any reference to the displayed strand. The sequence listing submitted herewith, generated on Jul. 2, 2021, 52.4 kb, is herein incorporated by reference. In the accompanying sequence listing:

SEQ ID NOS: 1-2 are exemplary aexA coding and protein sequences, respectively, from *A. pseudoterreus*.

SEQ ID NO: 3 is an exemplary aexA protein sequence from *A. terreus* (GenBank® Accession No. GES58946.1). Corresponding coding sequence GenBank Accession No. BKZM02000003.1:443944.445205

SEQ ID NO: 4 is an exemplary aexA protein sequence from *A. arachidicola* (GenBank Accession No. PIG81326.1). Corresponding coding sequence GenBank Accession No. join (NEXV01000567.1:39009.39417, NEXV01000567.1:39519.39862, NEXV01000567.1:39922.40253, NEXV01000567.1:40314.40405, NEXV01000567.1:40461.40482, NEXV01000567.1:40546.40889, NEXV01000567.1:41917.42713, NEXV01000567.1:42769.43772, NEXV01000567.1:43830.43896, NEXV01000567.1:43997.44073, NEXV01000567.1:44145.44162, NEXV01000567.1:44241.44331)

SEQ ID NO: 5 is an exemplary g8846 (aexA) protein sequence from *A. avenaceus* (GenBank Accession No. KAE8152815.1). Corresponding coding sequence GenBank Accession No. join (ML742047.1:79398.80261, ML742047.1:80313.80644, ML742047.1:80695.80786, ML742047.1:80840.80861, ML742047.1:80918.81275

SEQ ID NOS: 6 and 7 are exemplary cadA nucleic acid and protein sequences, respectively, from *A. terreus* (GenBank Accession Nos. AB326105.1 and BAG49047.1).

SEQ ID NOS: 8 and 9 are exemplary cadA nucleic acid and protein sequences, respectively, from *A. vadensis* CBS 113365 (GenBank® Accession Nos. XM_025706777.1 and XP_025563141.1).

SEQ ID NO: 10 is an *A. pseudoterreus* 5'-cadA nucleic acid sequence.

SEQ ID NO: 11 is an *A. pseudoterreus* 3'-cadA gene.

SEQ ID NOS: 12 and 13 are exemplary aspartate 1-decarboxylase (panD) nucleic acid and protein sequences, respectively, from *Tribolium castaneum* (GenBank® Accession Nos. NM_001102585.1 and NP_001096055.1). Coding sequence nt 41-1663.

SEQ ID NO: 14 is panD cDNA of *Tribolium castaneum* with codon optimization for *A. pseudoterreus*.

SEQ ID NOS: 15 and 16 are exemplary β-alanine-pyruvate aminotransferase (BAPAT) nucleic acid and protein sequences, respectively, from *Bacillus cereus* AH1272 (GenBank® Accession Nos. ACMS01000158.1 (complement (10606.11961)) and EEL86940.1).

SEQ ID NO: 17 is BAPAT codon optimized synthetic cDNA for *A. pseudoterreus* from *Bacillus cereus*.

SEQ ID NOS: 18 and 19 are exemplary 3-hydroxypropionate dehydrogenase (3-HPDH) nucleic acid and protein sequences (GenBank® Accession No. WP_000636571), respectively.

SEQ ID NO: 20 is the 3-HPDH codon optimized synthetic cDNA for *A. pseudoterreus* from *E. coli*.

SEQ ID NO: 21 is a vector that can be used to overexpresses aexA. nt 1-2951 pBSK vector backbone; nt 2952-3932 gpdA promoter from *Aspergillus nidulans*; nt 3933-5678 aconitic acid exporter aexA coding sequence; nt 5679-6465 TrpC terminator from *A. nidulans*., and nt 6466-8478 pyrithiamine selection marker (ptrA) selection marker from *A. oryzae*.

SEQ ID NOS: 22-29 are primers that can be used to delete an endogenous cadA gene in *A. pseudoterreus*.

SEQ ID NO: 30 is an *A. niger* gpdA promoter nucleic acid sequence.

SEQ ID NO: 31 is a bidirectional terminator from *A. niger* elf3/multifunctional chaperone.

SEQ ID NO: 32 is an *A. niger* enol promoter.

SEQ ID NO: 33 is an *A. nidulans* gpdA promoter.

SEQ ID NOS: 34-39 are primers used to delete endogenous mfsA from *A. pseudoterreus*.

SEQ ID NOS: 40-45 are primers used to delete endogenous g2022 from *A. pseudoterreus*.

SEQ ID NOS: 46-51 are primers used to delete endogenous g2739 from *A. pseudoterreus*.

SEQ ID NOS: 52-57 are primers used to delete endogenous g2945 from *A. pseudoterreus*.

SEQ ID NOS: 58-64 are primers used to delete endogenous g8846 (aexA) from *A. pseudoterreus*.

SEQ ID NOS: 65-69 are primers used to delete endogenous g9513 from *A. pseudoterreus*.

SEQ ID NOS: 70-75 are primers used to delete endogenous g9885 from *A. pseudoterreus*.

SEQ ID NOS: 76-81 are primers used to delete endogenous g9935 from *A. pseudoterreus*.

SEQ ID NOS: 82-89 are primers used to overexpress g8846 (aexA) from gpdA promoter in *A. pseudoterreus*.

DETAILED DESCRIPTION

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, references and Genbank® Accession numbers (the sequence available on Jun. 15, 2020) mentioned herein are incorporated by reference in their entireties. The materials, methods, and examples are illustrative only and not intended to be limiting.

In order to facilitate review of the various embodiments of the disclosure, the following explanations of specific terms are provided:

3-hydroxypropionate dehydrogenase (3-HPDH): EC 1.1.1.59 An enzyme that catalyzes the chemical reaction: 3-hydroxypropanoate+NAD±⇌3-oxopropanoate+NADH+ $H^+$. The term 3-HPDH includes any 3-HPDH gene (such as a bacterial or fungal panD sequence), cDNA, mRNA, or protein, which is a 3-HPDH that can covert 3-hydroxypropanoate and NAD into 3-oxopropanoate, NADH, and $H^+$ and vice versa. Expression or increased expression of 3-HPDH, for example in an *Aspergillus* also expressing BAPAT and panD and overexpressing aexA (e.g., from an exogenous nucleic acid molecule), and in some examples also having a genetically inactivated cadA gene (ΔcadA), results in a fungus that has an ability to produce more 3-HP than the parent strain (such as at least 20%, at least 30%, at least 40%, at least 50%, at least 60% at least 70%, at least 100%, at least 200%, at least 300%, or at least 400% more than a parent strain under the same growing conditions, such as about 20-50%, about 30-50%, or about 40-50% more).

3-HPDH sequences are publicly available. For example, SEQ ID NO: 18 discloses a 3-HPDH coding sequence and GenBank® Accession No: WP_000636571 discloses a 3-HPDH protein sequence (SEQ ID NO: 19); GenBank® Accession Nos. FR729477.2 (nt 1005136.1005885) and CBY27203.1 disclose exemplary *Yersinia enterocolitica* subsp. *palearctica* Y11 3-HPDH nucleic acid and protein sequences, respectively; and GenBank® Accession Nos: CP004083.1 (complement(1399227.1399973) and AJQ99264.1 disclose exemplary *Enterobacteriaceae bacterium* bta3-1 3-HPDH nucleic acid and protein sequences, respectively. However, one skilled in the art will appreciate that in some examples, a 3-HPDH sequence can include variant sequences (such as allelic variants and homologs) that retain 3-HPDH activity and when expressed in an *Aspergillus* also expressing BAPAT and panD and overexpressing aexA (e.g., from an exogenous nucleic acid molecule), and in some examples also having a genetically inactivated cadA gene (ΔcadA), results in a fungus that has an ability to produce more 3-HP than the parent strain (such as at least 20%, at least 30%, at least 40%, at least 50%, at least 60% at least 70%, at least 100%, at least 200%, at least 300%, or at least 400% more than a parent strain under the same growing conditions, such as about 20-50%, about 30-50%, or about 40-50% more).

Aconitic acid (AA): An organic acid with two isomers, cis- and trans-aconitic acid. The recombinant *Aspergillus* fungi provided herein that overexpress aexA (e.g., from an exogenous nucleic acid molecule), and in some examples also having a genetically inactivated cadA gene (ΔcadA), can be used to produce cis- and/or trans-aconitic acid.

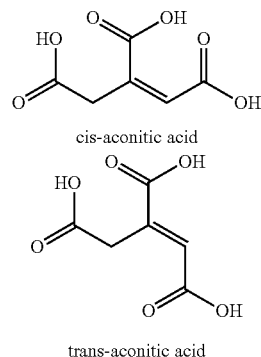

cis-aconitic acid trans-aconitic acid

Aconitic acid exporter (aexA, g8846): The aexA gene encodes a cell membrane protein responsible for the transport of aconitic acid from a cell, such as from *Aspergillus*. The term aexA (or aexA or g8846) includes any aexA gene (such as an endogenous fungal aexA sequence), cDNA, mRNA, or protein, that is a aexA that can export AA from a cell, and when genetically overexpressed results in an *Aspergillus* that secretes more AA than a strain without a (1) genetically overexpressed aexA gene and (2) endogenous cadA expression (ΔcadA) (see FIGS. 4A-4C, such as at least 2-fold, at least 3-fold, at least 4-fold, or at least 5-fold more than a strain without (1) a genetically overexpressed aexA gene and (2) endogenous cadA expression (ΔcadA) under the same growing conditions, for example at day 7 of production).

aexA sequences are publicly available for many species of *Aspergillus*. For example, using the aexA sequences shown in SEQ ID NOS: 1 and 2 for *A. pseudoterreus*, additional aexA sequences can be identified from publicly available databases (for example using blastp, see FIG. 5 for exemplary GenBank® Accession Nos: identified). GenBank® Accession Nos: GES58946.1 (SEQ ID NO: 3) and BKZM02000003.1:443944.445205 disclose *Aspergillus terreus* aexA protein and nucleic acid sequences, respectively; GenBank® Accession Nos: NEXV01000567.1 and PIG81326.1 (SEQ ID NO: 4) disclose *Aspergillus arachidicola* aexA nucleic acid and protein sequences, respectively; and GenBank® Accession Nos: KAE8152815.1 (SEQ ID NO: 5) and ML742047.1 disclose *Aspergillus avenaceus* aexA protein and nucleic acid sequences, respectively. However, one skilled in the art will appreciate that in some examples, an aexA sequence can include variant sequences (such as allelic variants and homologs) that retain aexA activity but when overexpressed in *Aspergillus* results in a fungus that produces more aconitic acid than an *Aspergillus* fungus (1) without genetically overexpressed aexA gene and (2) without endogenous cadA expression (ΔcadA) (see FIGS. 4A-4C, such as at least 2-fold, at least 3-fold, at least 4-fold, or at least 5-fold more than a strain (1) without a genetically overexpressed aexA gene and (2) without endogenous cadA expression (ΔcadA) under the same growing conditions, for example at day 7 of production).

Aspartate 1-decarboxylase (panD): EC 4.1.1.11. An enzyme that catalyzes the chemical reaction: L-aspartate⇌beta-alanine+$CO_2$. The term panD includes any panD gene (such as a bacterial or fungal panD sequence), cDNA, mRNA, or protein, that is a panD that can covert L-aspartate into beta-alanine+$CO_2$ and vice versa. Expression or increased expression of panD, for example in an *Aspergillus* also expressing BAPAT and 3-HPDH and overexpressing aexA (e.g., from an exogenous nucleic acid molecule), and in some examples also having a genetically inactivated cadA gene (ΔcadA), results in a fungus that has an ability to produce more 3-HP than the parent strain (such as at least 20%, at least 30%, at least 40%, at least 50%, at least 60% at least 70%, at least 100%, at least 200%, at least 300%, or at least 400% more than a parent strain under the same growing conditions, such as about 20-50%, about 30-50%, or about 40-50% more).

panD sequences are publicly available. For example, GenBank® Accession Nos: NM_001102585.1 and NP_001096055.1 disclose *Tribolium castaneum* panD nucleic acid and protein sequences, respectively (SEQ ID NOS: 12 and 13); GenBank® Accession Nos. CP002745.1 (complement(4249351.4249824)) and AEK63458.1 disclose exemplary *Collimonas fungivorans* Ter331 panD nucleic acid and protein sequences, respectively; and GenBank® Accession Nos: CP029034.1 (nt 1201611.1201994) and AWE15802.1 disclose exemplary *Bacillus velezensis* panD nucleic acid and protein sequences, respectively. However, one skilled in the art will appreciate that in some examples, a panD sequence can include variant sequences (such as allelic variants and homologs) that retain panD activity and when expressed in an *Aspergillus* also expressing BAPAT and 3-HPDH and overexpressing aexA (e.g., from an exogenous nucleic acid molecule), and in some examples also having a genetically inactivated cadA gene (ΔcadA), results in a fungus that has an ability to produce more 3-HP than the parent strain (such as at least 20%, at least 30%, at least 40%, at least 50%, at least 60% at least 70%, at least 100%, at least 200%, at least 300%, or at least 400% more than a parent strain under the same growing conditions, such as about 20-50%, about 30-50%, or about 40-50% more).

β-alanine-pyruvate aminotransferase (BAPAT): EC 2.6.1.18. An enzyme that can catalyze the reaction L-alanine+3-oxopropanoate⇌beta-alanine+pyruvate. The term BAPAT includes any BAPAT gene (such as a bacterial or fungal panD sequence), cDNA, mRNA, or protein, that is a BAPAT that can convert beta-alanine and pyuvate to L-alanine and 3-oxopropanoate [or malonic semialdehyde], and vice versa. Expression or increased expression of BAPAT, for example in an *Aspergillus* also expressing 3-HPDH and panD and overexpressing aexA (e.g., from an exogenous nucleic acid molecule), and in some examples also having a genetically inactivated cadA gene (ΔcadA), results in a fungus that has an ability to produce more 3-HP than the parent strain (such as at least 20%, at least 30%, at least 40%, at least 50%, at least 60% at least 70%, at least 100%, at least 200%, at least 300%, or at least 400% more than a parent strain under the same growing conditions, such as about 20-50%, about 30-50%, or about 40-50% more).

BAPAT sequences are publicly available. For example, GenBank® Accession Nos: ACMS01000158.1 (complement(10606.11961)) and EEL86940.1 disclose *Bacillus cereus* AH1272 BAPAT nucleic acid and protein sequences, respectively (SEQ ID NOS: 15 and 16); GenBank® Accession Nos. DF820429.1 (complement (241627.242967)) and GAK28710.1 disclose exemplary *Serratia liquefaciens* FK01 BAPAT nucleic acid and protein sequences, respectively; and GenBank Accession Nos: LGUJ01000001.1 complement (92812.94140) and KOY12524.1 disclose exemplary *Bradyrhizobium diazoefficiens* BAPAT nucleic acid and protein sequences, respectively. However, one skilled in the art will appreciate that in some examples, a BAPAT sequence can include variant sequences (such as allelic variants and homologs) that retain BAPAT activity and when expressed in an *Aspergillus* also expressing 3-HPDH and panD and overexpressing aexA (e.g., from an exogenous nucleic acid molecule), and in some examples also having a genetically inactivated cadA gene (ΔcadA), results in a fungus that has an ability to produce more 3-HP than the parent strain (such as at least 20%, at least 30%, at least 40%, at least 50%, at least 60% at least 70%, at least 100%, at least 200%, at least 300%, or at least 400% more than a parent strain under the same growing conditions, such as about 20-50%, about 30-50%, or about 40-50% more).

cadA (cis-aconitic acid decarboxylase): The cadA gene encodes an enzyme (EC 4.1.1.6) that catalyzes the chemical reaction cis-aconitate⇌itaconate+$CO_2$. The term cadA (or cadA) includes any cadA gene (such as an endogenous fungal cadA sequence), cDNA, mRNA, or protein, that is a cadA that can catalyze the decarboxylation of cis-aconitate to itaconate and $CO_2$ and vice versa, and when genetically inactivated results in a fungus that produces more aconitic acid than the parent strain without a genetically inactivated cadA gene (see FIGS. 4A-4C, such as at least 20%, at least 30%, at least 50%, at least 60%, at least 75%, at least 100%, at least 200%, at least 500%, or 1000% more than a parent strain under the same growing conditions, for example at day 5 of production). In some examples, a parental strain containing a functional native cadA sequence does not produce detectable aconitic acid (see FIGS. 4A-4C). In some examples, genetic inactivation of cadA results in an *Aspergillus* that produces more trans-aconitic acid than cis-aconitic acid at day 10 of production, (such as at least 2-fold, at least 3-fold, at least 4-fold, or at least 5-fold more at day 10 of production).

cadA sequences are publicly available for many species of *Aspergillus*. For example, GenBank® Accession Nos: AB326105.1 and BAG49047.1 disclose *Aspergillus terreus* cadA nucleic acid and protein sequences, respectively (SEQ ID NOS: 6 and 7); GenBank® Accession Nos: XM_025706777.1 and XP_025563141.1 disclose *Aspergillus vadensis* CBS 113365 cadA nucleic acid and protein sequences, respectively (SEQ ID NOS: 8 and 9); and GenBank® Accession Nos: XM_025663103.1 and XP_025520527.1 disclose *Aspergillus piperis* CBS 112811 cadA nucleic acid and protein sequences, respectively. However, one skilled in the art will appreciate that in some examples, a cadA sequence can include variant sequences (such as allelic variants and homologs) that retain cadA activity but when genetically inactivated in *Aspergillus* results in a fungus that has an ability to produce more aconitic acid than the parent strain without a genetically inactivated cadA gene (such as at least 20%, at least 30%, at least 50%, at least 60%, at least 75%, at least 100%, at least 200%, at least 500%, or 1000% more than a parent strain under the same growing conditions, for example at day 5 of production).

Detectable: Capable of having an existence or presence ascertained. For example, production of aconitic acid, citric acid, or 3-HP is detectable if the signal generated is strong enough to be measurable.

Exogenous: The term "exogenous" as used herein with reference to nucleic acid and a particular cell refers to any nucleic acid that does not originate from that particular cell as found in nature. Thus, a non-naturally-occurring nucleic acid is considered to be exogenous to a cell once introduced into the cell. A nucleic acid that is naturally-occurring also can be exogenous to a particular cell. For example, an entire chromosome isolated from cell X is an exogenous nucleic acid with respect to cell Y once that chromosome is introduced into cell Y, even if X and Y are the same cell type.

In some examples, a nucleic acid molecule used to overexpress aexA is exogenous to the *Aspergillus* into which it is introduced, as even if the aexA sequence is endogenous, it is operably linked to a non-endogenous promoter, making the entire nucleic acid molecule exogenous as it does not naturally occur in the *Aspergillus* fungi.

In some examples, the panD, BAPAT, and 3-HPDH nucleic acid or protein expressed in *Aspergillus* does not naturally occur in that strain or species of *Aspergillus* and is therefore exogenous to that fungi. For example, panD, BAPAT, and 3-HPDH nucleic acid molecule introduced into an *Aspergillus terreus* or *Aspergillus pseudoterreus* fungi can be from another organism, such as a bacterial panD, BAPAT, and 3-HPDH sequence.

Genetic enhancement or up-regulation: When used in reference to the expression of a nucleic acid molecule, such as a gene, refers to any process which results in an increase in production of a gene product (such as an aexA protein). A gene product can be RNA (such as mRNA, rRNA, tRNA, and structural RNA) or protein. Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Gene up-regulation can include inhibition of repression as well as expression above an existing level. Examples of processes that increase translation include those that increase translational initiation, those that increase translational elongation and those that increase mRNA stability. In one example, additional copies of genes are introduced into a cell in order to increase expression of that gene in the resulting transgenic cell.

Gene up-regulation includes any detectable increase in the production of a gene product. In certain examples, production of a gene product increases by at least 1.5-fold, at least 2-fold, at least 3-fold, at least 4-fold, or at least 5-fold), such as aexA, aspartate decarboxylase (panD), β-alanine-pyruvate aminotransferase (BAPAT), and/or 3-HPDH. In one example, expression of an aexA gene in *Aspergillus* (e.g., *A. terreus*) results in an *Aspergillus* strain having an increased amount of aexA protein, relative to the parent strain, which can permit the recombinant fungus to export greater amounts of AA. Genetic enhancement is also referred to herein as "enhancing or increasing expression."

Genetic inactivation or down-regulation: When used in reference to the expression of a nucleic acid molecule, such as a gene, refers to any process which results in a decrease in production of a gene product. A gene product can be RNA (such as mRNA, rRNA, tRNA, and structural RNA) or protein. Therefore, gene down-regulation or deactivation includes processes that decrease transcription of a gene or translation of mRNA.

For example, a mutation, such as a substitution, partial or complete deletion, insertion, or other variation, can be made to a gene sequence that significantly reduces (and in some cases eliminates) production of the gene product or renders the gene product substantially or completely non-functional. For example, a genetic inactivation of an endogenous cadA gene in *Aspergillus* (e.g., *A. pseudoterreus*) results in the *Aspergillus* having a non-functional or non-detectable cadA protein, which results in the recombinant fungus producing more aconitic acid than the parent strain with a native/non-mutated/non-deleted cadA sequence (see FIGS. 4A-4C, Δcad vs cad+). Genetic inactivation is also referred to herein as "functional deletion".

Isolated: To be significantly separated from other agents. An "isolated" biological component (such as a nucleic acid molecule or protein) has been substantially separated, produced apart from, or purified away from other biological components in the cell of the organism in which the component occurs, for example, other chromosomal and extrachromosomal DNA and RNA, and proteins. Nucleic acid molecules and proteins which have been "isolated" include nucleic acid molecules and proteins purified by standard purification methods. The term also embraces nucleic acid molecules and proteins prepared by recombinant expression in a host cell as well as chemically synthesized proteins and nucleic acids. Samples of isolated biological components include samples of the biological component wherein the biological component represents greater than 90% (for example, greater than 95%, such as greater than 98%) of the sample.

An "isolated" microorganism (such as a *Aspergillus* overexpressing aexA, and in some examples also ΔcadA) has been substantially separated or purified away from microorganisms of different types, strains, or species. Microorganisms can be isolated by a variety of techniques, including serial dilution and culturing and resistance to certain chemicals, such as antibiotics. In some examples, an isolated *Aspergillus* strain overexpressing aexA (and in some examples is also ΔcadA) is at least 90% (for example, at least 95%, as at least 98%, at least 99%, or at least 99.99%) pure.

Mutation: A change in a nucleic acid sequence (such as a gene sequence) or amino acid sequence, for example as compared to a nucleic acid or amino acid sequence present in a wild-type or native organism. In particular examples, a mutation is introduced into an endogenous cadA gene in *Aspergillus*, thereby rendering it non-functional. Mutations can be introduced, for example using molecular biology methods (e.g., thereby generating a recombinant or transformed cell or microorganism). In particular examples, a mutation includes one or more nucleotide substitutions, deletions, insertions, or combinations thereof. In particular examples, the presence of one or more mutations in a gene can significantly inactivate and reduce expression of that gene (such as an endogenous cadA gene).

Promoter: An array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. In some examples, a promoter is bi-directional. Native and non-native promoters (i.e., endogenous and exogenous) can be used to drive expression of a gene, such as aexA, panD, BAPAT, and 3-HPDH. Exemplary promoters that can be used include but are not limited to: enol promoter from A. niger, and dth1 from A. nidulans or A. niger.

Additional examples of promoters that can be used include, but are not limited to the SV40 promoter, the CMV enhancer-promoter, and the CMV enhancer/β-actin promoter. Both constitutive and inducible promoters can be used in the fungi and methods provided herein (see e.g., Bitter et al., *Methods in Enzymology* 153:516-544, 1987). Also included are those promoter elements which are sufficient to render promoter-dependent gene expression controllable for cell-type specific, tissue-specific, or inducible by external signals or agents; such elements may be located in the 5' or 3' regions of the gene. Promoters produced by recombinant DNA or synthetic techniques can also be used to provide for transcription of the nucleic acid sequences.

Recombinant: A recombinant nucleic acid molecule or protein is one that has a sequence that is not naturally occurring (such as an exogenous promoter operably linked to a native aexA coding sequence) or has a sequence that is made by an artificial combination of two otherwise separated segments of sequence. In particular examples, this artificial combination is accomplished by chemical synthesis or by the artificial manipulation of isolated segments of nucleic acids, for example, by genetic engineering techniques such as those described in Sambrook et al. (ed.), Molecular Cloning: A Laboratory Manual, 3d ed., vol. 1-3, Cold Spring Harbor Laboratory Press, Cold Spring Harbor, NY, 2001. The term recombinant includes nucleic acid molecules that have been altered solely by addition, substitution, or deletion of a portion of the nucleic acid molecule. A recombinant or transformed organism or cell, such as a recombinant *Aspergillus*, is one that includes at least one exogenous nucleic acid molecule, such as one used to overexpress aexA, one used to genetically inactivate an endogenous cadA gene, or one used to express a non-native protein such as exogenous panD, BAPAT, and 3-HPDH nucleic acid coding sequences.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, MD 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. For example, the following command can be used to generate an output file containing a comparison between two sequences: C:\Bl2seq c:\seq1.txt -j c:\seq2.txt -p blastn -o c:\output.txt -q -1 -r 2.

To compare two amino acid sequences, the options of Bl2seq can be set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (e.g., 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (i.e., 1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (i.e., 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG. In addition, a manual alignment can be performed. Proteins with even greater similarity will show increasing percentage identities when assessed by this method, such as at least 75%, 80%, 85%, 90%, 95%, or 99% sequence identity.

Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least 60%, 70%, 80%, 90%, 95%, 98%, or 99% sequence identity determined by this method.

One of skill in the art will appreciate that these sequence identity ranges are provided for guidance only; it is possible that strongly significant homologs could be obtained that fall outside the ranges provided. Thus, a variant aexA, cadA, panD, BAPAT, or 3-HPDH protein or nucleic acid molecule that can be used with the organisms and methods of the present disclosure can have at least 80%, at least 85%, at least 90%, at least 91%, at least 92%, at least 93%, at least 94%, at least 95%, at least 96%, at least 97%, at least 98% or at least 99% sequence identity to the SEQ ID NOs: and GenBank® Accession Nos. provided herein.

Transformed: A cell, such as a fungal cell, into which a nucleic acid molecule has been introduced, for example by molecular biology methods. As used herein, the term transformation encompasses all techniques by which a nucleic acid molecule might be introduced into such a cell, including, but not limited to chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses. In one example, a protoplast transformation method is used, such as the on described in Example 1.

Vector: A nucleic acid molecule as introduced into a host cell, thereby producing a transformed or recombinant host cell. A vector may include nucleic acid sequences that permit it to replicate in the host cell, such as an origin of replication. A vector may also include an aexA, panD, BAPAT, and/or 3-HPDH coding sequence, and/or a sequence used to genetically inactivate cadA, for example in combination with a promoter, and/or selectable marker genes, and other genetic elements. A vector can transduce, transform or infect a cell, thereby causing the cell to express nucleic acids and/or proteins. A vector optionally includes materials to aid in achieving entry of the nucleic acid into the cell, such as a viral particle, liposome, protein coating or the like. In one example, a vector is a plasmid, such as a plasmid exogenous to the cell or organism into which it is introduced.

Overview

Currently, trans-aconitc acid is produced by chemical synthesis and requires high temperature and harmful solvents. Generation of trans-aconitic acid has been achieved by metabolic engineering aconitase isomerase from *Pseudomonas* sp. WU-0701 into *E. coli*. However, the substrate for the recombinant *E. coli* to produce trans-aconitic acid is citric acid, which is generated first from fermentation. In contrast, the disclosed recombinant fungi can produce trans-aconitic acid directly from renewable biomass substrates.

Figure 4A:
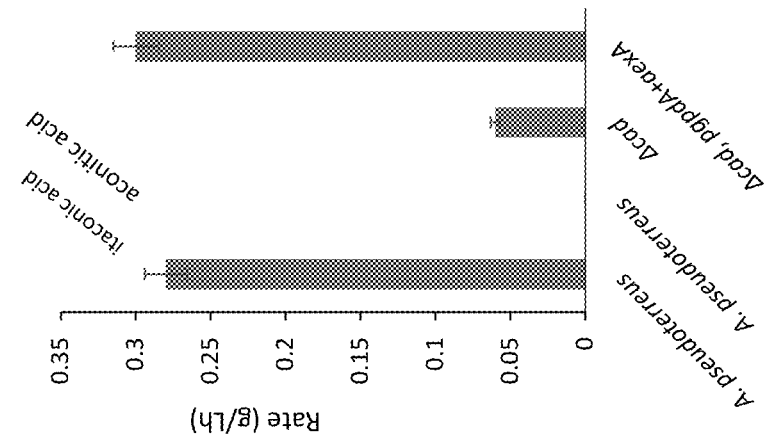
FIGS. 4A-4C are bar graphs showing the effect of aexA (g8846) overexpression using SEQ ID NO: 21 on titer, yield and rate of aconitic acid in *A. pseudoterreus*. The first bar shows itaconic acid production in wild type *A. pseudoterreus*. The three other bars show aconitic acid production in *A. pseudoterreus* with wild type cadA (cadA+), with endogenous cadA deleted (ΔcadA), and with endogenous cadA deleted and aexA overexpressed from a gpdA promoter (ΔcadA+pgpdA+aexA).
Figure 4B:
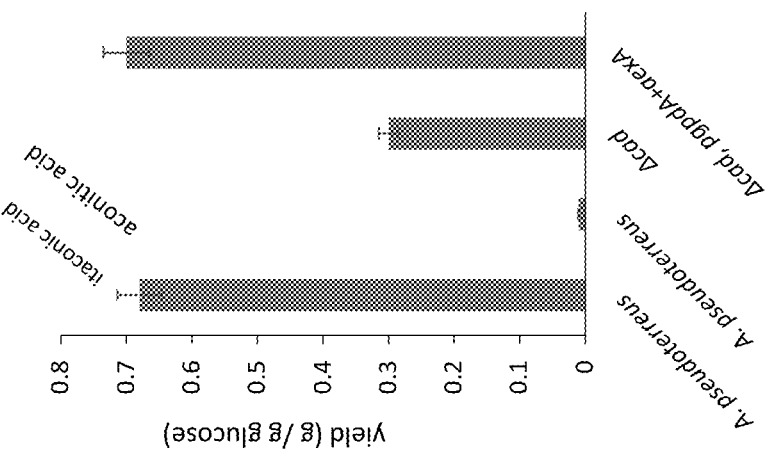
Figure 4C:
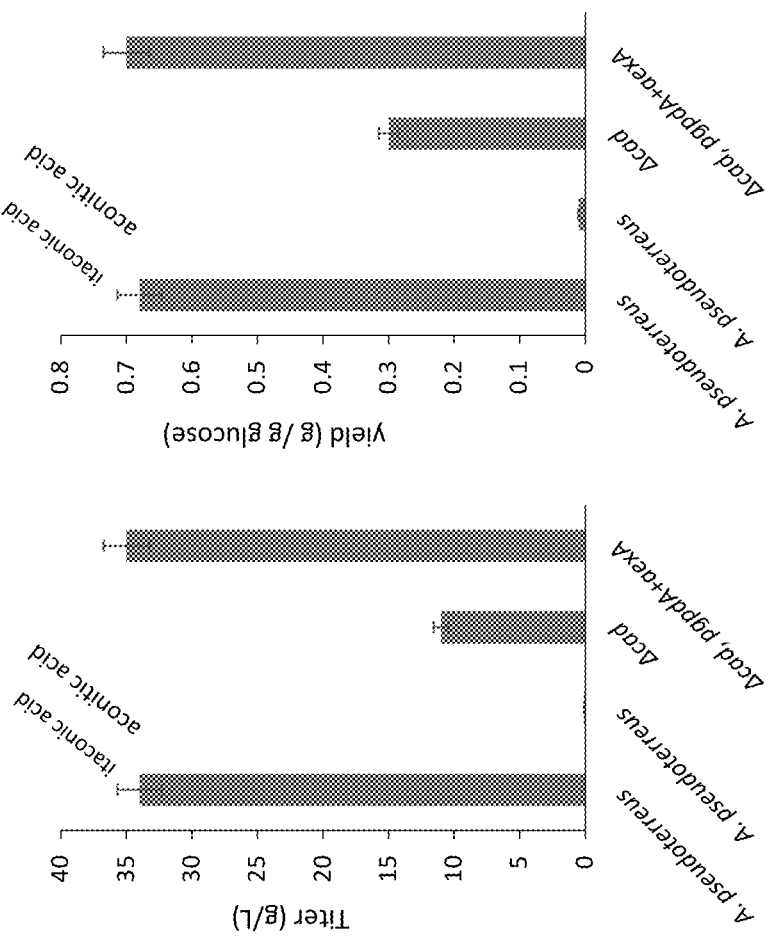

*A. pseudoterreus* naturally produces a large amount of itaconic acid (see FIGS. 4A-4C, cad+, Deng et al. 2020, Li et al. 2011). As shown in FIG. 1, glucose is utilized by *A. pseudoterreus* to form pyruvate and is subsequently converted to citric acid in the TCA cycle in the mitochondria. Citric acid is dehydrated to cis-AA, which then is transported from the mitochondria into the cytosol via transporter. In the cytosol, cis-AA is decarboxylated into itaconic acid and $CO_2$ by CAD. Genetic deletion of cadA results in cis-AA that cannot be converted into itaconic acid. As a result, AA accumulates in the cell, and then is exported outside the cell. However, AA production is much lower than itaconic acid in the parent strain (compare first and third bars in FIGS. 4A-4C).

Figure 3:
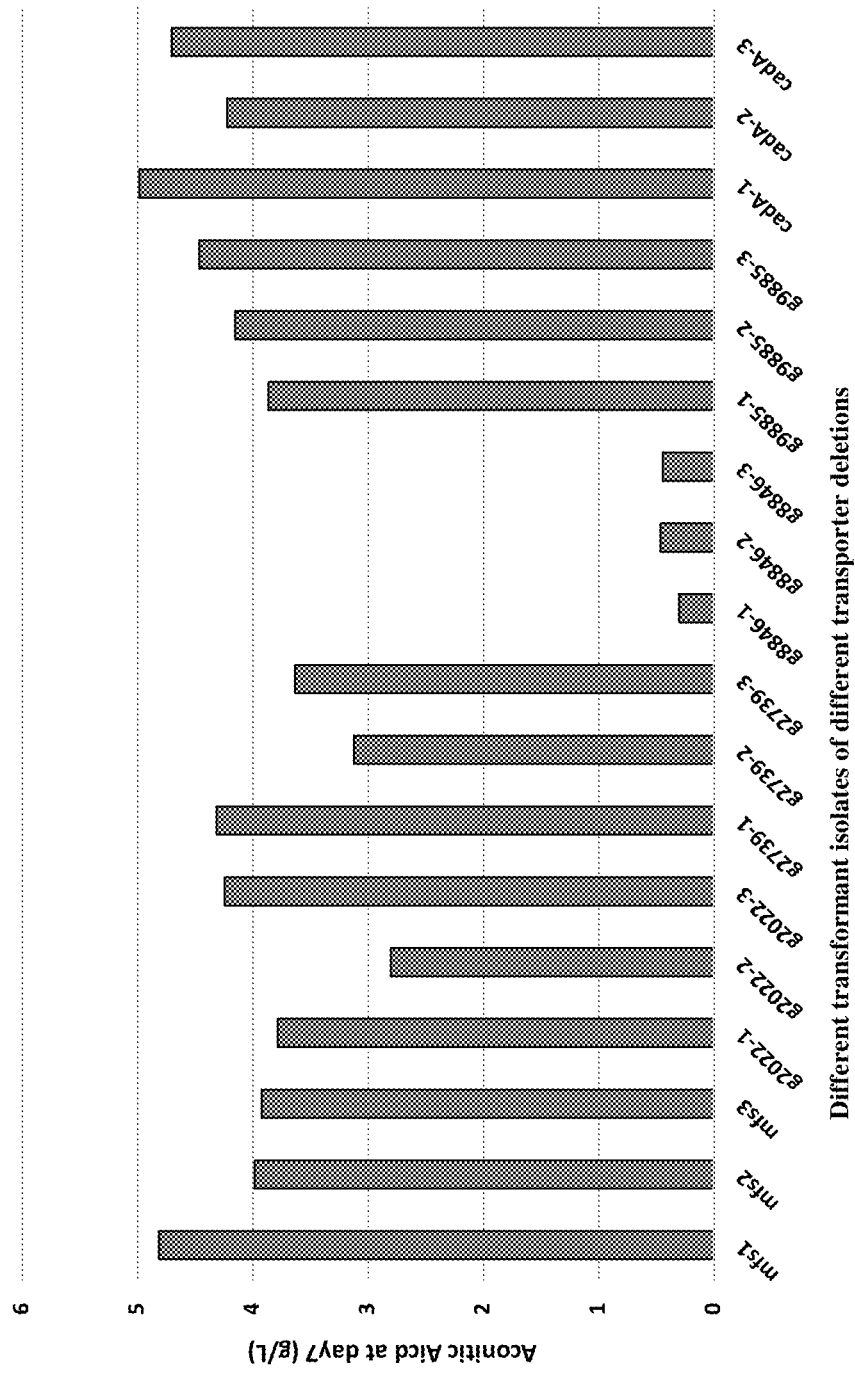
FIG. 3 is a bar graph showing the production of AA from different transporter gene deletions (g2022, g2739, g8846, and g9885). mfs is an itaconic acid transporter. Results for *A. pseudoterreus* with a cadA deletion are also shown (cadA-1, cadA-2 and cadA-3).

It was investigated whether the specific AA exporter on the cell membrane was a limiting factor. The inventors performed comparative proteomics analysis on membrane proteins in both wild type *A. pseudoterreus* and cadA deletion (ΔcadA) stains to identify aconitic acid transporter candidates. Deletion assay results demonstrated that an aexA deletion dramatically decreased aconitic acid production (FIG. 3, g8846 clones). In contrast, overexpression of aexA resulted in a significant increase in secreted aconitic acid. The yield of AA is as high as itaconic acid in parent (native aexA, cad+) itaconic acid producing strain (FIGS. 4A-4C). The exporter aexA for aconitic acid was saturated at low level in a ΔcadA strain (10 g/L). However, when overexpressed, export of AA increased to 50 g/L. Thus, the recombinant *Aspergillus* and methods provided herein can be used for industry-scale production of AA since it shares same industry process and infrastructure as itaconic acid.

Provided herein are isolated recombinant *Aspergillus* fungi that include one or more exogenous nucleic acid molecules encoding aconitic acid exporter (aexA or g8846) operably linked to an exogenous promoter, thereby overexpressing the aexA in the fungus. Introduction of the one or more exogenous nucleic acid molecules encoding aexA operably linked to an exogenous promoter results in integration of at least the exogenous promoter and the operably linked aexA coding sequence into the genome of the recombinant *Aspergillus*. Such recombinant *Aspergillus* fungi are referred to herein as aexA+. The aexA exporter protein is expressed at the cell membrane. The coding sequence of aexA may be endogenous to the particular *Aspergillus*, but is operably linked to an exogenous/heterologous promoter, that is one in nature that does not drive expression of aexA in the particular strain or species of *Aspergillus*. Exemplary promoters include gpdA (for example from *A. niger*, see SEQ ID NO: 30 or *A. nidulans*, see SEQ ID NO: 33), and enol (for example from *A. niger*, see SEQ ID NO: 32). The one or more exogenous nucleic acid molecules can be part of a vector, such as a plasmid. In some examples, the nucleic acid molecule encoding aexA overexpressed in *Aspergillus* has at least 60%, at least 65%, at least 70%, at least 75%, at least 80%, at least 85%, at least 90%, at least 95%, at least 96%, at least 97%, at least 98%, at least 99%, or 100% sequence identity to SEQ ID NO: 1 (or any sequence referred to in FIG. 5). In some examples, the nucleic acid molecule encoding aexA overexpressed in *Aspergillus* encodes a protein having at least 60%, at least 65%, at least 70%, at least 75%, at least 80%, at least 85%, at least 90%, at least 95%, at least 96%, at least 97%, at least 98%, at least 99%, or 100% sequence identity to SEQ ID NO: 2, 3, 4, or 5 (or any sequence referred to in FIG. 5). In some examples, the *Aspergillus* is *Aspergillus pseudoterreus*, *Aspergillus terreus*, *Aspergillus niger*, or *Aspergillus oryzae*. In some examples, overexpression of aexA is determined by measuring AA production by the recombinant *Aspergillus*.

In some examples, such a recombinant *Aspergillus* fungi includes other genetic alterations, such as a genetically inactivated endogenous cis-aconitic acid decarboxylase (cadA) gene. Such recombinant *Aspergillus* fungi are referred to herein as aexA+/ΔcadA. In some examples, the endogenous cadA gene is genetically inactivated by mutation (such as a complete or partial deletion of the cadA gene) or by insertional mutation (such as by insertion of another nucleic acid molecule into the cadA gene, such as an antibiotic resistance marker). In one example, the endogenous cadA gene in the strain or species of *Aspergillus* is genetically inactivated by complete deletion. Exemplary cadA gene sequences that can be genetically inactivated are provided herein. In some examples, the cadA gene, prior to its genetic inactivation, encodes a protein having at least 80%, at least 85%, at least 90%, at least 95%, at least 96%, at least 97%, at least 98%, at least 99%, or 100% sequence identity to SEQ ID NO: 7 or 9. In some examples, the cadA gene, prior to its genetic inactivation, has a coding sequence having at least 80%, at least 85%, at least 90%, at least 95%, at least 96%, at least 97%, at least 98%, at least 99%, or 100% sequence identity to SEQ ID NO: 6, 8, 10 or 11. In one example, decreased or elimination of cadA activity by a particular recombinant *Aspergillus* strain is determined by measuring decarboxylation of cis-aconitic acid into itaconic acid and carbon dioxide (Bentley & Thiessen, 1955, Science, 122(3164), 330).

The disclosed recombinant *Aspergillus* fungi can express other genes/proteins (endogenous or exogenous) needed to permit the fungi to produce other organic acids. For example, the disclosed aexA+ and aexA+/ΔcadA fungi can further include an endogenous or exogenous nucleic acid molecule encoding aspartate 1-decarboxylase (panD), an endogenous or exogenous nucleic acid molecule encoding β-alanine-pyruvate aminotransferase (BAPAT), and an endogenous or exogenous nucleic acid molecule encoding 3-hydroxypropionate dehydrogenase (3-HPDH). panD, BAPAT, and 3-HPDH coding sequences can be part of a one or more nucleic acid molecules, such as a vector. In addition, expression of the panD, BAPAT, and 3-HPDH coding sequences can be driven by one or more promoters, such as a bi-directional promoter. In some examples, the promoter is native to the gene it is expressing. In some examples, the promoter is from *A. niger*. In some examples, the panD, BAPAT, and/or 3-HPDH coding sequences are inserted into the cadA gene, genetically inactivating cadA. In some examples, the nucleic acid molecule encoding panD has at least 80%, at least 90%, at least 95%, at least 98%, at least 99%, or 100% sequence identity to SEQ ID NO: 12 or 14, and/or encodes a panD protein comprising at least 80%, at least 90%, at least 95%, at least 98%, at least 99%, or 100% sequence identity to SEQ ID NO: 13. In some examples, the nucleic acid molecule encoding BAPAT has at least 80%, at least 90%, at least 95%, at least 98%, at least 99%, or 100% sequence identity to SEQ ID NO: 15 or 17, and/or encodes a BAPAT protein having at least 80%, at least 90%, at least 95%, at least 98%, at least 99%, or 100% sequence identity to SEQ ID NO: 16. In some examples, the nucleic acid molecule encoding 3-HPDH has at least 80%, at least 90%, at least 95%, at least 98%, at least 99%, or 100% sequence identity to SEQ ID NO: 18 or 20, and/or encodes a 3-HPDH protein having at least 80%, at least 90%, at least 95%, at least 98%, at least 99%, or 100% sequence identity to SEQ ID NO: 19.

Also provided are isolated nucleic acid molecules that include a heterologous promoter operably linked to an aexA coding sequence, wherein the promoter is not endogenous to the aexA coding sequence. The one or more exogenous nucleic acid molecules can be part of a vector, such as a plasmid. In some examples, the aexA coding sequence s has at least 60%, at least 65%, at least 70%, at least 75%, at least 80%, at least 85%, at least 90%, at least 95%, at least 96%, at least 97%, at least 98%, at least 99%, or 100% sequence identity to SEQ ID NO: 1 (or any sequence referred to in FIG. 5). In some examples, the aexA coding sequence encodes a protein having at least 60%, at least 65%, at least 70%, at least 75%, at least 80%, at least 85%, at least 90%, at least 95%, at least 96%, at least 97%, at least 98%, at least 99%, or 100% sequence identity to SEQ ID NO: 2, 3, 4, or 5 (or any sequence referred to in FIG. 5). Exemplary promoters include gpdA (for example from *A. niger*, see SEQ ID NO: 30 or *A. nidulans*, see SEQ ID NO: 33), and enol (for example from *A. niger*, see SEQ ID NO: 32). In some examples, the promoter has at least 80%, at least 90%, at least 95%, at least 98%, at least 99%, or 100% sequence identity to SEQ ID NO: 30, 32, or 33, wherein the promoter does not have a native or endogenous sequence to the aexA coding sequence. In some examples, the nucleic acid molecule further includes a terminator sequence following the aexA coding sequence, such as TrpC (e.g., from *A. nidulans*, see nt 5679-6465 of SEQ ID NO: 21) or elf3/multifunctional chaperone (e.g., from *A. niger*, see SEQ ID NO: 31). In some examples, the terminal sequence has at least 80%, at least 90%, at least 95%, at least 98%, at least 99%, or 100% sequence identity to nt 5679-6465 of SEQ ID NO: 21 or to SEQ ID NO: 31. In some examples, the nucleic acid molecule has at least 80%, at least 90%, at least 95%, at least 98%, at least 99%, or 100% sequence identity to nt 2952-6678 or nt 2952-6465 of SEQ ID NO: 21. In some examples, such a nucleic acid molecule is part of a vector, such as a plasmid. In some examples, such a plasmid has at least 80%, at least 90%, at least 95%, at least 98%, at least 99%, or 100% sequence identity to SEQ ID NO: 21. Also provided are compositions and kits that include such nucleic acid molecules and plasmids. Such a composition can include a pharmaceutically acceptable carrier, such as water or saline. Such a kit can further include reagents for transforming *Aspergillus*, such as protoplast isolation buffer, osmotic wash buffer, polyethylene glycol, filtration material (such as miracloth), antibiotic (e.g., hygromicin), or combinations thereof, growth media (such as complete media, minimal media, Riscaldati medium, modified Riscaldati medium with 20× trace elements)), or combinations thereof. Such reagents can be in separate containers of the kit.

The disclosure also provides compositions that include the disclosed aexA+ and aexA+/ΔcadA recombinant *Aspergillus* that express or overexpress other genes (such as panD, BAPAT, and 3-HPDH). Such a composition can include a solid or liquid culture or growth media, such as complete media, minimal media, or Riscaldati medium (such as modified Riscaldati medium with 20× trace elements).

The disclosure also provides kits that include the disclosed aexA+ and aexA+/ΔcadA fungi, and such *Aspergillus* that express or overexpress other genes (such as panD, BAPAT, and 3-HPDH). Such kits can include a solid or liquid culture or growth media, such as complete media, minimal media, or Riscaldati medium (such as modified Riscaldati medium with 20× trace elements). In some examples, a kit also includes one or more reagents to allow transformation of *Aspergillus*, such as protoplast isolation buffer, osmotic wash buffer, polyethylene glycol, filtration material (such as miracloth), antibiotic (e.g., hygromicin), or combinations thereof.

Also provided are methods of using the disclosed aexA+ and aexA+/ΔcadA fungi to make aconitic acid. Such a method can include culturing the recombinant *Aspergillus* fungi under conditions that permit the fungus to make aconitic acid, such as growth in Riscaldati medium, thereby making aconitic acid. In some examples, the aconitic acid generated is cis-aconitic acid, trans-aconitic acid, or both. In some examples, the disclosed aexA+ and aexA+/ΔcadA fungi produce at least 2-fold, at least 3-fold, at least 4-fold, at least 5-fold, at least 10-fold, at least 20-fold, at least 30-fold, at least 40-fold, or at least 50-fold more AA than an amount of AA produced by an *Aspergillus* fungus of the same species and strain with native aexA expression (and in some examples also native cadA expression). In some examples, the fungi are cultured at room temperature (e.g., 20-35° C., such as about 30° C.) at normal atmospheric pressure (e.g., 1 atm). In some examples, the method includes purifying or isolating the aconitic acid, for example from the culture media or from the cultured fungus. In some examples, the aconitic acid is isolated at least 2 days, at least 3 days, at least 5 days, at least 7 days, at least 8 days or at least 10 days after the start of culturing, such as 2, 3, 4, 5, 6, 7, 8, 9, 10, 11, 12, 13, 14, 15, 16, 17, 18, 19 or 20 days after the start of culturing. Thus, in some examples, the disclosed aexA+ and aexA+/ΔcadA fungi work as biocatalyst that converts biomass into aconitic acid through bioproduction method at room temperature (such as about 20-35° C.) and ordinary pressure (such as about 1 atm). Current processes of aconitic acid production include chemical synthesis that require high temperatures and harmful reagents.

Also provided are methods of using the disclosed aexA+ fungi to make citric acid. Such a method can include culturing a recombinant *Aspergillus niger* fungi that overexpresses aexA under conditions that permit the fungus to make citric acid, such as growth in citric acid production medium, thereby making citric acid. In some examples, the disclosed recombinant *Aspergillus niger* that overexpress aexA produce at least 5%, at least 10%, at least 12%, or at least 14% more (such as 5-20%, 5-15%, or 5-14% more) citric acid than an amount of citric acid produced by an *Aspergillus niger* of the same strain with native aexA expression. In some examples, the fungi are cultured at room temperature (e.g., 20-35° C., such as about 30° C.) at normal atmospheric pressure (e.g., 1 atm). In some examples, the method includes purifying or isolating the citric acid, for example from the culture media or from the cultured fungus. In some examples, the citric acid is isolated at least 2 days, at least 3 days, at least 5 days, at least 7 days, at least 8 days or at least 10 days after the start of culturing, such as 2, 3, 4, 5, 6, 7, 8, 9, 10, 11, 12, 13, 14, 15, 16, 17, 18, 19 or 20 days after the start of culturing.

Also provided are methods of using the disclosed recombinant *Aspergillus* that overexpress aexA to make itaconic acid. Such a method can include culturing a recombinant *Aspergillus pseudoterrus* fungi that overexpresses aexA under conditions that permit the fungus to make itaconic acid, such as growth in Riscaldati medium, thereby making itaconic acid. In some examples, the fungi are cultured at room temperature (e.g., 20-35° C., such as about 30° C.) at normal atmospheric pressure (e.g., 1 atm). In some examples, the method includes purifying or isolating the itaconic acid, for example from the culture media or from the cultured fungus. In some examples, the itaconic acid is isolated at least 2 days, at least 3 days, at least 5 days, at least 7 days, at least 8 days or at least 10 days after the start of culturing, such as 2, 3, 4, 5, 6, 7, 8, 9, 10, 11, 12, 13, 14, 15, 16, 17, 18, 19 or 20 days after the start of culturing.

Also provided are methods of using the disclosed aexA+ and aexA+/ΔcadA fungi, and which also express or overexpress panD, BAPAT, and 3-HPDH, to make 3-HP. Such a method can include culturing the disclosed recombinant *Aspergillus* fungi expressing panD, BAPAT, and 3-HPDH under conditions that permit the fungus to make 3-HP, such as growth in Riscaldati medium (such as modified Riscaldati medium with 20× trace elements), thereby making 3-HP. In some examples, the disclosed recombinant *Aspergillus* (such as *A. niger*) that overexpress aexA produce at least 10%, at least 20%, at least 30%, at least 40%, or at least 50% more (such as 10-75%, 10-60%, 10-50%, or 25-50% more, such as about 50% more) 3-HP than an amount of 3-HP produced by an *Aspergillus* (such as *A. niger*) of the same strain with native aexA expression. In some examples, the fungi are cultured at room temperature (e.g., 20-35° C., such as about 30° C.) at normal atmospheric pressure (e.g., 1 atm). In some examples, the method includes purifying or isolating the 3-HP, for example from the culture media or from the cultured fungus. In some examples, the 3-HP is isolated at least 2 days, at least 3 days, at least 5 days, at least 7 days, at least 8 days or at least 10 days after the start of culturing, such as 2, 3, 4, 5, 6, 7, 8, 9, 10, 11, 12, 13, 14, 15, 16, 17, 18, 19 or 20 days after the start of culturing.

Recombinant Fungi

The present disclosure provides isolated recombinant *Aspergillus* fungi expressing one or more exogenous nucleic acid molecules that overexpress aexA from a heterologous (i.e., non-native) promoter. Such recombinant *Aspergillus* fungi are referred to herein as aexA+fungi or aexA+*Aspergillus*. In some examples, the recombinant *Aspergillus* fungi overexpressing aexA also have their cadA gene genetically inactivated (e.g., functionally deleted, ΔcadA). Such recombinant *Aspergillus* fungi are referred to herein as aexA+/ΔcadA fungi or aexA+/ΔcadA*Aspergillus*. It is shown herein that *Aspergillus* strains overexpressing aexA have increased aconitic acid (AA) production as compared to *Aspergillus* having native levels of aexA expression.

Any variety or strain of *Aspergillus* can be used. In particular examples, the *Aspergillus* fungus is *A. terreus* or *A. pseudoterreus*, as well as particular strains thereof (for example *A. terreus* NRRL 1960, *A. pseudoterreus* ATCC 32359). In some examples, the *Aspergillus* is *Aspergillus niger* or *Aspergillus oryzae*.

Any method for increasing expression of aexA can be used, as long as the expression of the aexA gene is significantly increased, or the function of the aexA protein is significantly increased. In particular examples, expression of an aexA gene is genetically enhanced by introducing a transgene that includes aexA coding or gene sequence operably linked to a heterologous promoter sequence. In some embodiments, increased expression refers to an increase of at least 20%, at least 30%, at least 40%, at least 50%, at least 60%, at least 70%, at least 80%, at least 90%, at least 100%, at least 200%, at least 300% at least 400%, or at least 500%. The term "increased" as used herein with respect to a cell and aexA gene or protein activity refers to a higher level of activity than that measured in a comparable cell of the same species without the transgene. For example, a particular *Aspergillus* expressing a recombinant aexA from a heterologous promoter sequence has increased aexA activity/expression if a comparable *Aspergillus* not having the transgene has lower aexA activity.

aexA sequences are disclosed herein and others are publicly available, for example from GenBank or EMBL. In some examples, the aexA gene overexpressed encodes a protein having at least 80%, at least 90%, at least 95%, at least 96%, at least 97%, at least 98%, at least 99%, or 100% sequence identity to SEQ ID NO: 2, 3, 4 or 5. In some examples, the endogenous aexA gene overexpressed has at least 80%, at least 90%, at least 95%, at least 96%, at least 97%, at least 98%, at least 99% or 100% sequence identity to SEQ ID NO: 1.

Similarly, any method of genetic inactivation of cadA can be used, as long as the expression of the endogenous cadA gene is significantly reduced or eliminated, or the function of the cadA protein is significantly reduced or eliminated. In particular examples, the cadA gene is genetically inactivated by complete or partial deletion mutation or by insertional mutation. In some examples genetic inactivation need not be 100%. In some embodiments, genetic inactivation refers to at least 50%, at least 60%, at least 70%, at least 80%, at least 90%, or at least 95% gene or protein inactivation. The term "reduced" or "decreased" as used herein with respect to a cell and a particular gene or protein activity refers to a lower level of activity than that measured in a comparable cell of the same species. For example, a particular *Aspergillus* lacking cadA activity has reduced cadA activity if a comparable *Aspergillus* not having a cadA genetic inactivation has detectable cadA activity.

cadA sequences are disclosed herein and others are publicly available, for example from GenBank or EMBL. In some examples, the cadA gene functionally deleted encoded a protein having at least 80%, at least 90%, at least 95%, at least 97%, at least 98%, at least 99%, or 100% sequence identity to SEQ ID NO: 7 or 9 prior to its genetic inactivation. In some examples, the endogenous cadA gene functionally deleted has at least 80%, at least 90%, at least 95%, at least 96%, at least 97%, at least 98%, at least 99% or 100% sequence identity to SEQ ID NO: 6, 8, 10, or 11 prior to its genetic inactivation.

Increased expression of aexA results in many phenotypes in a recombinant *Aspergillus*, such as *A. terreus* or *A. pseudoterreus*. For example, aexA+ or aexA+/ΔcadA mutants can produce at least 2-fold, at least 3-fold, at least 3.5 fold, at least 5-fold, at least 8-fold, at least 10-fold, at least 20-fold, at least 30-fold, at least 40-fold, or at least 50-fold more total aconitic acid than a wild-type *Aspergillus* (for example at day 3, 4, 5, 6, 7, 8, 9 or 10 of production). In some examples, such increases are relative to *Aspergillus terreus* strain ATCC 32359 grown under the same conditions as the aexA+ or aexA+/ΔcadA mutant. In some examples, an increased total aconitic acid production by aexA+ or aexA+/ΔcadA fungi occurs at least 3 days (such as at least 4, 5, 6, 7, 8, 9, or 10 days) after inoculation in Riscaldati medium (such as at least 0.5 g/L aconitic acid or at least 1 g/L aconitic acid), as compared to no detectable aconitic acid produced by *Aspergillus terreus* strain ATCC 32359 at the same time point.

Additional genes can also be upregulated or inactivated in the disclosed aexA+ and aexA+/ΔcadA fungi, wherein the additional genes may or may not provide additional enhancement of aconitic acid production to the fungus.

In some examples, the disclosed aexA+ and aexA+/ΔcadA fungi include one or more additional exogenous nucleic acid molecules, for example to permit production of other organic acids by the recombinant fungi. In one example, the disclosed aexA+ and aexA+/ΔcadA fungi includes an endogenous or exogenous nucleic acid molecule encoding aspartate decarboxylase (panD), an endogenous or exogenous nucleic acid molecule encoding β-alanine-pyruvate aminotransferase (BAPAT), and an endogenous or exogenous nucleic acid molecule encoding 3-hydroxypropiornate dehydrogenase (3-HPDH). Exogenous nucleic acid molecules can be part of one or more exogenous nucleic acid molecules (such as 1, 2 or 3 exogenous nucleic acid molecules). In some examples, exogenous nucleic acid molecules can be part of a vector, such as a plasmid or viral vector. In some examples, expression of the exogenous nucleic acid molecules is driven by one or more promoters, such as a constitutive or inducible promoter, or a bi-directional promoter. In some examples, the promoter used to drive expression of panD, BAPAT, and 3-HPDH is a native promoter (e.g., native to the panD, BAPAT, and 3-HPDH gene expressed). In other examples, the promoter used to drive expression of panD, BAPAT, and 3-HPDH is a non-native promoter (e.g., exogenous to the panD, BAPAT, and 3-HPDH gene expressed). In some examples, such a ΔcadA fungi expressing panD, BAPAT, and 3-HPDH are used to produce 3-HP.

A. Methods of Increasing aexA, panD, BAPAT, and/or 3-HPDH Expression

Methods of increasing native aexA expression in *Aspergillus* are provided. Similar methods can be used to increase expression of other genes, such as panD, BAPAT, and/or 3-HPDH nucleic acid sequences in an *Aspergillus* that does not have such sequences, or where increased expression is desired. In some examples, expression of aexA, panD, BAPAT, and/or 3-HPDH is increased by introducing aexA, panD, BAPAT, and/or 3-HPDH nucleic acid coding sequences (such may be codon optimized) into *Aspergillus*, such as *A. pseudoterreus, A. terreus*, or *A. niger*.

In some examples, expression of these genes is upregulated by introducing additional copies of aexA, panD, BAPAT, and/or 3-HPDH nucleic acid coding sequences (such may be codon optimized) into *Aspergillus* fungi. As used herein, "up-regulated" gene means that expression of the gene or gene product (e.g., protein) has been up-regulated, for example by introduction of additional copies of the appropriate gene or coding sequence into the fungus (or other molecular biology methods), such that the introduced nucleic acid sequence is expressed, resulting in increased expression or biological activity of the encoded gene product. In some embodiments, introduction of one or more transgenes including aexA, panD, BAPAT, and/or 3-HPDH coding sequences into *Aspergillus* increases expression of aexA, panD, BAPAT, and/or 3-HPDH by at least 20%, at least 40%, at least 50%, at least 100%, at least 150%, at least 200%, at least 300%, or at least 500%, for example relative to the parental *Aspergillus* strain without the introduced aexA, panD, BAPAT, and/or 3-HPDH coding sequences. The term "increased" or "up-regulated" as used herein with respect to a cell and a particular gene or protein activity refers to a higher level of activity than that measured in a comparable cell of the same species or strain. For example, a particular *Aspergillus* having increased or up-regulated aexA, panD, BAPAT, and/or 3-HPDH activity has increased panD, BAPAT, and/or 3-HPDH activity if a comparable *Aspergillus* having native aexA, panD, BAPAT, and/or 3-HPDH activity has less detectable aexA, panD, BAPAT, and/or 3-HPDH activity (for example as measured by gene or protein expression).

In one example, a strain of *Aspergillus* is transformed with a vector which has the effect of up-regulating a aexA, panD, BAPAT, and/or 3-HPDH gene (such as a native or non-native aexA, panD, BAPAT, and/or 3-HPDH gene). This can be done by introducing one or more aexA, panD, BAPAT, and/or 3-HPDH coding sequences (such as a gene sequence), whose expression is controlled by elements such as promoters and the like which control gene expression, by introducing a nucleic acid sequence which itself (or its encoded protein) can increase aexA, panD, BAPAT, and/or 3-HPDH protein activity in the fungus, or by introducing another molecule (such as a protein or antibody) increases aexA, panD, BAPAT, and/or 3-HPDH protein activity in the fungus. For example, a aexA, panD, BAPAT, and/or 3-HPDH gene can be up-regulated by introduction of a vector that includes one or more aexA, panD, BAPAT, and/or 3-HPDH coding sequences (such as 1, 2, 3, 4, 5, 6, 7, 8, 9 or 10 aexA, panD, BAPAT, and/or 3-HPDH sequences or copies of such sequences) into the desired fungus. In some examples, such aexA, panD, BAPAT, and/or 3-HPDH sequences are from different fungal species, can be multiple copies from a single species, or combinations thereof, such as aexA, panD, BAPAT, and/or 3-HPDH sequences from at least 2, 3, 4, 5, 6, 7, 8, 9, or 10 different fungal species. In some examples, the aexA, panD, BAPAT, and/or 3-HPDH sequence(s) introduced into the fungus is optimized for codon usage. Thus, the disclosure in some examples provides transformed fungi that include at least one exogenous nucleic acid molecule which includes a aexA, panD, BAPAT, and/or 3-HPDH gene or coding sequence (such as a nucleic acid sequence encoding SEQ ID NO: 2, 54, 56, or 58, respectively), for example in combination with ΔcadA. In one example, such transformed cells produce more AA, citric acid, or 3HP, for example relative to a comparable fungus with native aexA expression.

In one example, the cre-lox system is used for site specific recombination of DNA (for example see Steiger et al., *Appl. Environ. Microbiol.* 77(1):114, 2011). Using recombination techniques, a targeted gene of interest (e.g., cadA) can be deleted in the *Aspergillus* genome and replaced with one or more copies of an aexA, panD, BAPAT, and/or 3-HPDH sequence (for example in *A. terreus*, replacing one or both *A. terreus* cadA sequences with aexA, panD, BAPAT, and/or 3-HPDH sequences from *A. nidulans* or *A. flavus*) flanked by the lox sites. Transient expression (by electroporation of a suicide plasmid containing the cre gene under control of a promoter that functions in *Aspergillus*) of the cre recombinase should result in efficient elimination of the lox flanked marker. This process will produce a fungus containing the desired insertion mutation and one copy of the lox sequence.

In one example, a transgene is generated and expressed in the desired fungal cell, such as a native or ΔcadA fungal cell, to increase aexA, panD, BAPAT, and 3-HPDH expression. For example, one or more transgenes can include an aexA, panD, BAPAT, and 3-HPDH genomic or cDNA sequence (such as one having at least 80%, at least 85%, at least 90%, at least 95%, at least 96%, at least 97%, at least 98%, at least 99%, or 100% sequence identity to any panD, BAPAT, and 3-HPDH sequence provided herein), for example operably linked to one or more promoters, such as gpdA and enol. In one example, the promoter has at least 80%, at least 85%, at least 90%, at least 95%, at least 96%, at least 97%, at least 98%, at least 99%, or 100% sequence identity to SEQ ID NO: 32 and/or 33. In some examples, the transgene further includes a trpC transcriptional terminator sequence of *A. nidulans*, for example downstream of the panD, BAPAT, and/or 3-HPDH sequence. As an alternative to trpC, other transcriptional terminators can be used, such as promoters which include a transcriptional terminators (e.g., ArsA7, Arsa-37, polyubiquitin (ubi4)). In one example, the trpC transcriptional terminator has at least 80%, at least 85%, at least 90%, at least 95%, at least 96%, at least 97%, at least 98%, at least 99%, or 100% sequence identity to nt 5679-6465 of SEQ ID NO: 21. In one example, the trpC transcriptional terminator comprises or consists of nt 5679-6465 of SEQ ID NO: 21. In some examples, the transgene further includes a selection marker, such as a ptrA sequence, for example downstream of the trpC transcriptional terminator sequence. As an alternative to ptrA, the bleomycin gene or bar gene can be used. In one example, the ptrA sequence has at least 80%, at least 85%, at least 90%, at least 95%, at least 96%, at least 97%, at least 98%, or at least 99% sequence identity to nt 6466-8478 of SEQ ID NO: 21. In one example, the ptrA sequence comprises or consists of nt 6466-8478 of SEQ ID NO: 21.

In one example, the transgene used to increase expression of aexA in *Aspergillus* includes a sequence having at least 80%, at least 85%, at least 90%, at least 95%, at least 96%, at least 97%, at least 98%, at least 99%, or 100% sequence identity to SEQ ID NO: 1, SEQ ID NO: 21, nt 3933-5678 of SEQ ID NO: 21; nt 2952-5678 of SEQ ID NO: 21, nt 2952-6465 of SEQ ID NO: 21, nt 2952-8478 of SEQ ID NO: 21, nt 3933-6465 of SEQ ID NO: 21, or nt 3933-8478 of SEQ ID NO: 21. In one example, the transgene used to increase expression of aexA includes a sequence having at least 80%, at least 85%, at least 90%, at least 95%, at least 97%, at least 98%, at least 99%, or 100% sequence identity to SEQ ID NO: 30, 31, 32, and/or 33.

In one example, the vector used to increase expression of aexA in *Aspergillus* includes a sequence having at least 80%, at least 85%, at least 90%, at least 95%, at least 96%, at least 97%, at least 98%, at least 99%, or 100% sequence identity to SEQ ID NO: 1, SEQ ID NO: 21, nt 3933-5678 of SEQ ID NO: 21; nt 2952-5678 of SEQ ID NO: 21, nt 2952-6465 of SEQ ID NO: 21, nt 2952-8478 of SEQ ID NO: 21, nt 3933-6465 of SEQ ID NO: 21, or nt 3933-8478 of SEQ ID NO: 21. In one example, the vector used to increase expression of aexA includes a sequence having at least 80%, at least 85%, at least 90%, at least 95%, at least 97%, at least 98%, at least 99%, or 100% sequence identity to SEQ ID NO: 30, 31, 32, and/or 33.

In one example, the transgene used to express panD includes a sequence having at least 80%, at least 85%, at least 90%, at least 95%, at least 97%, at least 98%, at least 99%, or 100% sequence identity to SEQ ID NO: 12, 14, 30, 31, 32, and/or 33. In one example, the transgene comprises or consists of the sequence shown in SEQ ID NO: 12, 14, 30, 31, 32, and/or 33.

In one example, the transgene used to express BAPAT includes a sequence having at least 80%, at least 85%, at least 90%, at least 95%, at least 97%, at least 98%, at least 99%, or 100% sequence identity to SEQ ID NO: 15, 17, 30, 31, 32, and/or 33. In one example, the transgene comprises or consists of the sequence shown in SEQ ID NO: 15, 17, 30, 31, 32, and/or 33.

In one example, the transgene used to express 3-HPDH includes a sequence having at least 80%, at least 85%, at least 90%, at least 95%, at least 97%, at least 98%, at least 99%, or 100% sequence identity to SEQ ID NO: 18, 20, 30, 31, 32, and/or 33. In one example, the transgene comprises or consists of the sequence shown in SEQ ID NO: 18, 20, 30, 31, 32, and/or 33.

B. aexA Sequences aexA protein and nucleic acid sequences are publicly available and specific examples are provided herein. In addition, aexA sequences can be identified using molecular biology methods and using publicly available databases.

An exemplary aexA nucleic acid sequence is shown in SEQ ID NO: 1. However, the disclosure also encompasses variants of SEQ ID NO: 1 which encode a functional aexA protein. One skilled in the art will understand variants of the aexA nucleic acid sequences provided herein can be overexpressed. Variant sequences may contain a single insertion, a single deletion, a single substitution, multiple insertions, multiple deletions, multiple substitutions, or any combination thereof (e.g., single deletion together with multiple insertions). In addition, the degeneracy of the code permits multiple nucleic acid sequences to encode the same protein. Such variant aexA nucleic acid molecules can share at least 60%, at least 70%, at least 80%, at least 85%, at least 90%, at least 95%, at least 96%, at least 97%, at least 98%, or at least 99% sequence identity to any aexA nucleic acid sequence, such as SEQ ID NO: 1.

Examples of aexA protein sequences are shown in SEQ ID NOS: 2, 3, 4 and 5. However, the disclosure also encompasses variants SEQ ID NOS: 2, 3, 4 and 5 which retain aexA activity. One skilled in the art will understand that variants of these aexA sequences can be overexpressed. Variant sequences can be identified, for example by aligning known aexA sequences (e.g., see FIG. 5). Variant sequences may contain a single insertion, a single deletion, a single substitution, multiple insertions, multiple deletions, multiple substitutions, or any combination thereof (e.g., single deletion together with multiple insertions). Such aexA proteins share at least 60%, at least 65%, at least 69%, at least 70%, at least 71%, at least 75%, at least 80%, at least 85%, at least 90%, at least 95%, at least 96%, at least 97%, at least 98%, or at least 99% sequence identity to a aexA protein sequence, such as SEQ ID NO: 2, 3, 4 and 5.

In some examples, an aexA sequence that is to be overexpressed encodes or includes one or more conservative amino acid substitutions. A conservative amino acid substitution is a substitution of one amino acid (such as one found in a native sequence) for another amino acid having similar biochemical properties. Typically, conservative substitutions have little to no impact on the activity of a resulting peptide. In one example, an aexA protein sequence (such as SEQ ID NO: 2, 3, 4, or 5) includes one or more amino acid substitutions, such as conservative substitutions (for example at 1, 2, 5 or 10 residues). Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val. Further information about conservative substitutions can be found in, among other locations in, Ben-Bassat et al., (*J. Bacteriol.* 169:751-7, 1987), O'Regan et al., (*Gene* 77:237-51, 1989), Sahin-Toth et al., (*Protein Sci.* 3:240-7, 1994), Hochuli et al., (*Bio/Technology* 6:1321-5, 1988), WO 00/67796 (Curd et al.) and in standard textbooks of genetics and molecular biology.

The aexA gene overexpressed in a fungus, in particular examples, includes a sequence that encodes an aexA protein having at least 60%, at least 65%, at least 69%, at least 70%, at least 71%, at least 75%, at least 80%, at least 85%, at least 90%, at least 95%, at least 96%, at least 97%, at least 98%, at least 99%, or 100% sequence identity to a aexA protein sequence, such as SEQ ID NO: 2, 3, 4 and 5, wherein the protein can export aconitic acid from a cell. In a specific example, the aexA gene inactivated in a fungus encodes an aexA protein shown in SEQ ID NO: 2, 3, 4 and 5.

The aexA gene that is to be overexpressed in a fungus, in particular examples, includes a sequence (such as a coding sequence) having at least 60%, at least 65%, at least 69%, at least 70%, at least 71%, at least 75%, at least 80%, at least 85%, at least 90%, at least 95%, at least 96%, at least 97%, at least 98%, at least 99%, or 100% sequence identity to a aexA nucleic acid sequence, such as SEQ ID NO: 1, and encodes an aexA protein that can export aconitic acid from a cell. In a specific example, the aexA gene overexpressed in a fungus is the sequence of SEQ ID NO: 1.

One skilled in the art will appreciate that additional aexA sequences can be identified. For example, aexA nucleic acid molecules that encode an aexA protein can be identified and obtained using molecular cloning or chemical nucleic acid synthesis procedures and techniques, including PCR. In addition, nucleic acid sequencing techniques and software programs that translate nucleic acid sequences into amino acid sequences based on the genetic code can be used to determine whether or not a particular nucleic acid has any sequence homology with known aexA sequences. Sequence alignment software such as MEGALIGN (DNASTAR, Madison, WI, 1997) can be used to compare various sequences.

In addition, nucleic acid hybridization techniques can be used to identify and obtain a nucleic acid molecule that encodes an aexA protein. Briefly, any known aexA nucleic acid molecule (e.g., SEQ ID NO: 1), or fragment thereof, can be used as a probe to identify similar nucleic acid molecules by hybridization under conditions of moderate to high stringency. Such similar nucleic acid molecules then can be isolated, sequenced, and analyzed to determine whether the encoded protein is an aexA protein.

C. Methods of Functionally Deleting cadA

As used herein, an "inactivated" or "functionally deleted" cadA gene means that the cadA gene has been mutated, for example by insertion, deletion, or substitution (or combinations thereof) of one or more nucleotides such that the mutation substantially reduces (and in some cases abolishes) expression or biological activity of the encoded cadA gene product. The mutation can act through affecting transcription or translation of the cadA gene or its mRNA, or the mutation can affect the cadA polypeptide product itself in such a way as to render it substantially inactive.

In one example, a strain of *Aspergillus* (such as one that is aexA+) is transformed with a vector which has the effect of down-regulating or otherwise inactivating a cadA gene. This can be done by mutating control elements such as promoters and the like which control gene expression, by mutating the coding region of the gene so that any protein expressed is substantially inactive, or by deleting the cadA gene entirely. For example, a cadA gene can be functionally deleted by complete or partial deletion mutation (for example by deleting a portion of the coding region of the gene) or by insertional mutation (for example by inserting a sequence of nucleotides into the coding region of the gene, such as a sequence of about 1-5000 nucleotides). In one example, the cadA gene is genetically inactivated by inserting coding sequences for aexA, panD, BAPAT, and/or 3-HPDH. Thus, the disclosure provides transformed fungi that include at least one exogenous nucleic acid molecule which genetically inactivates an endogenous cadA gene. In one example, aexA+/ΔcadA cell produces more aconitic acid, for example relative to a comparable fungus with native or wild-type aexA expression.

In particular examples, an insertional mutation includes introduction of a sequence that is in multiples of three bases (e.g., a sequence of 3, 9, 12, or 15 nucleotides) to reduce the possibility that the insertion will be polar on downstream genes. For example, insertion or deletion of even a single nucleotide that causes a frame shift in the open reading frame, which in turn can cause premature termination of the encoded cadA polypeptide or expression of a substantially inactive polypeptide. Mutations can also be generated through insertion of foreign gene sequences, for example the insertion of a gene encoding antibiotic resistance (such as hygromycin or bleomycin), or aexA, panD, BAPAT, and/or 3-HPDH coding sequences.

In one example, genetic inactivation is achieved by deletion of a portion of the coding region of an endogenous cadA gene. For example, some, most (such as at least 50%) or virtually the entire endogenous coding region can be deleted. In particular examples, about 5% to about 100% of the endogenous gene is deleted, such as at least 20% of the gene, at least 40% of the gene, at least 75% of the gene, or at least 90% of the endogenous cadA gene.

Deletion mutants can be constructed using any of a number of techniques. In one example, homologous double crossover with fusion PCR products is employed to genetically inactivate cadA in *Aspergillus*.

In one example, counterselectable markers are employed to delete genes (see Reyrat et al., *Infec. Immun.* 66:4011-4017, 1998). In this technique, a double selection strategy is employed wherein a plasmid is constructed encoding both a selectable and counterselectable marker, with flanking DNA sequences derived from both sides of the desired deletion. The selectable marker is used to select for fungi in which the plasmid has integrated into the genome in the appropriate location and manner. The counterselecteable marker is used to select for the very small percentage of fungi that have spontaneously eliminated the integrated plasmid. A fraction of these fungi will then contain only the desired deletion with no other foreign DNA present.

In another technique, the cre-lox system is used for site specific recombination of DNA (for example see Steiger et al., *Appl. Environ. Microbiol.* 77(1):114, 2011). The system includes 34 base pair lox sequences that are recognized by the bacterial cre recombinase gene. If the lox sites are present in the DNA in an appropriate orientation, DNA flanked by the lox sites will be excised by the cre recombinase, resulting in the deletion of all sequences except for one remaining copy of the lox sequence. Using standard recombination techniques, the targeted gene of interest (e.g., cadA) can be deleted in the *Aspergillus* genome and to replace it with a selectable marker (for example a gene coding for kanamycin resistance) that is flanked by the lox sites. Transient expression (by electroporation of a suicide plasmid containing the cre gene under control of a promoter that functions in *Aspergillus*) of the cre recombinase should result in efficient elimination of the lox flanked marker. This process will produce a mutant containing the desired deletion mutation and one copy of the lox sequence.

In another method, an endogenous cadA gene sequence in the *Aspergillus* genome is replaced with a marker gene, such as green fluorescent protein, (3-galactosidase, or luciferase. In this technique, DNA segments flanking a desired deletion are prepared by PCR and cloned into a suicide (non-replicating) vector for *Aspergillus*. An expression cassette, containing a promoter active in *Aspergillus* and the appropriate marker gene, is cloned between the flanking sequences. The plasmid is introduced into wild-type *Aspergillus*. Fungi that incorporate and express the marker gene are isolated and examined for the appropriate recombination event (replacement of the wild type cadA gene with the marker gene).

Thus, for example, a fungal cell can be engineered to have a disrupted cadA gene using mutagenesis or knock-out technology. (Methods in Yeast Genetics (1997 edition), Adams, Gottschling, Kaiser, and Sterns, Cold Spring Harbor Press, 1998; Datsenko and Wanner, *Proc. Natl. Acad. Sci. USA* 97: 6640-5, 2000; and Dai et al., *Appl. Environ. Microbiol.* 70(4):2474-85, 2004). Alternatively, antisense technology can be used to reduce or eliminate the activity of cadA. For example, a fungal cell can be engineered to contain a cDNA that encodes an antisense molecule that prevents cadA from being translated. The term "antisense molecule" encompasses any nucleic acid molecule or nucleic acid analog (e.g., peptide nucleic acids) that contains a sequence that corresponds to the coding strand of an endogenous cadA gene. An antisense molecule also can have flanking sequences (e.g., regulatory sequences). Thus, antisense molecules can be ribozymes or antisense oligonucleotides. A ribozyme can have any general structure including, without limitation, hairpin, hammerhead, or axehead structures, provided the molecule cleaves RNA. Further, gene silencing can be used to reduce the activity of cadA.

In one example, to genetically inactivate cadA in *A. pseudoterreus* or *A. terreus*, protoplast transformation is used, for example as described in Example 1. For example, conidia of *Aspergillus* are grown in liquid complete medium at room temperature (e.g., about 20-35° C., such as 30° C.) and grown for at least 12 hours (such as at least 16 hours, or at least 18 hours, such as 12-24 hours, or 16-18 hours), at least 100 rpm, such as at least 150 rpm, at least 200 rpm for example 100 to 200 rpm. The resulting mycelia are subsequently harvested, for example by filtration. Protoplasts are prepared, for example by treating the harvested mycelia with a lysing enzyme (for example in an osmotic wash buffer for at least 30 min, at least 60 min, at least 120 min, or at least 240 min, such as 2 h). The resulting protoplasts are collected (e.g., by filtering). Protoplasts can be washed, for example with a Washing Solution (0.6M KCl, 0.1M Tris/HCl, pH 7.0) and Conditioning Solution (0.6M KCl, 50 mM CaCl$_2$, 10 mM Tris/HCl, pH 7.5). The protoplasts are transformed, for example in the conditioning solution. In some examples, at least 0.5 ug, at least 1 ug, or at least 2 ug of DNA (such as 1-2 ug DNA) is added to at least $10^6$ protoplasts (such as at least $10^7$ or $2 \times 10^7$ protoplasts). Polyethylene glycol (PEG), such as PEG8000 is added (such as 25% PEG8000, 0.6M KCl, 50 mM CaCl$_2$, 10 mM Tris/HCl, and pH 7.5) and the reaction incubated for at least 5 min (such as at least 10 min, at least 20 min, or at least 30 min, such as 10-30 min, 15-20 min, or 20 min) on ice. Additional PEG solution can be added and the reaction incubated for at least 1 min, at least 3 min, or at least 5 min, on ice. Conditioning Solution is added to the reaction, and the protoplast suspension mixed with warm selection agar (Minimal media+0.6M KCl+1.5% Agar+100 ug/ml hygromycin) (such as at 50° C.), and poured directly onto petri dish plates and allowed to solidify.

Solidified plates can be inverted and incubated overnight at room temperature (e.g., about 20-35° C., such as 30° C.). The following day, the plates can be overlaid with Minimal Medium containing a selection antibiotic, such as hygromycin. Colonies appear after 3-4 days. Transformants can be excised and transferred to MM plate containing the selection antibiotic.

D. Measuring cadA Gene Inactivation

A fungus having an inactivated endogenous cadA gene can be identified using known methods. For example, PCR and nucleic acid hybridization techniques, such as Northern and Southern analysis, can be used to confirm that a fungus has a genetically inactivated cadA gene. In one example, real-time reverse transcription PCR (qRT-PCR) is used for detection and quantification of targeted messenger RNA, such as mRNA of cadA gene in the parent and mutant strains as grown at the same culture conditions. Immunohistochemical and biochemical techniques can also be used to determine if a cell expresses cadA by detecting the expression of the cadA peptide encoded by cadA. For example, an antibody having specificity for cadA can be used to determine whether or not a particular fungus contains a functional nucleic acid encoding cadA protein. Further, biochemical techniques can be used to determine if a cell contains a cadA gene inactivation by detecting a product produced as a result of the lack of expression of the peptide. For example, production of aconitic acid by *A. terreus* or *A. pseudoterreus* can indicate that such a fungus contains an inactivated cadA gene.

E. Measuring Aconitic Acid Production

Methods of determining whether a overexpression of aexA and/or genetic inactivation of cadA in *Aspergillus*, such as *A. terreus* or *A. pseudoterreus*, increases aconitic acid production, for example relative to the same strain of *A. terreus* or *A. pseudoterreus* with native aexA expression and/or a native cadA sequence (such as a parental strain), are provided herein. Although particular examples are disclosed herein, the methods are not limiting.

For example, production of aconitic acid by *Aspergillus* (such as an aexA+ or aexA+/ΔcadA strain) can be measured using a spectrophotometric assay, by liquid chromatography (LC), or high-pressure liquid chromatography (HPLC) methods. In some examples, the supernatant of the fungus is analyzed for the presence of aconitic acid. In some examples, the culture media containing the aexA+ or aexA+/ΔcadA strain is filtered prior to measuring aconitic acid in the culture media (supernatant).

F. cadA Sequences cadA protein and nucleic acid sequences are publicly available and specific examples are provided herein. In addition, cadA sequences can be identified using molecular biology methods.

Examples of cadA nucleic acid sequences are shown in SEQ ID NOS: 6, 8, 10 and 11. However, the disclosure also encompasses variants of SEQ ID NOS: 6, 8, 10 and 11 which encode a functional cadA protein. One skilled in the art will understand variants of the cadA nucleic acid sequences provided herein can be genetically inactivated. Variant sequences may contain a single insertion, a single deletion, a single substitution, multiple insertions, multiple deletions, multiple substitutions, or any combination thereof (e.g., single deletion together with multiple insertions). In addition, the degeneracy of the code permits multiple nucleic acid sequences to encode the same protein. Such variant cadA nucleic acid molecules can share at least 60%, at least 70%, at least 80%, at least 85%, at least 90%, at least 95%, at least 96%, at least 97%, at least 98%, or at least 99% sequence identity to any cadA nucleic acid sequence, such as SEQ ID NO: 6, 8, 10 or 11.

Examples of cadA protein sequences are shown in SEQ ID NOS: 7 and 9. However, the disclosure also encompasses variants SEQ ID NOS: 7 and 9 which retain cadA activity. One skilled in the art will understand that variants of these cadA enzyme sequences can be inactivated. Variant sequences can be identified, for example by aligning known cadA sequences. Variant sequences may contain a single insertion, a single deletion, a single substitution, multiple insertions, multiple deletions, multiple substitutions, or any combination thereof (e.g., single deletion together with multiple insertions). Such cadA peptides share at least 80%, at least 85%, at least 90%, at least 95%, at least 97%, at least 98%, or at least 99% sequence identity to a cadA protein sequence, such as SEQ ID NO: 7 or 9.

In some examples, a cadA sequence that is to be genetically inactivated encodes or includes one or more conservative amino acid substitutions. In one example, a cadA protein sequence (such as SEQ ID NO: 7 or 9) includes one or more amino acid substitutions, such as conservative substitutions (for example at 1, 2, 5 or 10 residues). Examples of amino acids which may be substituted for an original amino acid in a protein and which are regarded as conservative substitutions are provided above.

The cadA gene inactivated in a fungus, in particular examples, includes a sequence that encodes a cadA protein having at least 60%, at least 70% at least 80%, at least 85%, at least 90%, at least 95%, at least 96%, at least 97%, at least 98%, at least 99%, or 100% sequence identity to a cadA protein sequence, such as SEQ ID NO: 7 or 9, wherein the protein can catalyze the decarboxylation of cis-aconitate to itaconate and $CO_2$ and vice versa. In a specific example, the cadA gene prior to its inactivation encoded a cadA protein shown in SEQ ID NO: 7 or 9.

The cadA gene that is to be inactivated in a fungus, in particular examples, includes a sequence (such as a coding sequence) having at least 60%, at least 70%, at least 80%, at least 85%, at least 90%, at least 95%, at least 97%, at least 98%, at least 99%, or 100% sequence identity to a cadA nucleic acid sequence, such as SEQ ID NO: 6, 8, 10, or 11, and encodes a cadA protein that can catalyze the decarboxylation of cis-aconitate to itaconate and $CO_2$ and vice versa. In a specific example, the cadA gene inactivated in a fungus is the sequence of SEQ ID NO: 6 or 8.

One skilled in the art will appreciate that additional cadA sequences can be identified. For example, cadA nucleic acid molecules that encode a cadA protein can be identified and obtained using molecular cloning or chemical nucleic acid synthesis procedures and techniques, including PCR. In addition, nucleic acid sequencing techniques and software programs that translate nucleic acid sequences into amino acid sequences based on the genetic code can be used to determine whether or not a particular nucleic acid has any sequence homology with known cadA sequences. Sequence alignment software such as MEGALIGN (DNASTAR, Madison, WI, 1997) can be used to compare various sequences.

In addition, nucleic acid hybridization techniques can be used to identify and obtain a nucleic acid molecule that encodes a cadA protein. Briefly, any known cadA nucleic acid molecule (such as SEQ ID NO: 6, 8, 10, or 11), or fragment thereof, can be used as a probe to identify similar nucleic acid molecules by hybridization under conditions of moderate to high stringency. Such similar nucleic acid molecules then can be isolated, sequenced, and analyzed to determine whether the encoded protein is a cadA protein.

G. panD, BAPAT, and 3-HPDH Sequences panD, BAPAT, and 3-HPDH protein and nucleic acid sequences are publicly available and specific examples are provided herein. In addition, panD, BAPAT, and 3-HPDH sequences can be identified using molecular biology methods.

Exemplary of panD coding sequences are shown in SEQ ID NO: 12 and 14. However, the disclosure also encompasses variants of SEQ ID NO: 12 and 14 which encode a functional panD protein. Exemplary of BAPAT coding sequences are shown in SEQ ID NO: 15 and 17. However, the disclosure also encompasses variants of SEQ ID NO: 15 and 17 which encode a functional BAPAT protein. Exemplary of 3-HPDH coding sequences are shown in SEQ ID NO: 18 and 20. However, the disclosure also encompasses variants of SEQ ID NO: 18 and 20 which encode a functional 3-HPDH protein.

One skilled in the art will understand variants of the panD, BAPAT, and 3-HPDH nucleic acid sequences provided herein can be introduced into (or be endogenous to) an *Aspergillus* fungus, such as a aexA+ or aexA+/ΔcadA *Aspergillus*, such as inserting panD, BAPAT, and 3-HPDH expression sequences into the native cadA gene to inactivate it. Variant panD, BAPAT, and 3-HPDH sequences may contain a single insertion, a single deletion, a single substitution, multiple insertions, multiple deletions, multiple substitutions, or any combination thereof (e.g., single deletion together with multiple insertions). In addition, the degeneracy of the code permits multiple nucleic acid sequences to encode the same protein. In some examples, a panD, BAPAT, and 3-HPDH sequence expressed in an *Aspergillus* fungus is codon optimized for expression in *Aspergillus*, such as *Aspergillus terreus* or *pseudoterreus*. Such variant panD, BAPAT, and 3-HPDH nucleic acid molecules in some examples share at least 60%, at least 70%, at least 75%, at least 80%, at least 85%, at least 90%, at least 95%, at least 96%, at least 97%, at least 98%, at least 99%, or 100% sequence identity to any panD, BAPAT, and 3-HPDH nucleic acid sequence, such as SEQ ID NO: 12, 15, or 18, respectively, or SEQ ID NO: 14, 17, or 20, respectively.

Exemplary panD, BAPAT, and 3-HPDH protein sequences are shown in SEQ ID NOS: 13, 16, and 19, respectively. However, the disclosure also encompasses variants SEQ ID NOS: 13, 16, and 19 which retain panD, BAPAT, and 3-HPDH activity, respectively. One skilled in the art will understand that variants of these panD, BAPAT, and 3-HPDH sequences can be expressed in an *Aspergillus* fungus, such as aexA+ or aexA+/ΔcadA *Aspergillus*, Variant sequences can be identified, for example by aligning known panD, BAPAT, and 3-HPDH sequences. Variant sequences may contain a single insertion, a single deletion, a single substitution, multiple insertions, multiple deletions, multiple substitutions, or any combination thereof (e.g., single deletion together with multiple insertions). Such panD, BAPAT, and 3-HPDH peptides expressed in a aexA+ or aexA+/ΔcadA *Aspergillus* in some examples share at least 60%, at least 70%, at least 75%, at least 80%, at least 85%, at least 90%, at least 95%, at least 96%, at least 97%, at least 98%, at least 99%, or 100% sequence identity to a panD, BAPAT, and 3-HPDH protein sequence, such as SEQ ID NO: 13, 16, or 19, respectively.

In some examples, a panD, BAPAT, and 3-HPDH sequence that is to be expressed in an aexA+ or aexA+/ΔcadA *Aspergillus* fungus encodes or includes one or more conservative amino acid substitutions. In one example, a panD, BAPAT, or 3-HPDH sequence (such as SEQ ID NO: 13, 16, and 19, respectively) includes one or more amino acid substitutions, such as conservative substitutions (for example at 1, 2, 5, or 10 residues). Examples of conservative substitutions are provided above.

The panD, BAPAT, and 3-HPDH gene expressed in a aexA+ or aexA+/ΔcadA fungus, in particular examples, includes a sequence that encodes a panD, BAPAT, and 3-HPDH protein having at least 60%, at least 70%, at least 75%, at least 80%, at least 85%, at least 90%, at least 95%, at least 96%, at least 97%, at least 98%, at least 99%, or 100% sequence identity to a panD, BAPAT, and 3-HPDH protein sequence, such as SEQ ID NO: 13, 16, and 19, respectively, wherein the variant protein has the biological activity of panD, BAPAT, or 3-HPDH, respectively. In a specific example, the panD, BAPAT, and 3-HPDH gene expressed in an aexA+ or aexA+/ΔcadA fungus encodes the protein shown in SEQ ID NO: 13, 16, or 19, respectively.

One skilled in the art will appreciate that additional panD, BAPAT, and 3-HPDH sequences can be identified. For example, panD, BAPAT, and 3-HPDH nucleic acid molecules that encode a panD, BAPAT, and 3-HPDH protein, respectively can be identified and obtained using molecular cloning or chemical nucleic acid synthesis procedures and techniques, including PCR. In addition, nucleic acid sequencing techniques and software programs that translate nucleic acid sequences into amino acid sequences based on the genetic code can be used to determine whether or not a particular nucleic acid has any sequence homology with panD, BAPAT, or 3-HPDH sequences. Sequence alignment software such as MEGALIGN (DNASTAR, Madison, WI, 1997) can be used to compare various sequences.

In addition, nucleic acid hybridization techniques can be used to identify and obtain a nucleic acid molecule that encodes a panD, BAPAT, or 3-HPDH protein. Briefly, any known panD, BAPAT, or 3-HPDH nucleic acid molecule, or fragment thereof, can be used as a probe to identify similar nucleic acid molecules by hybridization under conditions of moderate to high stringency. Such similar nucleic acid molecules then can be isolated, sequenced, and analyzed to determine whether the encoded protein is a panD, BAPAT, or 3-HPDH protein.

In one example, exogenous panD, BAPAT, and/or 3-HPDH nucleic acid sequences are introduced into *Aspergillus* using protoplast transformation, for example as described in Example 1 (and described above).

H. Measuring Gene Expression

An aexA+ or aexA+/ΔcadA fungus expressing aexA, panD, BAPAT, and/or 3-HPDH can be identified using known methods. For example, PCR and nucleic acid hybridization techniques, such as Northern, RT-PCR, and Southern analysis, can be used to confirm that a fungus expresses (such as overexpresses) aexA, panD, BAPAT, and/or 3-HPDH such as an increase in the aexA, panD, BAPAT, and/or 3-HPDH copy number. Immunohisto-chemical and biochemical techniques can also be used to determine if a cell expresses or overexpresses aexA, panD, BAPAT, and/or 3-HPDH by detecting the expression of the aexA, panD, BAPAT, and/or 3-HPDH peptide encoded by aexA, panD, BAPAT, and/or 3-HPDH, respectively. For example, an antibody having specificity for aexA, panD, BAPAT, and/or 3-HPDH can be used to determine whether or not a particular fungus has increased aexA, panD, BAPAT, and/or 3-HPDH protein expression, respectively. Further, biochemical techniques can be used to determine if a cell has increased aexA, panD, BAPAT, and/or 3-HPDH expression by detecting a product produced as a result of the expression of the peptide. For example, production of 3-HP by aexA+ or aexA+/ΔcadA *Aspergillus* can indicate that such a fungus expresses or overexpresses aexA, panD, BAPAT, and 3-HPDH.

I. Measuring 3-HP Production

Methods of determining whether an aexA+ or aexA+/ΔcadA fungus that also expresses panD, BAPAT, and 3-HPDH has increased 3-HP production, for example relative to the same strain with a native aexA sequence, (such as a parental strain) include HPLC.

Methods of Producing Aconitic Acid (AA)

The recombinant *Aspergillus* fungi provided herein (aexA+ or aexA+/ΔcadA), can be used to produce AA (for example for as a building block for other materials, such as polymers). Such fungi can be from any *Aspergillus* species, such as *Aspergillus terreus* or *pseudoterreus*. For example, the disclosure provides methods of making AA (such as cis-aconitic acid, trans-aconitic acid, or both), which can include culturing the disclosed fungi under conditions that permit the fungus to make AA, for example in Riscaldati medium.

In some examples, the aexA+ or aexA+/ΔcadA fungi are cultured at room temperature (e.g., 20-35° C., such as about 30° C.) at normal atmospheric pressure (e.g., 1 atm). In some examples, the method includes purifying or isolating the AA, for example from the culture media or from the cultured fungus. In some examples, the AA is isolated at least 2 days, at least 3 days, at least 5 days, at least 7 days, at least 8 days or at least 10 days after the start of culturing, such as 2, 3, 4, 5, 6, 7, 8, 9, 10, 11, 12, 13, 14, 15, 16, 17, 18, 19 or 20 days after the start of culturing.

Methods of making AA include culturing the aexA+ or aexA+/ΔcadA *Aspergillus* provided herein t, under conditions that permit the fungus to make AA. In general, the culture media and/or culture conditions can be such that the fungi grow to an adequate density and produce AA efficiently. In one example the ΔcadA fungi are cultured or grown in an acidic liquid medium, such as Riscaldati medium (100 g Glucose, 0.11 g $KH_2PO_4$, 2.36 g $(NH_4)_2SO_4$, 2.08 g $MgSO_4*7H_2O$, 0.074 g NaCl, 0.13 g $CaCl_2*2H_2O$, 1 ml of 1000× trace elements in 1000 ml DI water, adjust pH to 3.4 with $H_2SO_4$, 1000× trace elements contains 1.3 g/L $ZnSO_4*7H_2O$, 5.5 g/L $FeSO_4*7H_2O$, 0.2 g/L $CuSO_4*5H_2O$, 0.7 g/L $MnCl_2*4H_2O$). In one example the aexA+ or aexA+/ΔcadA *Aspergillus* fungi provided herein are cultured or grown in a liquid medium having an initial pH of less than 4, such as less than 3.5, for example about pH 3 to 4, 3.5 to 4, 3.3 to 3.5, for example pH 2.8, 2.9, 3, 3.1, 3.2, 3.3, 3.4, 3.5, 3.6, 3.7, 3.8, 3.9 or 4. In some examples the aexA+ or aexA+/ΔcadA *Aspergillus* fungi are cultured or grown in a liquid Riscaldati medium at about 20 to 35° C. (such as 20° C. to 30° C., 25° C. to 30° C., 28 to 32° C., or 30° C.) with rotation (such as at least 100 rpm, at least 120 rpm, at least 150 rpm, at least 170 rpm, or at least 200 rpm, such as 200 rpm) at normal pressure.

In one example, the aexA+ or aexA+/ΔcadA fungi are grown in culture containers (such as baffled flasks, and in some examples are silanized (5% solution of dichlorodimethylsilane in heptane (Sigma, St. Louis, MO)). Each culture container is inoculated with spores (such as at least $2 \times 10^6$ spores/ml) and incubated for at least 3 days, at least 4 days, at least 5 days, at least 7 days, or at least 10 days at 30° C. and 100 to 250 rpm to obtain AA.

In one example, the aexA+ or aexA+/ΔcadA *Aspergillus*, produce more AA than a corresponding fungus with wild-type or native levels of aexA (and in some examples also native levels of cadA). In specific examples, the disclosed fungi produce at least 20 g/l of total AA after 7 days, for example at least 25 g/l, at least 30 g/l, at least 40 g/l, at least 45 g/l, at least 46 g/l, at least 47 g/l, at least 48 g/l, at least 49 g/l or at least 50 g/l after at least 7 days, at least 8 days, or at least 10 days, such as after 5 to 8 days, 5 to 10 days, or 6 to 7 days) when grown in Riscaldati medium at 30° C. with 200 rpm shaking. In specific examples, the aexA+ or aexA+/ΔcadA fungi yield at least 0.5 g/g of total AA after 7 days, for example at least 0.6 g/g or at least 0.7 g/g after at least 7 days, at least 8 days, or at least 10 days, such as after 5 to 8 days, 5 to 10 days, or 6 to 7 days when grown in Riscaldati medium at 30° C. with 200 rpm shaking. In specific examples, the aexA+ or aexA+/ΔcadA fungi produce AA at a rate of at least 0.1 g/L/hr after at least 7 days, for example at least 0.2 g/L/hr, at least 0.25 g/L/hr, or at least 0.3 g/L/hr, after at least 7 days, at least 8 days, or at least 10 days, such as after 5 to 8 days, 5 to 10 days, or 6 to 7 days) when grown in Riscaldati medium at 30° C. with 200 rpm shaking.

In some examples, the method further includes isolating the AA made by the aexA+ or aexA+/ΔcadA *Aspergillus*. Once produced, any method can be used to isolate the AA. For example, separation techniques (such as filtration) can be used to remove the fungal biomass from the culture medium, and isolation procedures (e.g., filtration, distillation, precipitation, electrodialysis, and ion-exchange procedures) can be used to obtain the AA from the broth (such as a fungi-free broth). In addition, the AA can be isolated from the culture medium after the AA production phase has been terminated.

Methods of Producing 3-HP

The aexA+ or aexA+/ΔcadA *Aspergillus*), can further express endogenous or exogenous panD, BAPAT, and 3-HPDH, and thus be used to produce 3-HP

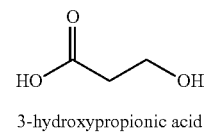

3-hydroxypropionic acid (for example for as a building block for other materials, such as acrylonitrile, acrylic acid by dehydration, malonic acid by oxidation, esters by esterification reactions with alcohols, and reduction to 1,3 propanediol). Such fungi can be from any *Aspergillus* species, such as *Aspergillus terreus, Aspergillus niger*, or *Aspergillus pseudoterreus*. For example, the disclosure provides methods of making 3-HP, which can include culturing the disclosed fungi that also express panD, BAPAT, and 3-HPDH under conditions that permit the fungus to make 3-HP, for example in Riscaldati medium (such as modified Riscaldati medium with 20× trace elements).

In some examples, the aexA+ or aexA+/ΔcadA *Aspergillus* provided herein, and further express endogenous or exogenous panD, BAPAT, and 3-HPDH, are cultured at room temperature (e.g., 20-35° C.) at normal atmospheric pressure (e.g., 1 atm). In some examples, the method includes purifying or isolating the 3-HP, for example from the culture media or from the cultured fungus. In some examples, the 3-HP is isolated at least 2 days, at least 3 days, at least 5 days, at least 7 days, at least 8 days or at least 10 days after the start of culturing, such as 2, 3, 4, 5, 6, 7, 8, 9, 10, 11, 12, 13, 14, 15, 16, 17, 18, 19 or 20 days after the start of culturing.

Methods of making 3-HP include culturing aexA+ or aexA+/ΔcadA *Aspergillus* fungi provided herein, and further express endogenous or exogenous panD, BAPAT, and 3-HPDH, under conditions that permit the fungus to make 3-HP. In general, the culture media and/or culture conditions can be such that the fungi grow to an adequate density and produce 3-HP efficiently. In one example the aexA+ or aexA+/ΔcadA fungi that further express panD, BAPAT, and 3-HPDH are cultured or grown in an acidic liquid medium, such as Riscaldati medium (100 g Glucose, 0.11 g $KH_2PO_4$, 2.36 g $(NH_4)_2SO_4$, 2.08 g $MgSO_4*7H_2O$, 0.074 g NaCl, 0.13 g $CaCl_2*2H_2O$, 1 ml of 1000× trace elements in 1000 ml DI water, adjust pH to 3.4 with $H_2SO_4$, 1000× trace elements contains 1.3 g/L $ZnSO_4*7H_2O$, 5.5 g/L $FeSO_4*7H_2O$, 0.2 g/L $CuSO_4*5H_2O$, 0.7 g/L $MnCl_2*4H_2O$, which may include 20× trace elements). In one example such fungi are cultured or grown in a liquid medium having an initial pH of less than 4, such as less than 3.5, for example about pH 3 to 4, 3.5 to 4, 3.3 to 3.5, for example pH 2.8, 2.9, 3, 3.1, 3.2, 3.3, 3.4, 3.5, 3.6, 3.7, 3.8, 3.9 or 4. In some examples the aexA+ or aexA+/ΔcadA fungi that also express panD, BAPAT, and 3-HPDH are cultured or grown in a liquid modified Riscaldati medium with 20× trace elements at about 20 to 35° C. (such as 20° C. to 30° C., 25° C. to 30° C., 28 to 32° C., or 30° C.) with rotation (such as at least 100 rpm, at least 120 rpm, such as 150 or 200 rpm) at normal pressure.

In one example, the aexA+ or aexA+/ΔcadA fungi are grown in culture containers (such as baffled flasks, and in some examples are silanized (5% solution of dichlorodimethylsilane in heptane (Sigma, St. Louis, MO)). Each culture container is inoculated with spores (such as at least $10^6$ spores/ml) and incubated for at least 3 days, at least 4 days, at least 5 days, or at least 10 days at 30° C. and 100 to 300 rpm (such as 150 or 200 rpm) to obtain 3-HP.

In one example, the aexA+ or aexA+/ΔcadA *Aspergillus* can further express endogenous or exogenous panD, BAPAT, and 3-HPDH produce more 3-HP than a corresponding fungus with wild-type levels of axeA (and in some examples wild-type levels of cadA), either with or without panD, BAPAT, and 3-HPDH expression. In specific examples, the aexA+ or aexA+/ΔcadA *Aspergillus* can further express endogenous or exogenous panD, BAPAT, and 3-HPDH produce at least 0.1 g/l of 3-HP after at least 4 days, for example at least 0.2 g/l, at least 0.25 g/l, at least 0.3 g/l, at least 0.4 g/l, at least 0.5 g/l, at least 0.6 g/l, at least 0.7 g/l, at least 0.8 g/l, at least 0.9 g/l, at least 1.1 g/l, at least 1.2 g/l, at least 1.5 g/l, 1.6 g/l, at least 2 g/l, at least 3 g/l, at least 4 g/l, at least 5 g/l, at least 6 g/l, at least 7 g/l, or at least 8 g/l, after at least 5 days, at least 6 days, at least 7 days, at least 8 days, or at least 10 days, such as after 4 to 6 days, 8 to 10 days, or 4 to 5 days (such as at least 6.5 g/l, at least 7 g/l, at least 7.5 g/l, at least 8 g/l, or at least 8.5 g/l after at least 7 days), when grown in Riscaldati medium (such as modified Riscaldati medium with 20× trace elements) at 30° C. with 150 or 200 rpm shaking.

In some examples, the method further includes isolating the 3-HP made by the disclosed fungi. Once produced, any method can be used to isolate the 3-HP. For example, separation techniques (such as filtration) can be used to remove the fungal biomass from the culture medium, and isolation procedures (e.g., filtration, distillation, precipitation, electrodialysis, and ion-exchange procedures) can be used to obtain the 3-HP from the broth (such as a fungi-free broth). In addition, the 3-HP can be isolated from the culture medium after the 3-HP production phase has been terminated.

Compositions and Kits

Also provided by the present disclosure are compositions that include isolated aexA+ or aexA+/ΔcadA fungi (which in some examples also express panD, BAPAT, and 3-HPDH, such as exogenous panD, BAPAT, and 3-HPDH proteins), such as a medium for culturing, storing, or growing the fungus. In some examples, the *Aspergillus* in the composition are freeze dried or lyophilized.

Also provided by the present disclosure are kits that include isolated aexA+ or aexA+/ΔcadA fungi (which in some examples also express panD, BAPAT, and 3-HPDH, such as exogenous panD, BAPAT, and 3-HPDH proteins), such as a kit that includes a medium for culturing, storing, or growing the fungus. In some examples, the fungi in the kit are freeze dried or lyophilized. In some examples, the kit further includes one or more reagents for transforming *Aspergillus*, such as protoplast isolation buffer, osmotic wash buffer, polyethylene glycol, filtration material (such as miracloth), antibiotic (e.g., hygromycin), or combinations thereof.

Exemplary mediums include that can be in the disclosed compositions and kits include solid medium (such as those containing agar, for example complete medium (CM) or minimal medium (MM)) and liquid media (such as a fermentation broth, such as CM, MM, or CAP medium). In one example, the kit or composition includes Riscaldati medium (100 g Glucose, 0.11 g $KH_2PO_4$, 2.36 g $(NH_4)_2SO_4$, 2.08 g $MgSO_4*7H_2O$, 0.074 g NaCl, 0.13 g $CaCl_2*2H_2O$, 1 ml of 1000× trace elements in 1000 ml DI water, adjust pH to 3.4 with $H_2SO_4$, 1000× trace elements contains 1.3 g/L $ZnSO_4*7H_2O$, 5.5 g/L $FeSO_4*7H_2O$, 0.2 g/L $CuSO_4*5H_2O$, 0.7 g/L $MnCl_2*4H_2O$), for example

| | Conc. (g/L) | Amount | Notes |
|---|---|---|---|
| Glucose | 100 | 100 g | |
| $KH_2PO_4$ | 0.11 | 0.11 g | |
| $(NH_4)_2SO_4$ | 2.36 | 2.36 g | |
| $MgSO_4 * 7H_2O$ | 2.08 | 2.08 g | |
| NaCl | 0.074 | 0.074 g | |
| $CaCl_2 * 2H2O$ | 0.13 | 0.13 g | |
| $ZnSO_4 * 7H_2O$ | 0.0013 | 0.0013 g | Use 1000 X soln. |
| $FeSO_4 * 7H_2O$ | 0.0055 | 0.0055 g | Use 1000 X soln. |
| $CuSO_4 * 5H_2O$ | 0.0002 | 0.0002 g | Use 1000 X soln. |
| $MnCl_2 * 4H_2O$ | 0.0007 | 0.0007 g | |
| DI Water (L) | | 1 L | |
| Autoclave Time | 15 min for small flasks 30 min for large flasks 30-60 for fermenter | | |
| Comments: | Adjust to pH = 3.4 with $H_2SO_4$ | | |

In one example, the kit or composition includes a modified Riscaldati medium with 20× trace elements, for example 20 times of the following

| | | | |
|---|---|---|---|
| $ZnSO_4 * 7H_2O$ | 0.0013 | 0.0013 g | Use 1000 X soln. |
| $FeSO_4 * 7H_2O$ | 0.0055 | 0.0055 g | Use 1000 X soln. |

-continued

| | | | |
|---|---|---|---|
| CuSO$_4$ * 5H$_2$O | 0.0002 | 0.0002 g | Use 1000 X soln. |
| MnCl$_2$ * 4H$_2$O | 0.0007 | 0.0007 g | Use 1000 X soln. |

Example 1

Materials and Methods

This example describes methods used in the experiments described in Examples 2-4 below.

Strains and Vectors

The parental *A. pseudoterreus* strain ATCC 32359 was obtained from American Type Culture Collection (ATCC). The hygromycin phosphotransferase (hph) marker cassette was amplified from vector pCB1003 (Carroll et al., 1994). The Pyrithiamine resistance (ptrA) marker cassette was amplified from vector pRTR1 (Kubodera et al. 2000).

Growth Conditions

All strains were maintained on complete medium agar. The complete medium contained 10 g glucose, 2 g triptase peptone, 1 g yeast extract, 1 g casamino acid, 50 mL 20× NO$_3$ salts, 1 mL of 1000× trace elements, and 1 mL of 1000× vitamin stock in 1 L deionized water with pH adjusted to 6.5 with 1M NaOH. One liter of the 20× NO$_3$ salts contained: 120 g Na$_2$NO$_3$, 10.4 g KCl, 10.4 g MgSO$_4$.7H$_2$O, and 30.4 g KH$_2$PO$_4$. The 1000× vitamin stock solution contained in per 100 ml H$_2$O: 0.01 g biotin, 0.01 g pyridoxine-HCl, 0.01 g thiamine-HCl, 0.01 g riboflavin, 0.01 g para-aminobenzoic acid, and 0.01 g nicotinic acid. The vitamin stock solution was filtered and stored at 4° C. The 1000× trace element contained in per 100 ml de-ionized H$_2$O: 2.2 g ZnSO$_4$.7H$_2$O, 1.1 g H$_3$BO$_3$, 0.5 g MnCl$_2$.4H$_2$O, 0.5 g FeSO$_4$.7H$_2$O, 0.17 g CoCl$_2$.6H$_2$O, 0.16 g CuSO$_4$.5H$_2$O, 0.15 g Na$_2$MoO$_4$.2H$_2$O, and 5 g Na$_2$EDTA. The trace element constituents were added in the listed order and mixed. Then the pH was adjusted to 6.5 with KOH and the de-ionized H$_2$O was added to the final volume of 100 ml. The trace elements stock solution was filtered and stored at 4° C.

The transformants were selected for hygromycin resistance on the agar plates of minimum media (10 g glucose, 50 mL 20× NO$_3$ salts, 1 mL 1000× trace elements, and 1 mL 1000× vitamin stock in 1 L de-ionized H$_2$O with pH adjusted to 6.5 with 1M NaOH, 100 mg/L hygromycin B). The IA production medium is Riscaldati medium as described previously (Riscaldati et al., 2000), which contained 100 g glucose, 0.11 g KH$_2$PO$_4$, 2.36 g (NH$_4$)$_2$SO$_4$, 2.08 g MgSO$_4$.7H$_2$O, 0.074 g NaCl, 0.13 g CaCl$_2$.2H$_2$O, and 1 mL 1000× trace elements in 1 L de-ionized water with the pH adjusted to 3.4 with 1M H$_2$SO$_4$. One liter of the 1000× trace element solution contained 1.3 g ZnSO$_4$.7H$_2$O, 5.5 g FeSO$_4$.7H$_2$O, 0.2 g CuSO$_4$.5H$_2$O, and 0.7 g MnCl$_2$.4H$_2$O.

Conidia of spore were grown on the agar plate of complete medium for five days and then harvested by washing them with sterile 0.4% Tween 80 solution. Samples for EST analysis were collected from *A. pseudoterreus* ATCC32359 grown in a 20 L Riscaldati medium in a 30 L stirred tank bioreactor. Other experiments were performed in shake flasks. In shake flasks experiments, approximately 2×10$^6$ conidia/mL were inoculated into 30 mL of Riscaldati medium in a 125 ml Erlenmeyer flask. Cultivation was performed at 30° C. on a rotary shaker at 200 rpm. At intervals during the incubation period, three single flasks were harvested for high-performance liquid chromatography (HPLC) analysis, biomass measurement, and RNA extraction. All experiments were carried out in triplicate, and the standard deviation of the IA concentration or dry weight was always less than 10% of the mean.

Construction of Deletion and Overexpression Mutants

The deletion and overexpression mutants were constructed by Gibson assembly (Gibson et al. 2010, Gibson et al. 2009) as described in the Gibson Assembly master mix protocol from NEB (Cat #E2611S). Synthetic oligos used for each construct are provided in Tables 1 and 2.

TABLE 1

Oligo sequences for making deletion constructs

| name | sequence | Seq id no |
|---|---|---|
| mfsA up_fwd | aggtcgacggtatcgatagtttaaacgtgaaagagattgaggatc | 34 |
| mfsA up_rev | gtctgtcagaccaatagataccaatgagg | 35 |
| mfsA ptrA_fwd | tatctattggtctgacagacgggcaattg | 36 |
| mfsA ptrA_rev | cattgcagaggagccgctcttgcatctttg | 37 |
| mfsA down_fwd | agagcggctcctctgcaatggatggccttc | 38 |
| mfsA down_rev | gatccccgggctgcagtttaaacgtggcgaggtgaacatctc | 39 |
| 2022 up_fwd | aggtcgacggtatcgatagtttaaaccagttccaacagtggagtg | 40 |
| 2022 up_rev | gtctgtcagaggatacccatcgtgggatg | 41 |
| 2022 ptrA_fwd | atgggtatcctctgacagacgggcaattg | 42 |
| 2022 ptrA_rev | catcccgcacgagccgctcttgcatctttg | 43 |
| 2022 down_fwd | agagcggctcgtgcgggatggggtgtga | 44 |
| 2022 down_rev | ggatccccgggctgcagtttaaacactgtcccagaggtccgtc | 45 |
| 2739 up_fwd | aggtcgacggtatcgatagtttaaacggtaatctcggaattcgc | 46 |

TABLE 1-continued

Oligo sequences for making deletion constructs

| name | sequence | Seq id no |
|---|---|---|
| 2739 up_rev | gtctgtcagaaggaggacattgtgagtag | 47 |
| 2739 ptrA_fwd | atgtcctccttctgacagacgggcaattg | 48 |
| 2739 ptrA_rev | tgaaccagacgagccgctcttgcatctttg | 49 |
| 2739 down_fwd | agagcggctcgtctggttcaagtgaagcttg | 50 |
| 2739 down_rev | ggatccccgggctgcagtttaaacctcctcgagagctggagaac | 51 |
| 2945 up_fwd | aggtcgacggtatcgatagtttaaacgcacgacacaacacagtc | 52 |
| 2945 up_rev | gtctgtcagatcgacggcatgttcaagttg | 53 |
| 2945 ptrA_fwd | atgccgtcgatctgacagacgggcaattg | 54 |
| 2945 ptrA_rev | aacgcaccaggagccgctcttgcatctttg | 55 |
| 2945 down_fwd | agagcggctcctggtgcgttgatggagc | 56 |
| 2945 down_rev | gatccccgggctgcagtttaaacctcttgactatcgcgtatcac | 57 |
| 8846t1 up_fwd | aggtcgacggtatcgatagtttaaacagacgcattgctgttctac | 58 |
| 8846t1 up_rev | gtctgtcagatcgtgctcgtctctcgtc | 59 |
| 8846t1 ptrA_fwd | acgagcacgatctgacagacgggcaattg | 60 |
| 8846t1 ptrA_rev | caacatgctcgagccgctcttgcatctttg | 61 |
| 8846t1 down_fwd | agagcggctcgagcatgttgaatgttgc | 62 |
| 8846t1 down_rev | ggatccccgggctgcagtttaaacaagtcctcgacatggtctg | 63 |
| 9513 up_fwd | ggtcgacggtatcgatagtttaaaccctggtgatcttgtaagcag | 64 |
| 9513 up_rev | gtctgtcagagggagatcatggtctggatg | 65 |
| 9513 ptrA_fwd | atgatctccctctgacagacgggcaattg | 66 |
| 9513 ptrA_rev | tccccgatgggagccgctcttgcatctttg | 67 |
| 9513 down_fwd | agagcggctcccatcggggatggcctaag | 68 |
| 9513 down_rev | ggatccccgggctgcagtttaaactccacacgactgtcgaag | 69 |
| 9885 up_fwd | aggtcgacggtatcgatagtttaaacgcgagagactagtcgttg | 70 |
| 9885 up_rev | gtgatgccattacacggtag | 71 |
| 9885 ptrA_fwd | ctaccgtgtaatggcatcactctgacagacgggcaattg | 72 |
| 9885 ptrA_rev | cggcagtcctgagccgctcttgcatctttg | 73 |
| 9885 down_fwd | agagcggctcaggactgccggagttgttg | 74 |
| 9885 down_rev | ggatccccgggctgcagtttaaacctcatccaacgcaacggc | 75 |
| 9935 up_fwd | aggtcgacggtatcgatagtttaaacccgggtattagatgtgcg | 76 |
| 9935 up_rev | gtctgtcagactgtggacattgtgcggg | 77 |
| 9935 ptrA_fwd | atgtccacagtctgacagacgggcaattg | 78 |
| 9935 ptrA_rev | ggacatggaagagccgctcttgcatctttg | 79 |
| 9935 down_fwd | agagcggctcttccatgtccatctatcatg | 80 |
| 9935 down_rev | ggatccccgggctgcagtttaaacggttcatgacaatggatg | 81 |

TABLE 2

Oligo sequences for g8846 overexpression under the A. nidulus gpdA promoter

| name | sequence | Seq id no |
|---|---|---|
| pBSK + pgpdA_fwd | cgaggtcgacggtatcgatagtttaaacgttgacctagctg | 82 |
| g8846 + pgpdA_rev | ctctcgtcatggtgatgtctgctcaagc | 83 |
| g8846_fwd | agacatcaccatgacgagagacgagcac | 84 |
| g8846_rev | ggcatctacttcagtagccgtaaacagaag | 85 |
| tTrpC_fwd | cggctactgaagtagatgccgaccgcgg | 86 |
| tTrpC_rev | gtctgtcagatcgagtggagatgtggagtg | 87 |
| ptrA_fwd | ctccactcgatctgacagacgggcaattg | 88 |
| ptrA_rev + pBSK | agtggatccccgggctgcagtttaaacgagccgctcttgcatc | 89 |

Oligonucleotides were from IDT (Coraville, Iowa). ExTaq polymerase (TaKaRa Bio USA, Mountain View, California) was used to generate DNA constructs for making gene knockouts. The final PCR product contains a hygromycin or pyrithiamine marker cassette flanked by sequences homologous to the upstream and the downstream regions of the target gene. Approximately 1-2 µg of the final product was used to transform the A. pseudoterreus strain.

Transformation of A. pseudoterreus Protoplasts

Approximately 2×10⁸ conidia of A. pseudoterreus were added to 100 mL of complete medium in a 300 mL Erlenmeyer flask. The cultures were grown overnight (16 to 18 hours) at 30° C. on the rotary shaker at 200 rpm. The mycelia were harvested by filtering the culture through Miracloth and rinsed with 50 mL sterile water. Mycelia (mass of approximately 1 to 2 beans) were transferred into a 50 mL centrifuge tube containing 20 mL of protoplast isolation buffer (400 mg lysing enzyme (L1412, Sigma) dissolved in 20 mL of osmotic wash buffer (0.5 M KCl, and 10 mM sodium phosphate at pH 5.8) and incubated on the rotary shaker at 30° C. with gentle shaking at 70 rpm for 2 hours. Protoplasts were collected by filtering protoplasts through a sterile Miracloth into a 50 mL centrifuge tube and centrifuging at 1000 g for 10 minutes at 4° C. Protoplasts then were washed twice with 20 mL washing solution (0.6M KCl and 0.1M Tris/HCl at pH 7.0) and a third time in 10 mL conditioning solution (0.6M KCl, 50 mM CaCl₂, and 10 mM Tris/HCl and pH 7.5).

For transformation, 1 to 2 µg DNA was added to 2×10⁷ protoplasts in 0.1 mL conditioning solution. A control reaction with no DNA was performed at the same time. Approximately 25 µL of polyethylene glycol (PEG) solution (25% PEG8000, 0.6 M KCl, 50 mM CaCl₂, and 10 mM Tris/HCl at pH 7.5) was added, and the protoplasts were incubated for 20 minutes on ice. An additional 500 µL of the PEG solution was added using a wide bore pipette tip and carefully mixed with the protoplasts by gently pipetting up and down one to two times. The protoplast solution then was incubated for 5 minutes on ice. One milliliter of cold conditioning solution was added and mixed by gently inverting the tube several times. The protoplast suspension was mixed with 12 mL of 50° C. selection agar (minimum media+0.6M KCl+1.5% Agar+100 µg/mL hygromycin B) in a 15 ml screwcap centrifuge tube. The mixtures were mixed by inverting the tubes three to four times and then poured directly onto the petri dish plates.

The control reaction was divided into a positive control plate (agar solution with no antibiotics) and a negative control (agar solution with 100 µg/mL hygromycin B). The solidified plates were incubated overnight at 30° C. The next day, the plates were overlaid with 12 mL of minimum media containing 150 µg/mL hygromycin B. Colonies started to appear after incubating for 3 to 4 days at 30° C. The transformants were excised and transferred onto minimum media slant containing 100 µg/mL hygromycin B. Correct transformants were confirmed by PCR approaches and Southern blotting analysis. The southern blotting procedure was done according to the previous description (Dai et al. 2013).

Mycelial Dry Cell Weight (DCW) Measurement

Mycelia dry cell weight at each time point was determined by harvesting the mycelia from a 30 ml culture onto a pre-weighed filter by suction filtration and washed once with 50 mL distilled water. Subsequently, the dry weight was determined after freeze-drying in a lyophilizer overnight in pre-weighed tubes with filters.

High-Performance Liquid Chromatography Analysis

Supernatant samples were passed through 0.22 µm filter and analyzed for IA, AA and glucose using high/performance liquid chromatography (HPLC) equipped with a Waters 2414 refractive index detector and a Waters 2489 UV/VIS detector. A Bio-Rad Aminex HPX-87H ion exclusion column (300 mm×7.8 mm) at 65° C. was used for analyte separation. Sulfuric acid (0.005 M) was used as eluent at a flow rate of 0.55 mL/min. IA was detected at 210 nm with a Waters 2414 refractive index detector (Waters, Milford, Massachusetts). Run time of each sample was 40 minutes.

Proteomics

Protein extractions were based on a previously established protocol (Kim and Heyman 2018, Nakayasu et al. 2016). Extracted proteins were dissolved in 100 mM NH₄HCO₃ containing 8 M urea and the protein concentration was measured by BCA assay. Disulfide bonds were reduced by adding dithiothreitol to a final concentration of 5 mM and incubating at 60° C. for 30 min. Samples were alkylated with a final concentration of 40 mM iodoacetamide for 1 h at 37° C. The reaction was then diluted 10-fold with 100 mM NH₄HCO₃ followed by the addition of CaCl₂ to 1 mM final concentration. Digestion was carried out for 3 h at 37° C. with 1:50 (wt:wt) trypsin-to-protein ratio. Salts and reagents were removed by solid-phase extraction using C18 cartridges according to the manufacturer instructions and the resulting peptides were dried in a vacuum centrifuge. The peptides were then resuspended in milliQ water and 500 ng of material was loaded onto in-house packed reversed-phase capillary columns (70-cm×75 µm i.d.) with 3-µm Jupiter C18.

The separation was carried out using a nanoAcquity HPLC system (Waters Corporation) at room temperature. The mobile phase A is 0.1% formic acid in water while mobile phase B is 0.1% formic acid in acetonitrile. The elution was carried out at 300 nL/min with the following gradient: 0-2 min 1% B; 2-20 min 8% B; 20-75 min 12% B; 75-97 min 30% B; 97-100 min 45%; 100-105 95%; 105-110 min 95%; 110-140 min 1%. MS analysis was carried out using a Q Exactive Plus (Thermo Fisher Scientific) in data dependent mode. Mass spectrometer settings were as following: full MS (AGC, 1×106; resolution, 30000; m/z range, 350-2000; maximum ion time, 20 ms); MS/MS (AGC, 1×105; resolution, 15000; m/z range, 200-2000; maximum ion time, 200 ms; minimum signal threshold, 2.5×104; isolation width, 2 Da; dynamic exclusion time setting, 45 s; collision energy, nce 30).

All mass spectrometry data were searched using MS-GF+ (Kim Sangtae and Pevzner 2014) and MASIC (Monroe et al. 2008) software. MS-GF+ software was used to identify peptides by scoring MS/MS spectra against peptides derived from the whole protein sequence database. MASIC software was used to generate the selected ion chromatographs (SICs) of all the precursors in MSMS datasets and calculate their peak areas as abundance. MASICResultsMerger (omics.pnl.gov/software/masic-results-merger) was used to append the relevant MASIC stats for each peptide hit result in MS-GF+. The MS-GF+ data were then filtered based on 1% false discovery rate (FDR) and less than 5-ppm mass accuracy to generate a list of qualified peptide hit results. The abundance of peptides was determined as the highest peak area identified for the peptide within a sample. Normalization of the data was performed with median centering based on the rank invariant peptides (Callister et al. 2006). Protein quantification was performed with standard reference-based median averages (Matzke et al. 2013). Statistics were performed with established standard methods (Webb-Robertson et al. 2017). For this specific dataset a t-test was utilized to evaluate comparisons of interest as well as a G-test to evaluate significance of presence/absence. Since only a subset of all possible comparisons are being made the p-values are adjusted via a Bonferroni.

Example 2

Identification of Cis-Aconitic Acid Transporters Using Multi-Omics Analysis

AA and itaconic acid share the same biosynthesis pathway in the cell (FIG. 1). However, production level of AA is much lower than itaconic acid, which is 10 g/L versus 50 g/L. The only difference between AA and itaconic acid biosynthesis pathway is the transport across the plasma membrane. It was hypothesized AA uses a different transporter than itaconic acid, and that transport across the cell plasma membrane may be a limiting factor. The AA transporter was already saturated at 10 g/L.

Figure 2:
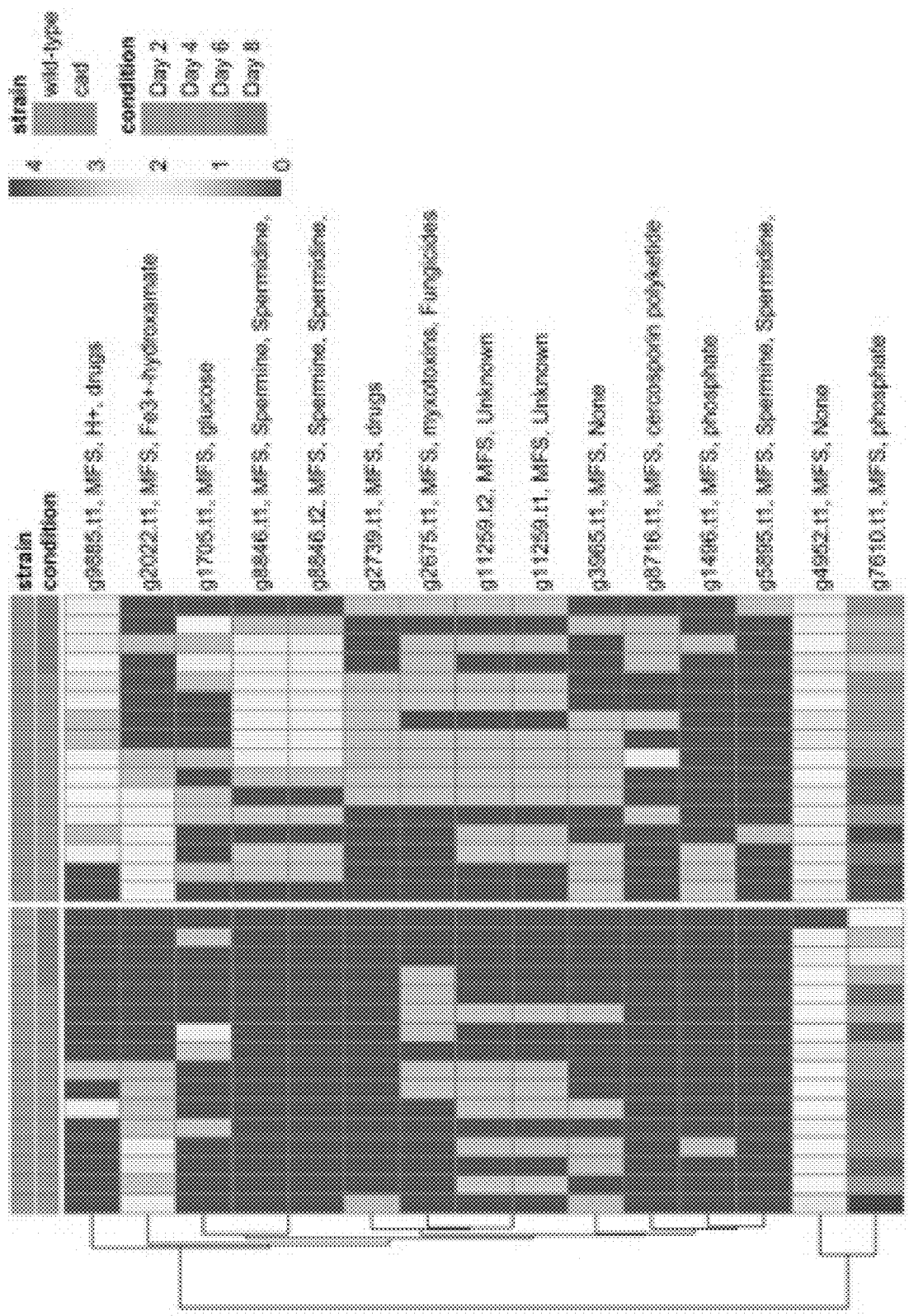
FIG. 2 is a digital heat map showing potential cis-aconitic acid transporters and their expression values from global proteomics of *A. pseudoterreus* wild-type and cadA deletion strains at 2, 4, 6, and 8 days of growth. Log2 of normalized spectral counts are shown as a clustered heatmap (blue—low, yellow—medium, and red—high expression). Row names show protein id, TCDB classification, and predicted substrates.

Global proteomics of *A. pseudoterreus* wild-type and cadA deletion strains were performed to identify potential transporters. First, proteins whose expression levels were responsive to cis-AA production were identified. Proteomics samples were taken at 2, 4, 6, and 8 days of the growth in four biological replicates. The potential transporters in *A. pseudoterreus* were annotated using the Transporter Classification Database (www.ncbi.nlm.nih.gov/pubmed/26546518). Global proteomics detected 7178 proteins out of 13430 annotated proteins, and 123 detected proteins were annotated as the Major Facilitator Superfamily (MFS) by TCDB. The MFS transporters were sorted by the difference of the log 2 normalized spectral counts between the wild-type and cad deletion strains, and the expression patterns of top 15 MFS transporters upregulated in the cadA deletion strain were visually inspected (FIG. 2). Four MFS transporters (g2022, g2739, g8846, and g9885) had higher expression in the cadA deletion strain versus the wild-type strain, and they were selected for further examination.

Example 3

Functional Deletion of Potential Transport Genes

The four potential transporters identified were g2022, g2739, g8846, and g9885. The deletion constructs were built using Gibson assembly (Table 1). mfs is the known itaconic acid transporter on the membrane. For every deletion three individual transformants was picked and single spore isolated. The gene deletions were confirmed by PCR analysis. Three transformants were cultured in Riscaldati medium for 7 days. The AA in the supernatant was measured.

As shown in FIG. 3, only deletion of g8864 had a dramatic effect on reducing AA production. g8846, referred to herein as aconitic acid exporter (aexA) is annotated as a transporter and belongs to MFS family.

Example 4

Overexpression of aexA

To confirm that the g8846 gene is the transporter for AA, it was overexpressed to determine if would increase AA production. An overexpression aexA construct driven by strong promoter pgpdA was built (SEQ ID NO: 21) and transferred into *A. pseudoterreus* cadA minus background. A 7 day culture was grown for three strains, *A. pseudoterreus* with wild type cadA, cadA minus, and cadA minus with g8846/aexA overexpression from the gpdA promoter.

As shown in FIGS. 4A-C, the first column is itaconic acid production in wild type *A. pseudoterreus*, and remaining three columns are AA production in three different strains: *A. pseudoterreus* with wild type cad, cad minus or cad minus with g8846/aexA overexpression. *A. pseudoterreus* with wild type cad (cad+) produced about 35 g/L itaconic acid at day 7 (column 1), but no AA was detected (column 2). However, about 10 g/L AA was detected in *A. pseudoterreus* with a deleted endogenous cadA (Δcad, column 3). Furthermore, the combination of deleting endogenous cadA and overexpressing g8846/aexA from the gpdA promoter, dramatically increased AA production to about 35 g/L (column 4). Its titer, yield and rate are at similarly high level as itaconic acid from wild type *A. pseudoterreus*. This observed overexpression further demonstrates that g8846 is the cell plasma exporter for AA, herein named as aexA (aconitic acid exporter).

Example 5

Production of Organic Acids

To demonstrate that overexpression of aexA can be used to increase production of organic acids in different fungi, the following methods were used. An overexpression aexA construct driven by strong promoter pgpdA was built (SEQ ID NO: 21) and transferred into wild-type *A. pseudoterreus* background or *A. niger* background.

Figure 6A:
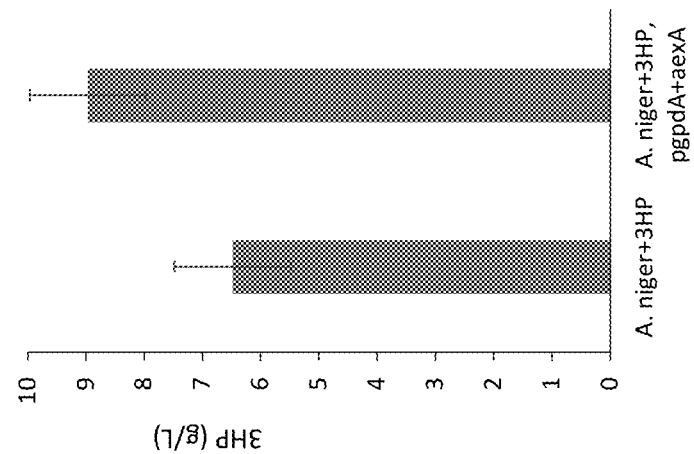
FIGS. 6A-6C are bar graphs showing the effect of aexA (g8846) overexpression using SEQ ID NO: 21 for 7 days on production of (A) itaconic acid in *A. pseudoterreus*, (B) citric acid in *A. niger*, and (C) 3-HP in engineered *A. niger* strain with 3HP pathway.

As shown in FIG. 6A, production of itaconitic acid in *A. pseudoterreus* overexpressing aexA (g8846) did not significantly increase as compared to native *A. pseudoterreus*.

Figure 6B:
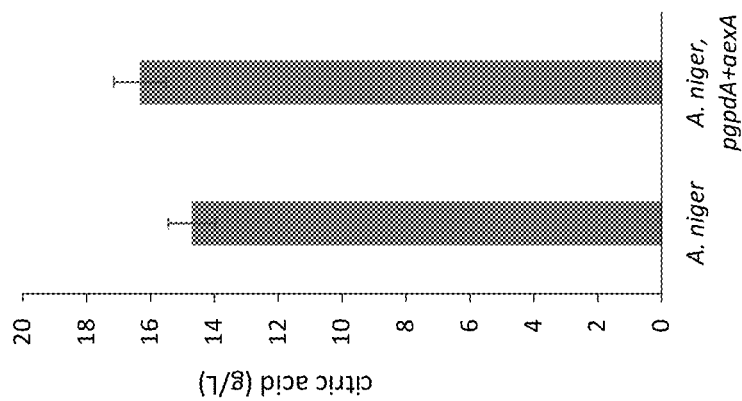

As shown in FIG. 6B, production of citric acid in *A. niger* overexpressing aexA (g8846) was increased by about 14% as compared to native *A. niger*.

Figure 6C:
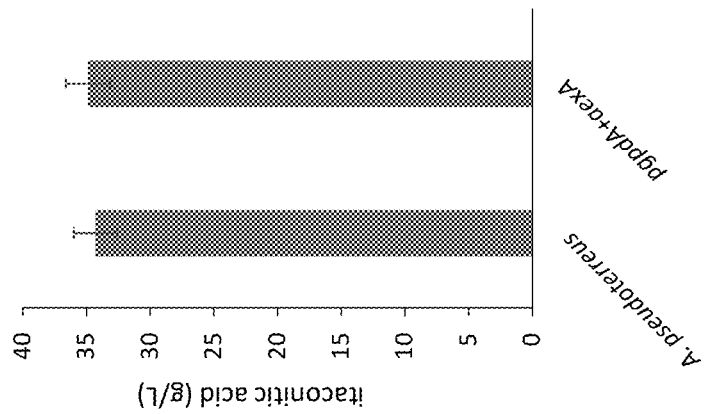

As shown in FIG. 6C, production of 3HP in *A. niger* overexpressing aexA (g8846) and further expressing a transgene expression cassette that allowed for expression of panD, BAPAT, and HPDH (e.g., see U.S. Pat. No. 10,947, 548 and sequences provided herein), increased by about 50% as compared to native *A. niger*.

REFERENCES

Callister et al., 2006. Journal of Proteome Research 5:277-286.
Cao et al., 2011. A novel hyperbranched polyester made from aconitic acid (B3) and di(ethylene glycol) (A2). Polymer International 60:630-634.
Carroll et al., 1994. Fungal Genet. Newsl. 41:22.
Dai et al., 2013. Fungal Genetics and Biology 61:120-132.
Deng et al., 2020. Applied Microbiology and Biotechnology 104:3981-3992.
Gibson et al., 2010. Science 329:52-56.
Gibson et al., 2009. Nature Methods 6:343-345.
Gutierrez, 1978. Preparation of aconitic acid. U.S. Pat. No. 4,123,459.
Kim S, Pevzner P A. 2014. Nature Communications 5:5277.
Kim et al., 2018. Methods Mol Biol 1775:107-118.
Kobayashi et al., 2016. ChemistrySelect:1467-1471.
Kubodera et al., 2000. Bioscience, Biotechnology, and Biochemistry 64:1416-1421.
Kumar V, Raveendiran N. 2018. Synthesis, Characterisation, Biological and Molecular Docking Studies of Aconitic Acid Based Co-Polyester.
Li et al., 2011. A clone-based transcriptomics approach for the identification of genes relevant for itaconic acid production in *Aspergillus*. Fungal Genetics and Biology 48:602-611.
Matzke M M, et al. 2013. A comparative analysis of computational approaches to relative protein quantification using peptide peak intensities in label-free LC-MS proteomics experiments. 13:493-503.
Monroe et al., 2008. Computational Biology and Chemistry 32:215-217.
Nakayasu et al. 2016. mSystems 1:e00043-00016.
Riscaldati et al., 2000. Journal of Biotechnology 83:219-230.
Webb-Robertson et al., 2017. P-MartCancer—Interactive Online Software to Enable Analysis of Shotgun Cancer Proteomic Datasets. Cancer Research 77:e47-e50.
Werpy T, Petersen G. 2004. Top Value Added Chemicals from Biomass: Volume I—Results of Screening for Potential Candidates from Sugars and Synthesis Gas. Office of Scientific and Technical Information (OSTI). Report no.

In view of the many possible embodiments to which the principles of the disclosure may be applied, it should be recognized that illustrated embodiments are only examples of the disclosure and should not be considered a limitation on the scope of the invention. Rather, the scope of the invention is defined by the following claims. We therefore claim as our invention all that comes within the scope and spirit of these claims.

We claim:

1. An isolated recombinant *Aspergillus* fungus comprising an exogenous nucleic acid molecule encoding an aconitic acid exporter (aexA) protein comprising at least 60% sequence identity to SEQ ID NO: 2, 3, 4, or 5, operably linked to an exogenous promoter, thereby overexpressing the aexA in the fungus.

2. The isolated recombinant *Aspergillus* fungus of claim 1, further comprising a genetically inactivated endogenous cis-aconitic acid decarboxylase (cadA) gene.

3. The isolated recombinant *Aspergillus* fungus of claim 1, wherein the *Aspergillus* fungus is *Aspergillus pseudoterreus* or *Aspergillus oryzae*.

4. The isolated recombinant *Aspergillus* fungus of claim 1, wherein the *Aspergillus* fungus is *Aspergillus niger*.

5. The isolated recombinant *Aspergillus* fungus of claim 2, wherein the endogenous cadA gene is genetically inactivated by complete deletion of the cadA gene, partial deletion of the cadA gene, or by insertional mutation of the cadA gene.

6. The isolated recombinant *Aspergillus* fungus of claim 2, wherein the cadA gene prior to its genetic inactivation encodes a protein having at least 80% sequence identity to SEQ ID NO: 7 or 9.

7. The isolated recombinant *Aspergillus* fungus of claim 2, wherein the cadA gene prior to its genetic inactivation comprises a coding sequence having at least 80% sequence identity to SEQ ID NO: 6, 8, 10 or 11.

8. The isolated recombinant *Aspergillus* fungus of claim 1, wherein the nucleic acid molecule encoding aexA comprises at least 60% sequence identity to SEQ ID NO: 1.

9. The isolated recombinant *Aspergillus* fungus of claim 1, wherein the nucleic acid molecule encoding aexA encodes a protein comprising at least 9060% sequence identity to SEQ ID NO: 2, 3, 4, or 5.

10. The isolated recombinant *Aspergillus* of claim 1, wherein the exogenous nucleic acid molecule encoding aexA operably linked to an exogenous promoter is part of a vector.

11. The isolated recombinant *Aspergillus* of claim 10, wherein the vector is a plasmid.

12. The isolated recombinant *Aspergillus* fungus of any one of claim 1, further comprising an endogenous or exogenous nucleic acid molecule encoding aspartate 1-decarboxylase (panD), an endogenous or exogenous nucleic acid molecule encoding (3-alanine-pyruvate aminotransferase (BAPAT), and an endogenous or exogenous nucleic acid molecule encoding 3-hydroxypropionate dehydrogenase (3-HPDH).

13. The isolated recombinant *Aspergillus* fungus of claim 12, wherein the nucleic acid molecule encoding panD comprises:

at least 80% sequence identity to SEQ ID NO: 12 or 14, and/or encodes a panD protein comprising at least 80% sequence identity to SEQ ID NO: 13.

14. The isolated recombinant *Aspergillus* fungus of claim 12, wherein the nucleic acid molecule encoding BAPAT comprises:
at least 80% sequence identity to SEQ ID NO: 15 or 17, and/or encodes a BAPAT protein comprising at least 80% sequence identity to SEQ ID NO: 16.

15. The isolated recombinant *Aspergillus* fungus of claim 12, wherein the nucleic acid molecule encoding 3-HPDH comprises at least 80% sequence identity to SEQ ID NO: 18 or 20, and/or encodes a 3-HPDH protein comprising at least 80% sequence identity to SEQ ID NO: 19.

16. The isolated recombinant *Aspergillus* fungus of claim 12, wherein the exogenous nucleic acid molecule encoding panD, the exogenous nucleic acid molecule encoding BAPAT, and the exogenous nucleic acid molecule encoding 3-HPDH are part of a single exogenous nucleic acid molecule.

17. An isolated nucleic acid molecule encoding an aconitic acid exporter (aexA) operably linked to a heterologous promoter.

18. A vector comprising the isolated nucleic acid molecule of claim 17.

19. A composition comprising the isolated recombinant *Aspergillus* fungus of claim 1.

20. A kit, comprising:
the isolated recombinant *Aspergillus* fungus of claim 1, and a medium for culturing the fungus, protoplast isolation buffer, osmotic wash buffer, polyethylene glycol, filtration material, antibiotic, or combinations thereof.

21. A method of making aconitic acid (AA), comprising:
culturing the isolated recombinant *Aspergillus* fungus of claim 1 under conditions that permit the fungus to make AA, thereby producing AA.

22. The method of claim 21, wherein the fungus is cultured in Riscaldati medium.

23. The method of claim 21, further comprising isolating the AA from culture media or from the fungus.

24. The method of claim 21, wherein the AA is cis-aconitic acid.

25. The method of a claim 21, wherein the amount of AA produced by the isolated recombinant *Aspergillus* fungus is at least 3.5-fold greater than the amount of AA produced by *Aspergillus* fungus without the overexpressed exporter protein.

* * * * *

SEQUENCE LISTING

```
<160> NUMBER OF SEQ ID NOS: 89

<210> SEQ ID NO 1
<211> LENGTH: 1743
<212> TYPE: DNA
<213> ORGANISM: Aspergillus pseudoterreus
<220> FEATURE:
<221> NAME/KEY: misc_feature
<222> LOCATION: (1321)..(1322)
<223> OTHER INFORMATION: n is a, c, g, or t

<400> SEQUENCE: 1
atgacgagag acgagcacga tgttacttcc tcgcggacct ccagcgacga agatgtgatc      60
tccttggagg agcagccaac gcgcgacgac catgccaatg gagcgctaga aaagcagagc     120
acggtcgcct ccggactgtc gaggttggag agtcgcgcgc agtctgtaat ttcgcgcatc     180
cgcagccgcg agcctggtca aacggcgcgc tttacgcatc cgctgtcgca taccaaaacg     240
tcgcccgacg tgattgtgga ttttgacggg ccggacgatc catatcggcc tatgaactgg     300
actttcagga aaaaggccgt gacaactgtg ttgtatggct tgacaacaat gggcgccact     360
tgggcaagtt ccatgtatgt ctagccccc tctctcctac catttgcgaa ttgcgactca     420
ggtatactaa tgatgcgcag tttctcgaca ggcacgcagc aagtgagtaa acagtaccat     480
gtcggcgagg aggttggcac tctcggcacc actctacttc tactcggctt cggtaagtcg     540
ttccatcatg atgtcttcgg tgcatatgcg gactgatcac tcacatctca tcttgcgata     600
```

```
caggtctggg tcctctggtc tgggccccat tgtccgaggt atacggccgc aaaccggccg    660
tcttagcgcc ctactttatc gccgcgatat tctcgttcgg aaccgcaacc gctaaagata    720
tccaaaccat tatgatcacc cgtttcttca ccggattctt cggctcagcc cccgtcacca    780
acaccggtgg tgtgcttggc gatatctggt ccgccgaaga acggggcgcc gctatcgtcg    840
gatacgccat ggctgtcgtg ggcgggccag ttctgggccc cattgttggt ggcgccatcg    900
tacaaagcta cctgcgatgg cgatggacag aatacgtgcg taattcgaat ccccggcga    960 acacacgcca ccccggtca tcagatacta acttcgcccc ccgtacacag atcaccggca   1020
tcatgatgtt cttcttcctg ctcatggacg tcgtgttcct cgacgaaagc tacccgcccg   1080
tcctcctcgt gtacaaagca cggcgcctgc gctacgacac gggcaactgg gccctgcacg   1140
cgaagcacga agaatgggac gtcaccttca aggagctcgg caacaagtac ctcatccgcc   1200
ccttcgcccc cctcgccacg cccatctgct tcctcgtcgc cttgtacgcc tccttcgtct   1260
acggcatcct ctacctcagt ctggcctcct tccccgtcga gtttcaggaa gtgcgcggct   1320
nnccccgtcc ccgaggcccg cctccctccc atgatgctcg gctctgtcct cttcgccgca   1380
ggcctcttca tcttcggctg gaccggccgc ccggatatcc actggatcgg ccccatcatc   1440
ggcgccgtct ccatgggctt cggcttcttc acgatcttcc aggccgccct gaactatctc   1500
atcgatacct tccagaaggt cgcggccagc gctgtggccg ccaacacctt cctccgcagc   1560
gttttcgccg ggtgcttccc gctgttcgcg acgatcatgt tccgcagact cggtgtcgac   1620
tgggcctcga gtgtgttggg gttcgtcgcc gtcgcgttga tcccgatccc gtacctgttc   1680
tatatcttcg gaaagcggat cagagcgaga gggaagtggt cacgcgcttc tgtttacggc   1740
tac                                                                 1743
```

<210> SEQ ID NO 2
<211> LENGTH: 513
<212> TYPE: PRT
<213> ORGANISM: Aspergillus pseudoterreus
<220> FEATURE:
<221> NAME/KEY: misc_feature
<222> LOCATION: (374)..(374)
<223> OTHER INFORMATION: Xaa can be any naturally occurring amino acid

<400> SEQUENCE: 2

```
Met Thr Arg Asp Glu His Asp Val Thr Ser Ser Arg Thr Ser Ser Asp
 1               5                  10                  15

Glu Asp Val Ile Ser Leu Glu Glu Gln Pro Thr Arg Asp Asp His Ala
             20                  25                  30

Asn Gly Ala Leu Glu Lys Gln Ser Thr Val Ala Ser Gly Leu Ser Arg
         35                  40                  45

Leu Glu Ser Arg Ala Gln Ser Val Ile Ser Arg Ile Arg Ser Arg Glu
     50                  55                  60

Pro Gly Gln Thr Ala Arg Phe Thr His Pro Leu Ser His Thr Lys Thr
 65                  70                  75                  80

Ser Pro Asp Val Ile Val Asp Phe Asp Gly Pro Asp Asp Pro Tyr Arg
                 85                  90                  95

Pro Met Asn Trp Thr Phe Arg Lys Lys Ala Val Thr Thr Val Leu Tyr
            100                 105                 110

Gly Leu Thr Thr Met Gly Ala Thr Trp Ala Ser Ser Ile Phe Ser Thr
        115                 120                 125

Gly Thr Gln Gln Val Ser Lys Gln Tyr His Val Gly Glu Glu Val Gly
    130                 135                 140
```

Thr Leu Gly Thr Thr Leu Leu Leu Gly Phe Gly Leu Gly Pro Leu
145                 150                 155                 160

Val Trp Ala Pro Leu Ser Glu Val Tyr Gly Arg Lys Pro Ala Val Leu
            165                 170                 175

Ala Pro Tyr Phe Ile Ala Ala Ile Phe Ser Phe Gly Thr Ala Thr Ala
            180                 185                 190

Lys Asp Ile Gln Thr Ile Met Ile Thr Arg Phe Phe Thr Gly Phe Phe
            195                 200                 205

Gly Ser Ala Pro Val Thr Asn Thr Gly Gly Val Leu Gly Asp Ile Trp
    210                 215                 220

Ser Ala Glu Glu Arg Gly Ala Ala Ile Val Gly Tyr Ala Met Ala Val
225                 230                 235                 240

Val Gly Gly Pro Val Leu Gly Pro Ile Val Gly Ala Ile Val Gln
                245                 250                 255

Ser Tyr Leu Arg Trp Arg Trp Thr Glu Tyr Val Arg Asn Ser Asn Pro
            260                 265                 270

Pro Ala Asn Thr Arg His Pro Arg Ser Ser Asp Thr Asn Phe Ala Pro
                275                 280                 285

Arg Thr Gln Ile Thr Gly Ile Met Met Phe Phe Phe Leu Leu Met Asp
            290                 295                 300

Val Val Phe Leu Asp Glu Ser Tyr Pro Pro Val Leu Leu Val Tyr Lys
305                 310                 315                 320

Ala Arg Arg Leu Arg Tyr Asp Thr Gly Asn Trp Ala Leu His Ala Lys
                325                 330                 335

His Glu Glu Trp Asp Val Thr Phe Lys Glu Leu Gly Asn Lys Tyr Leu
            340                 345                 350

Ile Arg Pro Phe Ala Leu Leu Ala Thr Pro Ile Cys Phe Leu Val Ala
            355                 360                 365

Leu Lys Cys Ala Ala Xaa Pro Val Pro Glu Ala Arg Leu Pro Pro Met
            370                 375                 380

Met Leu Gly Ser Val Leu Phe Ala Ala Gly Leu Phe Ile Phe Gly Trp
385                 390                 395                 400

Thr Gly Arg Pro Asp Ile His Trp Ile Gly Pro Ile Ile Gly Ala Val
                405                 410                 415

Ser Met Gly Phe Gly Phe Phe Thr Ile Phe Gln Ala Ala Leu Asn Tyr
            420                 425                 430

Leu Ile Asp Thr Phe Gln Lys Val Ala Ala Ser Ala Val Ala Ala Asn
            435                 440                 445

Thr Phe Leu Arg Ser Val Phe Ala Gly Cys Phe Pro Leu Phe Ala Thr
            450                 455                 460

Ile Met Phe Arg Arg Leu Gly Val Asp Trp Ala Ser Ser Val Leu Gly
465                 470                 475                 480

Phe Val Ala Val Ala Leu Ile Pro Ile Pro Tyr Leu Phe Tyr Ile Phe
                485                 490                 495

Gly Lys Arg Ile Arg Ala Arg Gly Lys Trp Ser Arg Ala Ser Val Tyr
            500                 505                 510

Gly

<210> SEQ ID NO 3
<211> LENGTH: 575
<212> TYPE: PRT
<213> ORGANISM: Aspergillus terreus

<400> SEQUENCE: 3

```
Met Thr Arg Asp Glu His Asp Val Thr Ser Ser Arg Thr Ser Ser Asp
1               5                   10                  15

Glu Asp Val Ile Ser Leu Glu Glu Gln Pro Thr Arg Asp Asp His Ala
            20                  25                  30

Asn Gly Ala Leu Glu Lys Gln Ser Thr Val Ala Ser Gly Leu Ser Arg
        35                  40                  45

Leu Glu Ser Arg Ala Gln Ser Val Ile Ser Arg Ile Arg Ser Arg Glu
    50                  55                  60

Pro Gly Gln Thr Ala Arg Phe Thr His Pro Leu Ser His Thr Lys Thr
65                  70                  75                  80

Ser Pro Asp Val Ile Val Asp Phe Asp Gly Pro Asp Asp Pro Tyr Arg
                85                  90                  95

Pro Met Asn Trp Thr Phe Arg Lys Lys Ala Val Thr Thr Val Leu Tyr
                100                 105                 110

Gly Leu Thr Thr Met Gly Ala Thr Trp Ala Ser Ser Ile Phe Ser Thr
            115                 120                 125

Gly Thr Gln Gln Val Ser Lys Gln Tyr His Val Gly Glu Glu Val Gly
130                 135                 140

Thr Leu Gly Thr Thr Leu Leu Leu Gly Phe Gly Leu Gly Pro Leu
145                 150                 155                 160

Val Trp Ala Pro Leu Ser Glu Val Tyr Gly Arg Lys Pro Ala Val Leu
                165                 170                 175

Ala Pro Tyr Phe Ile Ala Ala Ile Phe Ser Phe Gly Thr Ala Thr Ala
            180                 185                 190

Lys Asp Ile Gln Thr Ile Met Ile Thr Arg Phe Phe Thr Gly Phe Phe
            195                 200                 205

Gly Ser Ala Pro Val Thr Asn Thr Gly Gly Val Leu Gly Asp Ile Trp
210                 215                 220

Ser Ala Glu Glu Arg Gly Ala Ala Ile Val Gly Tyr Ala Met Ala Val
225                 230                 235                 240

Val Gly Gly Pro Val Leu Gly Pro Ile Val Gly Gly Ala Ile Val Gln
                245                 250                 255

Ser Tyr Leu Arg Trp Arg Trp Thr Glu Tyr Val Arg Asn Ser Asn Pro
            260                 265                 270

Pro Ala Asn Thr Arg His Pro Arg Ser Ser Asp Thr Asn Phe Ala Pro
            275                 280                 285

Arg Thr Gln Ile Thr Gly Ile Met Met Phe Phe Phe Leu Leu Met Asp
290                 295                 300

Val Val Phe Leu Asp Glu Ser Tyr Pro Pro Val Leu Leu Val Tyr Lys
305                 310                 315                 320

Ala Arg Arg Leu Arg Tyr Asp Thr Gly Asn Trp Ala Leu His Ala Lys
                325                 330                 335

His Glu Glu Trp Asp Val Thr Phe Lys Glu Leu Gly Asn Lys Tyr Leu
            340                 345                 350

Ile Arg Pro Phe Ala Leu Leu Ala Thr Pro Ile Cys Phe Leu Val Ala
            355                 360                 365

Leu Tyr Ala Ser Phe Val Tyr Gly Ile Leu Tyr Leu Ser Leu Ala Ser
        370                 375                 380

Phe Pro Val Glu Phe Gln Glu Val Arg Gly Trp Asn Pro Val Val Gly
385                 390                 395                 400
```

```
Ala Leu Pro Phe Leu Ala Tyr Leu Val Gly Ile Leu Phe Gly Ala Cys
                405                 410                 415

Val Asn Leu Phe Asn Gln Arg Phe Tyr Ile Lys Arg Phe Lys Ala Asn
            420                 425                 430

Asn Asn Phe Pro Val Pro Glu Ala Arg Leu Pro Pro Met Met Leu Gly
        435                 440                 445

Ser Val Leu Phe Ala Ala Gly Leu Phe Ile Phe Gly Trp Thr Gly Arg
    450                 455                 460

Pro Asp Ile His Trp Ile Gly Pro Ile Ile Gly Ala Val Ser Met Gly
465                 470                 475                 480

Phe Gly Phe Phe Thr Ile Phe Gln Ala Ala Leu Asn Tyr Leu Ile Asp
                485                 490                 495

Thr Phe Gln Lys Val Ala Ala Ser Ala Val Ala Ala Asn Thr Phe Leu
            500                 505                 510

Arg Ser Val Phe Ala Gly Cys Phe Pro Leu Phe Ala Thr Ile Met Phe
        515                 520                 525

Arg Arg Leu Gly Val Asp Trp Ala Ser Ser Val Leu Gly Phe Val Ala
    530                 535                 540

Val Ala Leu Ile Pro Ile Pro Tyr Leu Phe Tyr Ile Phe Gly Lys Arg
545                 550                 555                 560

Ile Arg Ala Arg Gly Lys Trp Ser Arg Ala Ser Val Tyr Gly Tyr
                565                 570                 575

<210> SEQ ID NO 4
<211> LENGTH: 1198
<212> TYPE: PRT
<213> ORGANISM: Aspergillus arachidicola

<400> SEQUENCE: 4

Met Leu Lys Val Gly Ser Trp Leu Tyr Gly Lys Lys Ala Gly Ala Asn
1               5                   10                  15

Ala Ser Thr Gln Ser Leu Asp Ser Leu Val Glu Leu Arg Asp Leu Glu
            20                  25                  30

Asp Ala Met Arg Ala Ala Thr Leu Ile Leu Asn Asp Asp Val Asp Gly
        35                  40                  45

Ala Glu Asp Gly Leu Ser Glu Gly Val Ser Ser Phe His Asn Leu Gly
    50                  55                  60

Arg Gly Val Val Ala Phe Ile Arg Ala Thr Leu Gly Phe Glu Gln Glu
65                  70                  75                  80

Ile Met Arg Gln Ala Ser Glu Arg Leu Asn Thr Ala Glu Thr Ser Ala
                85                  90                  95

Ala Ser Asp Gln Asn Lys Ala Gln His Asn Ser His Ala Pro Asn Thr
            100                 105                 110

Tyr His Ser Pro Ile Tyr Ser Pro Gly Thr Glu Phe Ala Leu Cys Gln
        115                 120                 125

Ala Met Ala Gln Leu Met Ser Ala Val Val Gly Val Leu Asn Glu Ser
    130                 135                 140

Leu Thr Glu Ser Ile Lys Gly Phe Tyr Lys Met Arg Lys Ala Tyr Ile
145                 150                 155                 160

Thr Leu Asp Gly Ile Leu Lys Met Glu Gln Ala Tyr Met Arg Ser Ile
                165                 170                 175

Ser Gly Gly Val Ser Pro Ala Asp Gln Gly Glu Ala Ser Lys Pro Ser
            180                 185                 190
```

```
Pro Thr Ala Thr Val Glu Ala Lys Gly Leu Ser Gln Arg Leu Ser Asp
        195                 200                 205

Leu Ser Val Ser Gln Asp Ser Thr Lys Ser Gly Glu Ser Thr Glu Pro
    210                 215                 220

Ser Thr Pro Asn Pro Ser Asp Met Leu Ser His Asp Pro Asp Ser Asp
225                 230                 235                 240

Ile Phe Lys Asn Gln Ile Asp Val Phe Val His Ser Gly Ser Asn Phe
                245                 250                 255

Cys Phe Gly Ile Leu Leu Val Ile Ser Met Val Pro Pro Ala Phe
                260                 265                 270

Ser Lys Leu Leu Ser Ile Ile Gly Phe Tyr Gly Asp Lys Glu Arg Gly
                275                 280                 285

Leu Arg Met Leu Trp Gln Ala Ser Lys Phe Asn Asn Leu Ile Gly Ala
            290                 295                 300

Leu Ala Ala Phe Ala Ile Leu Gly Tyr Tyr Asn Gly Phe Val Arg Tyr
305                 310                 315                 320

Cys Asp Ile Met Pro Asp Pro Val Pro Gly Asp Gln Gly Asp Val Gln
                325                 330                 335

Gly Tyr Pro Gln Lys Arg Leu Glu Ala Leu Leu Ala Gln Met Arg Gln
                340                 345                 350

Arg Phe Pro Lys Ser Gln Leu Trp Leu Leu Glu Glu Ser Arg Met Glu
            355                 360                 365

Gly Ala Asn Lys Asn Leu Glu Arg Ser Leu Glu Leu Leu Cys Gly Glu
370                 375                 380

Glu Arg Ser Pro Leu Lys Gln Val Glu Ala Leu Arg Val Phe Glu Arg
385                 390                 395                 400

Ser Leu Asn Ala Met Tyr Leu His Lys Tyr Glu Leu Cys Ala Glu Ala
                405                 410                 415

Phe Leu Glu Cys Val Glu Leu Asn Ser Trp Ser Arg Ser Leu Tyr Tyr
                420                 425                 430

Tyr Ile Ala Gly Ala Ser His Leu Ser Leu Tyr Arg Ser Thr Ile Val
            435                 440                 445

Thr Asp Pro Lys Lys Ala Glu Glu His Ala Glu Lys Ala Thr Glu Tyr
    450                 455                 460

Phe Arg Thr Ala Pro Thr Phe Ala Gly Lys Lys Arg Phe Met Ala Arg
465                 470                 475                 480

Gln Leu Pro Phe Asp Val Phe Val Ala Arg Lys Ile Ala Lys Trp Glu
                485                 490                 495

Ala Arg Ala Lys Glu Trp Gly Val Pro Leu Val Glu Ala Val Gly Val
            500                 505                 510

Asp Pro Ile Glu Glu Met Ile Phe Phe Trp Asn Gly His Ser Arg Met
    515                 520                 525

Thr Gln Ala Gln Leu Asp Glu Ser Met Gln Lys Leu Ala Trp Ser Glu
    530                 535                 540

Ser Asp Glu Asn Lys Lys Trp Ser Arg Glu Gly Pro Glu Glu Lys Ala
545                 550                 555                 560

Ile Leu Gln Leu Leu Arg Ala Ala Val Leu Arg Ala Met Arg Lys His
                565                 570                 575

Asp Glu Ala Arg Gln Leu Leu Lys Glu Ser Val Leu Asn His Asp Lys
                580                 585                 590

Ser Leu Phe Thr Gly His Leu Lys Asp Asn Trp Ile His Pro Val Ala
            595                 600                 605
```

```
His Phe Glu Met Ala Ala Asn Leu Trp Met Glu Arg Pro Gly Tyr Ile
    610                 615                 620

Ala Val His Asp Ala Pro Ala Thr Glu Gly Lys Ile Ala Asn Gly Glu
625                 630                 635                 640

Glu Val Thr Gln Leu Glu Arg Gln Gln Val Arg Glu Cys Lys Glu Tyr
                645                 650                 655

Leu Glu Lys Ala Ala Arg Trp Glu Ser Tyr Glu Leu Asp Ala Arg Ile
            660                 665                 670

Gly Leu Lys Val Thr Ala Ala Met Glu Ala Val Arg Lys Asp Glu Glu
        675                 680                 685

Arg Ser Ser Ser His Ser Ser Leu Asp Asp Asp Gly Asn Ser Leu Glu
690                 695                 700

Leu Arg His Thr Thr Tyr Asp Glu Arg Pro Asn Ala Thr Leu Glu Lys
705                 710                 715                 720

Gln Ser Thr Ala Ala Ser Ala Leu Ser Val Phe Glu Gln Arg Ala Gln
                725                 730                 735

Ser Val Val Ser Arg Ile Arg Ser Arg Glu Pro Gly Gln Thr Ala Arg
            740                 745                 750

Phe Thr His Pro Leu Thr His Thr Lys Thr Ser Thr Asp Val Ile Val
        755                 760                 765

Asp Phe Asp Gly Pro Asp Asp Pro Tyr Arg Pro Leu Asn Trp Ser Phe
770                 775                 780

Arg Lys Lys Ala Ile Thr Thr Leu Leu Tyr Gly Leu Thr Thr Met Gly
785                 790                 795                 800

Ala Thr Trp Ala Ser Ser Ile Tyr Ser Thr Gly Thr Arg Gln Val Asp
                805                 810                 815

Ala Glu Phe Gly Val Gly Glu Val Gly Thr Leu Gly Thr Ala Leu
            820                 825                 830

Leu Leu Phe Gly Phe Gly Leu Gly Pro Leu Val Trp Ala Pro Leu Ser
        835                 840                 845

Glu Val Tyr Gly Arg Lys Pro Ala Val Leu Ala Pro Tyr Phe Ile Ala
850                 855                 860

Ala Ile Phe Ser Phe Gly Thr Ala Thr Ala Lys Asp Leu Gln Thr Val
865                 870                 875                 880

Met Ile Thr Arg Phe Phe Thr Gly Phe Gly Ser Ala Pro Val Thr
                885                 890                 895

Asn Thr Gly Gly Val Leu Ser Asp Ile Trp Thr Ala Glu Gln Arg Gly
            900                 905                 910

Ala Ala Ile Val Gly Tyr Ala Met Ala Val Val Gly Gly Pro Val Leu
        915                 920                 925

Gly Pro Ile Val Gly Gly Ala Ile Val Gln Ser Tyr Leu Gly Trp Arg
        930                 935                 940

Trp Thr Glu Tyr Leu Thr Gly Ile Met Met Met Phe Phe Leu Ala Met
945                 950                 955                 960

Asp Val Leu Phe Leu Asp Glu Ser Tyr Pro Pro Val Leu Leu Val Tyr
                965                 970                 975

Lys Ala Gln Arg Leu Arg Phe Glu Ser Gly Asn Trp Ala Leu His Ala
            980                 985                 990

Arg His Glu Glu Trp Asp Val Thr Phe Lys Glu Leu Gly Asn Lys Tyr
        995                 1000                1005

Leu Ile Arg Pro Phe Gln Leu Leu Thr Thr Pro Ile Cys Phe Leu
        1010                1015                1020
```

Val Ala Leu Tyr Ala Ser Phe Val Tyr Gly Ile Ile Tyr Leu Ser
    1025                1030                1035

Leu Ala Ala Phe Pro Val Glu Phe Gln Glu Val Arg Gly Trp Asn
    1040                1045                1050

Gln Val Val Gly Ala Leu Pro Phe Leu Gly Pro Pro Ser Pro Met
    1055                1060                1065

Met Leu Gly Ser Val Phe Ala Ala Gly Met Phe Val Phe Gly
    1070                1075                1080

Trp Thr Gly Gln Pro Asp Ile His Trp Ile Gly Pro Val Ile Gly
    1085                1090                1095

Ala Val Met Met Gly Phe Gly Phe Phe Thr Ile Phe Gln Ala Ala
    1100                1105                1110

Leu Asn Tyr Leu Ile Asp Thr Phe Gln Lys Val Ser Ala Ser Ala
    1115                1120                1125

Val Ala Ala Asn Thr Phe Leu Arg Ser Val Phe Ala Gly Cys Phe
    1130                1135                1140

Pro Leu Phe Ala Ser Ile Met Phe Arg Lys Leu Gly Val Pro Trp
    1145                1150                1155

Ala Ser Ser Val Leu Gly Phe Val Ser Val Ala Leu Ile Pro Ile
    1160                1165                1170

Pro Tyr Leu Phe Tyr Ile Phe Gly Lys Arg Ile Arg Ala Ala Gly
    1175                1180                1185

Lys Trp Ser Arg Ala Ser Val Tyr Gly Asp
    1190                1195

<210> SEQ ID NO 5
<211> LENGTH: 555
<212> TYPE: PRT
<213> ORGANISM: Aspergillus avenaceus

<400> SEQUENCE: 5

Met Thr Arg Asp Asp Ala Asp Val His Ser Thr Ser Leu Ser Ser Phe
1               5                   10                  15

Asp Asp Asp Thr Asn Ser Leu Asp Glu Arg Pro Thr Gln His Glu Gly
                20                  25                  30

Pro Gly Asn Gly Ala Leu Glu Lys Gln Ser Thr Ala Ala Ser Gly Leu
            35                  40                  45

Ser Val Phe Glu Gln Arg Ala Gln Ser Val Val Ser Arg Ile Arg Ser
        50                  55                  60

Arg Glu Pro Gly Gln Thr Ala Arg Phe Thr His Pro Leu Ser His Thr
65                  70                  75                  80

Lys Thr Thr Glu Asp Ala Ile Val Asp Phe Asp Gly Pro Asp Asp Pro
                85                  90                  95

Tyr Arg Pro Met Asn Trp Gly Phe Lys Lys Lys Ala Met Thr Thr Val
                100                 105                 110

Leu Tyr Gly Leu Thr Thr Met Gly Ala Thr Trp Ser Ser Ser Ile Tyr
            115                 120                 125

Ser Thr Gly Thr Lys Gln Ile Asp Ser Glu Phe Gly Val Gly Glu Glu
        130                 135                 140

Val Gly Thr Leu Gly Thr Ala Leu Leu Leu Phe Gly Phe Gly Leu Gly
145                 150                 155                 160

Pro Leu Ile Trp Ala Pro Leu Ser Glu Val Tyr Gly Arg Lys Pro Ala
                165                 170                 175

Val Leu Ala Pro Tyr Phe Ile Ala Ile Phe Ser Phe Gly Thr Ala
            180                 185                 190

Thr Ala Lys Asp Leu Gln Thr Val Met Leu Thr Arg Phe Thr Gly
            195                 200                 205

Phe Phe Gly Ser Ala Pro Val Thr Asn Thr Gly Gly Val Leu Ser Asp
210                 215                 220

Ile Trp Thr Ala Glu Gln Arg Gly Ala Ile Val Gly Tyr Ala Met
225                 230                 235                 240

Ala Val Val Gly Gly Pro Val Leu Gly Pro Ile Val Gly Gly Ala Ile
                245                 250                 255

Val Gln Ser Tyr Leu Arg Trp Arg Trp Thr Glu Tyr Ile Thr Gly Ile
            260                 265                 270

Met Met Met Phe Phe Leu Thr Met Asp Leu Leu Phe Leu Asp Glu Ser
            275                 280                 285

Tyr Pro Pro Val Leu Leu Val Tyr Lys Ala Arg Arg Leu Arg Phe Asn
            290                 295                 300

Thr Gly Asn Trp Ala Leu His Ala Arg His Glu Glu Trp Asp Val Thr
305                 310                 315                 320

Leu Lys Glu Leu Gly Asn Lys Tyr Leu Ile Arg Pro Phe Gln Leu Leu
            325                 330                 335

Thr Thr Pro Ile Cys Phe Leu Val Ala Leu Tyr Ala Ser Phe Val Tyr
            340                 345                 350

Gly Ile Leu Tyr Leu Ser Leu Ala Ala Phe Pro Val Glu Phe Gln Glu
            355                 360                 365

Ile Arg Gly Trp Asn Pro Val Ile Gly Ala Leu Pro Phe Leu Ala Tyr
            370                 375                 380

Leu Val Gly Ile Leu Phe Gly Ala Cys Ile Asn Leu Leu Asn Gln Lys
385                 390                 395                 400

Phe Tyr Ile Lys Arg Phe Lys Ala Asn Asn Asn Phe Pro Val Pro Glu
            405                 410                 415

Ala Arg Leu Pro Pro Met Met Leu Gly Ser Ile Leu Phe Ala Ala Gly
            420                 425                 430

Leu Phe Val Phe Gly Trp Thr Gly Lys Pro Ser Ile His Trp Ile Gly
            435                 440                 445

Pro Ile Ile Gly Ala Val Met Met Gly Phe Gly Phe Phe Thr Ile Phe
            450                 455                 460

Gln Ala Ala Leu Asn Tyr Leu Ile Asp Thr Phe Gln Ser Val Ser Ala
465                 470                 475                 480

Ser Ala Val Ala Ala Asn Thr Phe Leu Arg Ser Val Phe Ala Gly Thr
            485                 490                 495

Phe Pro Leu Phe Ala Ser Ile Met Phe Arg Arg Leu Gly Val Asn Trp
            500                 505                 510

Ala Ala Ser Ile Leu Gly Phe Val Ala Ile Leu Ile Pro Ile Pro
            515                 520                 525

Tyr Leu Phe Tyr Val Phe Gly Lys Arg Ile Arg Ala Arg Gly Lys Trp
            530                 535                 540

Ser Arg Ala Ser Val Tyr Gly Asp Cys Gly Asn
545                 550                 555

<210> SEQ ID NO 6
<211> LENGTH: 2206
<212> TYPE: DNA
<213> ORGANISM: Aspergillus terreus

```
<400> SEQUENCE: 6
gtgggtcttg aaatcgtatg ccacacttgc tccggatgaa acacattccg gagcgcgcat      60
cgatattgct acacagtata gacccaatgg tctgcagatg ccctaaatgg tagttctcac     120
tggcctgcat taagttctgg ttgcagatca ttgtcggcct aacatcagtg taggttacgg     180
tgtgagattt acttgcatag aagattccag accacaaggt tctagatcct ttgacggcgg     240
actcccctcg aggtgccggg cgccgacgtg tgcgttgctc cgggatttgt aggacgcagc     300
tcggatacct agccgttatg ggaatcggag gttgtagcag cgtaaacaca tggatagtta     360
aataatcgga tgtacaccca ctgttggaaa tgacgggggc ctacaacacg agattatctg     420
atccaatttc tgttcgttgg cattctatca ttcgcagcga aaattgtcct attaaattga     480
ccatgaccaa acaatctgcg gacagcaacg caaagtcagg agttacgtcc gaaatatgtc     540
attgggcatc caacctggcc actgacgaca tcccttcgga cgtattagaa agagcaaaat     600
accttattct cgacggtatt gcatgtgcct gggttggtgc aagagtgcct tggtcagaga     660
agtatgttca ggcaacgatg agctttgagc cgccgggggc ctgcagggtg attggatatg     720
gacaggtaaa ttttattcac tctagacggt ccacaaagta tactgacgat ccttcgtata     780
gaaactgggg cctgttgcag cagccatgac caattccgct ttcatacagg ctacggagct     840
tgacgactac cacagcgaag ccccccctaca ctctgcaagc attgtccttc ctgcggtctt     900
tgcagcaagt gaggtcttag ccgagcaggg caaaacaatt tccggtatag atgttattct     960
agccgccatt gtggggtttg aatctggccc acggatcggc aaagcaatct acggatcgga    1020
cctcttgaac aacggctggc attgtggagc tgtgtatggc gctccagccg gtgcgctggc    1080
cacaggaaag ctcctcggtc taactccaga ctccatggaa gatgctctcg gaattgcgtg    1140
cacgcaagcc tgtggtttaa tgtcggcgca atacggaggc atggtaaagc gtgtgcaaca    1200
cggattcgca gcgcgtaatg gtcttcttgg gggactgttg gcccatggtg ggtacgaggc    1260
aatgaaaggt gtcctggaga gatcttacgg cggtttcctc aagatgttca ccaagggcaa    1320
cggcagagag cctccctaca aagaggagga agtggtggct ggtctcggtt cattctggca    1380
tacctttact attcgcatca agctctatgc ctgctgcgga cttgtccatg gtccagtcga    1440
ggctatcgaa aaccttcagg ggagatatcc cgagctcttg aatagagcca acctcagcaa    1500
cattcgccat gttcatgtac agctttcaac ggcctcgaac agtcactgtg gatggatacc    1560
agaggagaga cccatcagtt caatcgcagg gcagatgagt gtcgcataca ttctcgccgt    1620
ccagctggtc gaccagcaat gtcttttgtc ccagttttct gagtttgatg acaacctgga    1680
gaggccagaa gtttgggatc tggccaggaa ggttacttca tctcaaagcg aagagtttga    1740
tcaagacggc aactgtctca gtgcgggtcg cgtgaggatt gagttcaacg atggttcttc    1800
tattacggaa agtgtcgaga agcctcttgg tgtcaaagag cccatgccaa acgaacggat    1860
tctccacaaa taccgaaccc ttgctggtag cgtgacggac gaatcccggg tgaaagagat    1920
tgaggatctt gtcctcggcc tggacaggct caccgacatt agcccattgc tggagctgct    1980
gaattgcccc gtgaaatcgc cactggtata atgggaagc gatatggaaa catttcatgt    2040
cacgggcaca aattctaggt catatcgtac ctggatggtg aaaccaccag cggtttagca    2100
gatagaagat agactccttc tgctctgcgt tgcgtcttga atttagttcg ttcactggct    2160
taagaactta gaatgcaata cagtctctct tatttcttat taaaat                   2206

<210> SEQ ID NO 7
<211> LENGTH: 490
```

<212> TYPE: PRT
<213> ORGANISM: Aspergillus terreus

<400> SEQUENCE: 7

```
Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Asp Ile Pro Ser
            20                  25                  30

Asp Val Leu Glu Arg Ala Lys Tyr Leu Ile Leu Asp Gly Ile Ala Cys
        35                  40                  45

Ala Trp Val Gly Ala Arg Val Pro Trp Ser Glu Lys Tyr Val Gln Ala
    50                  55                  60

Thr Met Ser Phe Glu Pro Pro Gly Ala Cys Arg Val Ile Gly Tyr Gly
65                  70                  75                  80

Gln Lys Leu Gly Pro Val Ala Ala Ala Met Thr Asn Ser Ala Phe Ile
                85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
        115                 120                 125

Glu Gln Gly Lys Thr Ile Ser Gly Ile Asp Val Ile Leu Ala Ala Ile
    130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
        195                 200                 205

Ser Ala Gln Tyr Gly Gly Met Val Lys Arg Val Gln His Gly Phe Ala
    210                 215                 220

Ala Arg Asn Gly Leu Leu Gly Leu Leu Ala His Gly Gly Tyr Glu
225                 230                 235                 240

Ala Met Lys Gly Val Leu Glu Arg Ser Tyr Gly Gly Phe Leu Lys Met
                245                 250                 255

Phe Thr Lys Gly Asn Gly Arg Glu Pro Pro Tyr Lys Glu Glu Glu Val
            260                 265                 270

Val Ala Gly Leu Gly Ser Phe Trp His Thr Phe Thr Ile Arg Ile Lys
        275                 280                 285

Leu Tyr Ala Cys Cys Gly Leu Val His Gly Pro Val Glu Ala Ile Glu
    290                 295                 300

Asn Leu Gln Gly Arg Tyr Pro Glu Leu Leu Asn Arg Ala Asn Leu Ser
305                 310                 315                 320

Asn Ile Arg His Val His Val Gln Leu Ser Thr Ala Ser Asn Ser His
                325                 330                 335

Cys Gly Trp Ile Pro Glu Glu Arg Pro Ile Ser Ser Ile Ala Gly Gln
            340                 345                 350

Met Ser Val Ala Tyr Ile Leu Ala Val Gln Leu Val Asp Gln Gln Cys
        355                 360                 365

Leu Leu Ser Gln Phe Ser Glu Phe Asp Asp Asn Leu Glu Arg Pro Glu
    370                 375                 380

Val Trp Asp Leu Ala Arg Lys Val Thr Ser Ser Gln Ser Glu Glu Phe
385                 390                 395                 400
```

```
Asp Gln Asp Gly Asn Cys Leu Ser Ala Gly Arg Val Arg Ile Glu Phe
            405                 410                 415

Asn Asp Gly Ser Ser Ile Thr Glu Ser Val Glu Lys Pro Leu Gly Val
        420                 425                 430

Lys Glu Pro Met Pro Asn Glu Arg Ile Leu His Lys Tyr Arg Thr Leu
    435                 440                 445

Ala Gly Ser Val Thr Asp Glu Ser Arg Val Lys Glu Ile Glu Asp Leu
450                 455                 460

Val Leu Gly Leu Asp Arg Leu Thr Asp Ile Ser Pro Leu Leu Glu Leu
465                 470                 475                 480

Leu Asn Cys Pro Val Lys Ser Pro Leu Val
                485                 490

<210> SEQ ID NO 8
<211> LENGTH: 1862
<212> TYPE: DNA
<213> ORGANISM: Aspergillus vadensis

<400> SEQUENCE: 8
gttttctgtg tgtctttggg gggttataaa tagggtgtcg aatatctgga agatagggaa      60
ttctttctct ttcaatcaat caatcaagaa ttcttttagg gagtttctat actacatccg     120
atatggtcgc catcaccgct aaatctgaag cggcttctgc tacttcgccc attcctacca     180
attctaatac taccatgact actaccctca acggggtaga tggttcaaaa gagaaagaaa     240
aagaccagat accccaaac aaagaggaag gaacaaaagc agaagagaaa gaaaccgaag      300
catacaactc ctccaacggc gtcaccagcc aactctgcaa ctggatcgcc tctctccagc     360
tagaagacat tccagactct gtccgcaccc gcgccaagta cctctttctc gatggcatcg     420
cctgcgcact cgtcggtgcg cgcgtcccat ggtcgcagaa ggcttttgat gcgatggctg     480
ttttcgagga aagggaaag catgtggtta ttgggtatga agagcgcctt ggtgctatcg      540
ccgccgcaac cctcaacggc tcctggatcc aagcctgcga agtagacgac taccacagcg     600
tggcgcccct gcactcgcag gccgtggtca tccctcctct cttcgctgcc gccgtcagtg     660
cgcggaacca tccgaccgca ccgcgcatca tcgacgggcg aacacttctt ctcgcctccg     720
tggtagggtt cgaggttggt ccgcgcgtgg gcatggcgct acacggcacc gagatgctcg     780
cgaagggatg gcactgcggg tctgtgtttg gtggaccccgc ggccgcaggc agttctgcaa    840
aactactcgg tttgtcggcg ggtcaagtcg aagacgcgat cggagtagca gcgacacaag     900
catgcggact catggcggcg cagtacgacg ggatggtgaa gcggatgcat catggcttcg     960
cggcaaggaa tggactgttg ggcacgatgt tagcgtgggg aggttatgaa gggatcaaga    1020
aggtgtttga gcgccgtat ggaggatttc tggcaatgtt tggcctaggg tcgaagcaca     1080
cgcctagttc gaagccggag gaggtggcaa aggatttggg gacgttctgg cacacggcgg    1140
agtggattcg gttgaagttg catgcgtgct gtgggggat tcatggcacg attgagtgtt    1200
tggcggagat gcaggagatg tatccagagc gatttggacg ggagaaacta ggagagatca    1260
aggagattcg gatccagttg agtgatgcgt tgtttcatca ttgtggatgg gcgccggaga    1320
cgaggccgtt gaccccgacg ggggcgcaga tgaatacggc gtttgtggcg gcctcgcagt    1380
tggtggatgg acaagtgttg ttggagcagt tctcgtcggg gaagttggat cgggatgagg    1440
tttgggaatt gattgggaag acgagttgta ttcatacggc ggagttggac aagccgaata    1500
ttggttgtgg tgcgttgatc tccatcacgt ttgcggatgg cagtcaggtt cagcattcgt    1560
```

```
tgttgaagcc aagggggtg gatgaaccca tttcgaatga ggagatcttg gagaagtttc    1620
gtcggttgac gggcggttg attggggtgg agaggcagga aagattgaa aaggccgtgc    1680 tggggatgga ggagttgcag gatgtggatg agttgattga gttgctgagt gtgaatgtgg    1740
tcaatccgtt gcagtagtat actagtcatc tgttttgatg cttctggcgt tggtcgtgtt    1800
gggatagtat ctcataattt tgaattaata aatcattcaa catggtgaaa atcatatttg    1860
tg                                                                     1862
```

<210> SEQ ID NO 9
<211> LENGTH: 544
<212> TYPE: PRT
<213> ORGANISM: Aspergillus vadensis

<400> SEQUENCE: 9

```
Met Val Ala Ile Thr Ala Lys Ser Glu Ala Ala Ser Ala Thr Ser Pro
1               5                   10                  15

Ile Pro Thr Asn Ser Asn Thr Thr Met Thr Thr Thr Leu Asn Gly Val
            20                  25                  30

Asp Gly Ser Lys Glu Lys Glu Lys Asp Gln Ile Pro Pro Asn Lys Glu
        35                  40                  45

Glu Gly Thr Lys Ala Glu Glu Lys Glu Thr Glu Ala Tyr Asn Ser Ser
    50                  55                  60

Asn Gly Val Thr Ser Gln Leu Cys Asn Trp Ile Ala Ser Leu Gln Leu
65                  70                  75                  80

Glu Asp Ile Pro Asp Ser Val Arg Thr Arg Ala Lys Tyr Leu Phe Leu
                85                  90                  95

Asp Gly Ile Ala Cys Ala Leu Val Gly Ala Arg Val Pro Trp Ser Gln
            100                 105                 110

Lys Ala Phe Asp Ala Met Ala Val Phe Glu Glu Lys Gly Lys His Val
        115                 120                 125

Val Ile Gly Tyr Glu Glu Arg Leu Gly Ala Ile Ala Ala Ala Thr Leu
    130                 135                 140

Asn Gly Ser Trp Ile Gln Ala Cys Glu Val Asp Asp Tyr His Ser Val
145                 150                 155                 160

Ala Pro Leu His Ser Gln Ala Val Val Ile Pro Pro Leu Phe Ala Ala
                165                 170                 175

Ala Val Ser Ala Arg Asn His Pro Thr Ala Pro Arg Ile Ile Asp Gly
            180                 185                 190

Arg Thr Leu Leu Leu Ala Ser Val Val Gly Phe Glu Val Gly Pro Arg
        195                 200                 205

Val Gly Met Ala Leu His Gly Thr Glu Met Leu Ala Lys Gly Trp His
    210                 215                 220

Cys Gly Ser Val Phe Gly Gly Pro Ala Ala Ala Gly Ser Ser Ala Lys
225                 230                 235                 240

Leu Leu Gly Leu Ser Ala Gly Gln Val Glu Asp Ala Ile Gly Val Ala
                245                 250                 255

Ala Thr Gln Ala Cys Gly Leu Met Ala Ala Gln Tyr Asp Gly Met Val
            260                 265                 270

Lys Arg Met His His Gly Phe Ala Ala Arg Asn Gly Leu Leu Gly Thr
        275                 280                 285

Met Leu Ala Trp Gly Gly Tyr Glu Gly Ile Lys Lys Val Phe Glu Arg
    290                 295                 300

Pro Tyr Gly Gly Phe Leu Ala Met Phe Gly Leu Gly Ser Lys His Thr
305                 310                 315                 320
```

```
Pro Ser Ser Lys Pro Glu Glu Val Ala Lys Asp Leu Gly Thr Phe Trp
            325                 330                 335
His Thr Ala Glu Trp Ile Arg Leu Lys Leu His Ala Cys Cys Gly Gly
                340                 345                 350
Ile His Gly Thr Ile Glu Cys Leu Ala Glu Met Gln Glu Met Tyr Pro
            355                 360                 365
Glu Arg Phe Gly Arg Glu Lys Leu Gly Glu Ile Lys Glu Ile Arg Ile
        370                 375                 380
Gln Leu Ser Asp Ala Val Phe His His Cys Gly Trp Ala Pro Glu Thr
385                 390                 395                 400
Arg Pro Leu Thr Pro Thr Gly Ala Gln Met Asn Thr Ala Phe Val Ala
                405                 410                 415
Ala Ser Gln Leu Val Asp Gly Gln Val Leu Leu Glu Gln Phe Ser Ser
            420                 425                 430
Gly Lys Leu Asp Arg Asp Glu Val Trp Glu Leu Ile Gly Lys Thr Ser
        435                 440                 445
Cys Ile His Thr Ala Glu Leu Asp Lys Pro Asn Ile Gly Cys Gly Ala
    450                 455                 460
Leu Ile Ser Ile Thr Phe Ala Asp Gly Ser Gln Val Gln His Ser Leu
465                 470                 475                 480
Leu Lys Pro Lys Gly Val Asp Glu Pro Ile Ser Asn Glu Glu Ile Leu
                485                 490                 495
Glu Lys Phe Arg Arg Leu Thr Gly Gly Leu Ile Gly Val Glu Arg Gln
            500                 505                 510
Glu Lys Ile Glu Lys Ala Val Leu Gly Met Glu Glu Leu Gln Asp Val
        515                 520                 525
Asp Glu Leu Ile Glu Leu Leu Ser Val Asn Val Asn Pro Leu Gln
    530                 535                 540

<210> SEQ ID NO 10
<211> LENGTH: 987
<212> TYPE: DNA
<213> ORGANISM: Aspergillus pseudoterreus

<400> SEQUENCE: 10
ggttgtagca gcgtaaacac atggatagtt aaataatcgg atgtacaccc actgttggaa      60
atgacggggg cctacaacac gagattatct gatccaattt ctgttcgttg cattctatc     120
attcgcagcg aaaattgtcc tattaaattg accatgacca acaatctgc ggacagcaac     180
gcaaagtcag gagttacgtc cgaaatatgt cattgggcat ccaacctggc cactgacgac     240
atcccttcgg acgtattaga aagagcaaaa taccttattc tcgacggtat tgcatgtgcc     300
tggggttggtg caagagtgcc ttggtcagag aagtatgttc aggcaacgat gagctttgag     360
ccgccggggg cctgcagggt gattggatat ggacaggtaa attttattca ctctagacgg     420
tccacaaagt atactgacga tccttcgtat agaaactggg gcctgttgca gcagccatga     480
ccaattccgc tttcatacag gctacggagc ttgacgacta ccacagcgaa gcccccctac     540
actctgcaag cattgtcctt cctgcggtct ttgcagcaag tgaggtctta gccgagcagg     600
gcaaaacaat ttccggtata gatgttattc tagccgccat tgtggggttt gaatctggcc     660
cacggatcgg caaagcaatc tacggatcgg acctcttgaa caacggctgg cattgtggag     720
ctgtgtatgg cgctccagcc ggtgcgctgg ccacaggaaa gctcctcggt ctaactccag     780
actccatgga agatgctctc ggaattgcgt gcacgcaagc ctgtggttta atgtcggcgc     840
```

```
aatacggagg catggtaaag cgtgtgcaac acggattcgc agcgcgtaat ggtcttcttg    900
ggggactgtt ggcccatggt gggtacgagg caatgaaagg tgtcctggag agatcttacg    960
gcggtttcct caagatgttc accaagg                                        987

<210> SEQ ID NO 11
<211> LENGTH: 908
<212> TYPE: DNA
<213> ORGANISM: Aspergillus pseudoterreus

<400> SEQUENCE: 11
ctcagcaaca ttcgccatgt tcatgtacag ctttcaacgg cctcgaacag tcactgtgga     60
tggataccag aggagagacc catcagttca atcgcagggc agatgagtgt cgcatacatt    120
ctcgccgtcc agctggtcga ccagcaatgt cttttgtccc agttttctga gtttgatgac    180
aacctggaga ggccagaagt ttgggatctg gccaggaagg ttacttcatc tcaaagcgaa    240
gagtttgatc aagacggcaa ctgtctcagt gcgggtcgcg tgaggattga gttcaacgat    300
ggttcttcta ttacggaaag tgtcgagaag cctcttggtg tcaaagagcc catgccaaac    360
gaacggattc tccacaaata ccgaacccct gctggtagcg tgacgacga atcccgggtg     420 aaagagattg aggatcttgt cctcggcctg acaggctca ccgacattag cccattgctg     480
gagctgctga attgccccgt gaaatcgcca ctggtataaa tgggaagcga tatgaaaca    540 tttcatgtca cgggcacaaa ttctaggtca tatcgtacct ggatggtgaa accaccagcg    600
gtttagcaga tagaagatag actccttctg ctctgcgttg cgtcttgaat ttagttcgtt    660
cactggctta agaacttaga atgcaataca gtctctctta tttcttatta aaatcacgta    720
ttcccacatt cggcgactgg aggatacgaa agcagtgttg gtggtgctcc ccgtaatgga    780
tatgattttg ctgactggac tattctatga ccattccctc caacggagat cctttctcga    840
cactttagat gttgacgctg tctggaggaa ctacttttgc gctgcaaaga ctatgagcag    900
tggagctg                                                            908

<210> SEQ ID NO 12
<211> LENGTH: 1797
<212> TYPE: DNA
<213> ORGANISM: Tribolium castaneum
<220> FEATURE:
<221> NAME/KEY: CDS
<222> LOCATION: (41)..(1663)

<400> SEQUENCE: 12
acttgtgaat cagtcgtgcc cccacgagga tccacacacg atg ccg gcc aca ggc       55
                                             Met Pro Ala Thr Gly
                                              1               5 gaa gac caa gac ctg gtg caa gac ctc atc gag gag ccc gcc acc ttc      103
Glu Asp Gln Asp Leu Val Gln Asp Leu Ile Glu Glu Pro Ala Thr Phe
             10                  15                  20 agc gac gcc gtc ctc tcc tcc gac gag gaa ctc ttc cac cag aag tgc     151
Ser Asp Ala Val Leu Ser Ser Asp Glu Glu Leu Phe His Gln Lys Cys
         25                  30                  35 ccc aaa ccc gcc ccc att tac tcc ccg gtc tcg aaa ccg gtc tcc ttc     199
Pro Lys Pro Ala Pro Ile Tyr Ser Pro Val Ser Lys Pro Val Ser Phe
     40                  45                  50 gag agc ctc ccc aac agg cgc ctc cac gag gag ttc ctc cgc agc tcg     247
Glu Ser Leu Pro Asn Arg Arg Leu His Glu Glu Phe Leu Arg Ser Ser
 55                  60                  65
```

```
gtg gac gtc ctc ctc cag gag gcg gtg ttc gag gga acg aac cgc aag       295
Val Asp Val Leu Leu Gln Glu Ala Val Phe Glu Gly Thr Asn Arg Lys
70               75                  80                  85 aac cgg gtg ctg caa tgg cgg gag ccg gag gag ttg agg cgt ctg atg       343
Asn Arg Val Leu Gln Trp Arg Glu Pro Glu Glu Leu Arg Arg Leu Met
            90                  95                  100 gac ttt ggg gtg cgg agt gcg ccc tcc acg cac gag gag ttg ttg gag       391
Asp Phe Gly Val Arg Ser Ala Pro Ser Thr His Glu Glu Leu Leu Glu
                105                 110                 115 gtg ttg aag aag gtt gta act tat tcg gtt aaa acc gga cat ccg tac       439
Val Leu Lys Lys Val Val Thr Tyr Ser Val Lys Thr Gly His Pro Tyr
        120                 125                 130 ttc gtg aac cag ttg ttc tcg gcg gtg gat ccg tac ggt ttg gtg gca       487
Phe Val Asn Gln Leu Phe Ser Ala Val Asp Pro Tyr Gly Leu Val Ala
    135                 140                 145 caa tgg gcc acg gat gcg ctc aat ccg agt gtt tac acc tac gag gtt       535
Gln Trp Ala Thr Asp Ala Leu Asn Pro Ser Val Tyr Thr Tyr Glu Val
150                 155                 160                 165 tcg ccg gtt ttt gtt ctg atg gag gaa gtg gtt ttg agg gag atg agg       583
Ser Pro Val Phe Val Leu Met Glu Glu Val Val Leu Arg Glu Met Arg
                170                 175                 180 gcc att gtg ggg ttc gag ggg gga aag ggc gat ggg att ttt tgc cca       631
Ala Ile Val Gly Phe Glu Gly Gly Lys Gly Asp Gly Ile Phe Cys Pro
            185                 190                 195 gga ggg tcc att gcc aat gga tat gcc atc agt tgt gcc aga tac agg       679
Gly Gly Ser Ile Ala Asn Gly Tyr Ala Ile Ser Cys Ala Arg Tyr Arg
        200                 205                 210 ttt atg ccc gat att aag aaa aaa ggc ctc cac tct ctc ccc cgt ttg       727
Phe Met Pro Asp Ile Lys Lys Lys Gly Leu His Ser Leu Pro Arg Leu
215                 220                 225 gtc ctc ttc acc tct gaa gat gcc cac tat tcc atc aaa aaa ctc gcc       775
Val Leu Phe Thr Ser Glu Asp Ala His Tyr Ser Ile Lys Lys Leu Ala
230                 235                 240                 245 tct ttc caa ggc atc ggc acc gac aac gtc tac ttg ata cga acg gac       823
Ser Phe Gln Gly Ile Gly Thr Asp Asn Val Tyr Leu Ile Arg Thr Asp
                250                 255                 260 gcc cga ggt cgc atg gac gtc tcg cac ctg gtg gag gaa atc gag cgt       871
Ala Arg Gly Arg Met Asp Val Ser His Leu Val Glu Glu Ile Glu Arg
            265                 270                 275 tcg ctc cgt gaa ggc gcc gct cct ttc atg gtc agt gcc acc gct gga       919
Ser Leu Arg Glu Gly Ala Ala Pro Phe Met Val Ser Ala Thr Ala Gly
        280                 285                 290 acc aca gtg att ggt gcc ttt gac ccc atc gaa aaa atc gca gat gtg       967
Thr Thr Val Ile Gly Ala Phe Asp Pro Ile Glu Lys Ile Ala Asp Val
295                 300                 305 tgc caa aaa tac aaa ctg tgg ttg cac gtg gat gcc gcc tgg gga ggt      1015
Cys Gln Lys Tyr Lys Leu Trp Leu His Val Asp Ala Ala Trp Gly Gly
310                 315                 320                 325 ggc gcg ctt gtc tct gcc aaa cac cgc cac ctc ctc aaa ggg att gag      1063
Gly Ala Leu Val Ser Ala Lys His Arg His Leu Leu Lys Gly Ile Glu
                330                 335                 340 agg gcc gac tcg gtc acc tgg aac cct cac aaa ctc cta aca gcc ccc      1111
Arg Ala Asp Ser Val Thr Trp Asn Pro His Lys Leu Leu Thr Ala Pro
            345                 350                 355 cag caa tgt tcc aca ctt tta ctg cga cat gag ggt gtc ctc gcc gag      1159
Gln Gln Cys Ser Thr Leu Leu Leu Arg His Glu Gly Val Leu Ala Glu
        360                 365                 370
```

```
gcg cat tcc acg aac gcc gct tac ctc ttc caa aaa gac aaa ttc tac      1207
Ala His Ser Thr Asn Ala Ala Tyr Leu Phe Gln Lys Asp Lys Phe Tyr
    375                 380                 385 gac acc aaa tac gac acg ggc gac aag cac atc cag tgc ggc cgc agg      1255
Asp Thr Lys Tyr Asp Thr Gly Asp Lys His Ile Gln Cys Gly Arg Arg
390                 395                 400                 405 gcc gac gtc ctc aag ttc tgg ttc atg tgg aag gcg aag gga aca tca      1303
Ala Asp Val Leu Lys Phe Trp Phe Met Trp Lys Ala Lys Gly Thr Ser
                410                 415                 420 ggg ttg gag aaa cac gtc gat aaa gtg ttc gaa aat gcg aga ttt ttc      1351
Gly Leu Glu Lys His Val Asp Lys Val Phe Glu Asn Ala Arg Phe Phe
            425                 430                 435 acc gat tgt ata aaa aat cgg gaa ggg ttt gaa atg gtg ata gcg gag      1399
Thr Asp Cys Ile Lys Asn Arg Glu Gly Phe Glu Met Val Ile Ala Glu
        440                 445                 450 ccc gaa tac aca aac atc tgc ttt tgg tac gtg ccg aag agt ctg agg      1447
Pro Glu Tyr Thr Asn Ile Cys Phe Trp Tyr Val Pro Lys Ser Leu Arg
    455                 460                 465 ggg cgc aag gac gaa gcc gat tac aaa gac aag ctg cat aag gtg gcc      1495
Gly Arg Lys Asp Glu Ala Asp Tyr Lys Asp Lys Leu His Lys Val Ala
470                 475                 480                 485 ccc agg att aag gag agg atg atg aag gag ggc tcc atg atg gtc acg      1543
Pro Arg Ile Lys Glu Arg Met Met Lys Glu Gly Ser Met Met Val Thr
                490                 495                 500 tac cag gcg caa aag gga cac ccg aat ttt ttc agg att gtg ttc cag      1591
Tyr Gln Ala Gln Lys Gly His Pro Asn Phe Phe Arg Ile Val Phe Gln
            505                 510                 515 aat tcg ggg ctt gac aag gct gat atg gtg cac ctt gtt gag gag att      1639
Asn Ser Gly Leu Asp Lys Ala Asp Met Val His Leu Val Glu Glu Ile
        520                 525                 530 gag cgg ttg ggg agc gat ctt taa ggccttgaat ggtgctagtt gtagattgtg     1693
Glu Arg Leu Gly Ser Asp Leu
    535                 540 taattaatgt aaaaagtatt atttaaaaaa tgtaaatttt gatgtattta ttctcattag    1753
ttgtagttta ttcaaataaa agtttaaaaa aaaaaaaaaa aaaa                     1797

<210> SEQ ID NO 13
<211> LENGTH: 540
<212> TYPE: PRT
<213> ORGANISM: Tribolium castaneum

<400> SEQUENCE: 13

Met Pro Ala Thr Gly Glu Asp Gln Asp Leu Val Gln Asp Leu Ile Glu
1               5                   10                  15

Glu Pro Ala Thr Phe Ser Asp Ala Val Leu Ser Ser Asp Glu Glu Leu
            20                  25                  30

Phe His Gln Lys Cys Pro Lys Pro Ala Pro Ile Tyr Ser Pro Val Ser
        35                  40                  45

Lys Pro Val Ser Phe Glu Ser Leu Pro Asn Arg Arg Leu His Glu Glu
    50                  55                  60

Phe Leu Arg Ser Ser Val Asp Val Leu Leu Gln Glu Ala Val Phe Glu
65                  70                  75                  80

Gly Thr Asn Arg Lys Asn Arg Val Leu Gln Trp Arg Glu Pro Glu Glu
                85                  90                  95

Leu Arg Arg Leu Met Asp Phe Gly Val Arg Ser Ala Pro Ser Thr His
            100                 105                 110
```

```
Glu Glu Leu Leu Glu Val Leu Lys Lys Val Val Thr Tyr Ser Val Lys
            115                 120                 125

Thr Gly His Pro Tyr Phe Val Asn Gln Leu Phe Ser Ala Val Asp Pro
        130                 135                 140

Tyr Gly Leu Val Ala Gln Trp Ala Thr Asp Ala Leu Asn Pro Ser Val
145                 150                 155                 160

Tyr Thr Tyr Glu Val Ser Pro Val Phe Val Leu Met Glu Glu Val Val
                165                 170                 175

Leu Arg Glu Met Arg Ala Ile Val Gly Phe Glu Gly Lys Gly Asp
            180                 185                 190

Gly Ile Phe Cys Pro Gly Gly Ser Ile Ala Asn Gly Tyr Ala Ile Ser
            195                 200                 205

Cys Ala Arg Tyr Arg Phe Met Pro Asp Ile Lys Lys Lys Gly Leu His
            210                 215                 220

Ser Leu Pro Arg Leu Val Leu Phe Thr Ser Glu Asp Ala His Tyr Ser
225                 230                 235                 240

Ile Lys Lys Leu Ala Ser Phe Gln Gly Ile Gly Thr Asp Asn Val Tyr
                245                 250                 255

Leu Ile Arg Thr Asp Ala Arg Gly Arg Met Asp Val Ser His Leu Val
            260                 265                 270

Glu Glu Ile Glu Arg Ser Leu Arg Glu Gly Ala Ala Pro Phe Met Val
            275                 280                 285

Ser Ala Thr Ala Gly Thr Thr Val Ile Gly Ala Phe Asp Pro Ile Glu
        290                 295                 300

Lys Ile Ala Asp Val Cys Gln Lys Tyr Lys Leu Trp Leu His Val Asp
305                 310                 315                 320

Ala Ala Trp Gly Gly Gly Ala Leu Val Ser Ala Lys His Arg His Leu
                325                 330                 335

Leu Lys Gly Ile Glu Arg Ala Asp Ser Val Thr Trp Asn Pro His Lys
            340                 345                 350

Leu Leu Thr Ala Pro Gln Gln Cys Ser Thr Leu Leu Leu Arg His Glu
        355                 360                 365

Gly Val Leu Ala Glu Ala His Ser Thr Asn Ala Ala Tyr Leu Phe Gln
370                 375                 380

Lys Asp Lys Phe Tyr Asp Thr Lys Tyr Asp Thr Gly Asp Lys His Ile
385                 390                 395                 400

Gln Cys Gly Arg Arg Ala Asp Val Leu Lys Phe Trp Phe Met Trp Lys
                405                 410                 415

Ala Lys Gly Thr Ser Gly Leu Glu Lys His Val Asp Lys Val Phe Glu
            420                 425                 430

Asn Ala Arg Phe Phe Thr Asp Cys Ile Lys Asn Arg Glu Gly Phe Glu
            435                 440                 445

Met Val Ile Ala Glu Pro Glu Tyr Thr Asn Ile Cys Phe Trp Tyr Val
        450                 455                 460

Pro Lys Ser Leu Arg Gly Arg Lys Asp Glu Ala Asp Tyr Lys Asp Lys
465                 470                 475                 480

Leu His Lys Val Ala Pro Arg Ile Lys Glu Arg Met Met Lys Glu Gly
                485                 490                 495

Ser Met Met Val Thr Tyr Gln Ala Gln Lys Gly His Pro Asn Phe Phe
            500                 505                 510

Arg Ile Val Phe Gln Asn Ser Gly Leu Asp Lys Ala Asp Met Val His
            515                 520                 525
```

```
Leu Val Glu Glu Ile Glu Arg Leu Gly Ser Asp Leu
    530                 535                 540

<210> SEQ ID NO 14
<211> LENGTH: 1617
<212> TYPE: DNA
<213> ORGANISM: Artificial Sequence
<220> FEATURE:
<223> OTHER INFORMATION: Synthetic nucleic acid

<400> SEQUENCE: 14
cccgccaccg gcgaggacca ggacctggtg caggacctga tcgaggaacc cgccaccttc     60
tccgacgccg tcctgtcctc cgacgaggaa ctgttccacc agaagtgccc caagccggct    120
ccgatctaca gccccgtcag caagcccgtc agcttcgagt ccctgccgaa ccgccgcctg    180
cacgaagagt tcctccgctc ctccgtcgac gtcctgctgc aagaggccgt gttcgagggc    240
accaaccgca agaaccgcgt cctgcagtgg cgcgagcccg aagaactgcg ccgcctgatg    300
gacttcggcg tccgcagcgc cccgtccacg catgaggaac tgctcgaggt cctgaagaag    360
gtcgtcacct actccgtcaa gaccggccat ccgtacttcg tcaaccagct gttctccgcc    420
gtcgatccct acggcctggt cgcccagtgg gccaccgacg cgctgaaccc ctccgtctac    480
acctacgagg tcagccccgt gttcgtcctg atggaagagg tcgtcctgcg cgagatgcgc    540
gccatcgtcg gcttcgaagg cggcaaaggc gacggcatct tctgccctgg cggctcgatc    600
gccaacggct acgccatcag ctgcgcccgc taccgcttca tgcccgacat caagaagaag    660
ggcctgcact ccctgccgcg cctggtcctg ttcacctccg aggacgccca ctactcgatc    720
aagaagctgg cctcgttcca aggcatcggc accgacaacg tctacctgat ccgcaccgac    780
gctcgcggtc gcatggacgt cagccacctg gtcgaagaga tcgagcgctc cctccgcgag    840
ggcgctgccc cgttcatggt cagcgccacc gccggcacca ccgtcatcgg cgccttcgat    900
cccatcgaga agatcgccga cgtctgccag aagtacaagc tctggctgca cgtcgacgcc    960
gcctggggcg gaggcgctct ggtgtccgcc aagcaccgcc atctgctgaa gggcatcgag   1020
cgcgccgact ccgtcacctg gaatccccac aagctgctga ccgctccgca gcagtgcagc   1080
accctgctgc tgcgccacga gggcgtcctg gccgaggcgc actccaccaa cgccgcctac   1140
ctgttccaga aggacaagtt ctacgacacc aagtacgaca ccggcgacaa gcacatccag   1200
tgcggccgtc gcgccgacgt gctgaagttc tggttcatgt ggaaggccaa gggcacctcc   1260
ggcctcgaga agcacgtgga caaggtgttc gagaacgccc gcttcttcac cgactgcatc   1320
aagaaccgtg agggcttcga gatggtgatc gccgagcctg agtacaccaa catctgtttc   1380
tggtacgtcc ccaagagcct gcgcggacgc aaggacgagg ccgactacaa ggacaagctg   1440
cacaaggtcg cccctcgcat caaagaacgc atgatgaagg aaggctccat gatggtcacc   1500
taccaggcgc agaagggcca tccgaatttc ttccgcatcg tctttcagaa ctccggcctg   1560
gacaaggccg acatggtcca tctggtcgag gaaatcgaac gcctgggctc cgacctc      1617

<210> SEQ ID NO 15
<211> LENGTH: 1356
<212> TYPE: DNA
<213> ORGANISM: Bacillus cereus

<400> SEQUENCE: 15
ttaaagttga gctaaacatt ctttcattgt tttaacgata aaagtaaagt cttcctctgt     60
gatgcttaat ggaggtgcaa gctgcaaaat attattgtaa cctgcaacag tgtcaccatt    120
```

```
tttaccaata attagacctt tttctttaca agcattgatg actttgttca tcttttcaat    180
ggaagccggt tcttttgttt gcttatcttc cactagttca atacctaaaa gaaggccttt    240
tccgcgaaca tctcctacgt ttggatgctc ttttacatct tctagttcat ataacagtcg    300
ttcacccaat tctttggaac gttcaatgag tttctcattc tccataattt ctaaattctt    360
caaagctaag gcgcaagcag caggatttcc tccaaacgta tttacatggc ggaagcgatc    420
ataatcatca ctgcctacga atgcctcata aacctctcgt ctaactgctg ttgctgacaa    480
aggaagatac gcacttgtaa taccttttgc cattgtaatg atatctggtt tgacgccata    540
attcataaat ccaaacggct tccctgttcg tccaaatcca catataactt catcacaaat    600
gagcaacgca ccatgcttct cgcaaatttc ttttactttt tccatatatc catcaggagg    660
cattaaaatt ccgcccccag taatgattgg ctccataatc acaccggcta ctgtttggct    720
taactcccat gtcatgacac gatcgatttc ctcagcactt gccagtgtat gaacatcctc    780
tggattgcga tacgtatcag gcggtgctac atgcaaaaaa ccttgtccta atggctcata    840
tttatacttt ctttgtgctt gccctgttgc tgcaagagca cccattgagt taccgtgata    900
agcgcggtag cgggaaataa acttatagcg tccatgatca cctttttgct gatgatattg    960
acgagcaatt ttaaatgctg tttcatttgc ttctgatcca ctgttagaaa agaaaatgac   1020
gtattcatca tccagccatt cattcaattt ctctgctaat ttaatggcag gaacatgact   1080
ttgtgtcaga gggaaatatg gcatttcttc aagttgctca aatgccgctc ttgcaagctc   1140
ttttcggccg tatccaacat tcacacacca aagaccagac ataccgtcta aataacggtt   1200
tccatcaata tccgtcaccc atgccccttc tgcttttgtg ataattaaat tcgttggact   1260
aggggccgct cctctcatcg catgccaaag gtacttttca tctgtttttt tcaaactttg   1320
tgtttgctct gtcacttgca caatcatcag ctccat                              1356
```

<210> SEQ ID NO 16
<211> LENGTH: 451
<212> TYPE: PRT
<213> ORGANISM: Bacillus cereus

<400> SEQUENCE: 16

```
Met Glu Leu Met Ile Val Gln Val Thr Glu Gln Thr Gln Ser Leu Lys
1               5                   10                  15

Lys Thr Asp Glu Lys Tyr Leu Trp His Ala Met Arg Gly Ala Ala Pro
            20                  25                  30

Ser Pro Thr Asn Leu Ile Ile Thr Lys Ala Glu Gly Ala Trp Val Thr
        35                  40                  45

Asp Ile Asp Gly Asn Arg Tyr Leu Asp Gly Met Ser Gly Leu Trp Cys
    50                  55                  60

Val Asn Val Gly Tyr Gly Arg Lys Glu Leu Ala Arg Ala Ala Phe Glu
65                  70                  75                  80

Gln Leu Glu Glu Met Pro Tyr Phe Pro Leu Thr Gln Ser His Val Pro
                85                  90                  95

Ala Ile Lys Leu Ala Glu Lys Leu Asn Glu Trp Leu Asp Asp Glu Tyr
            100                 105                 110

Val Ile Phe Phe Ser Asn Ser Gly Ser Glu Ala Asn Glu Thr Ala Phe
        115                 120                 125

Lys Ile Ala Arg Gln Tyr His Gln Gln Lys Gly Asp His Gly Arg Tyr
    130                 135                 140

Lys Phe Ile Ser Arg Tyr Arg Ala Tyr His Gly Asn Ser Met Gly Ala
145                 150                 155                 160
```

Leu Ala Ala Thr Gly Gln Ala Gln Arg Lys Tyr Lys Tyr Glu Pro Leu
                165                 170                 175

Gly Gln Gly Phe Leu His Val Ala Pro Pro Asp Thr Tyr Arg Asn Pro
            180                 185                 190

Glu Asp Val His Thr Leu Ala Ser Ala Glu Glu Ile Asp Arg Val Met
        195                 200                 205

Thr Trp Glu Leu Ser Gln Thr Val Ala Gly Val Ile Met Glu Pro Ile
    210                 215                 220

Ile Thr Gly Gly Gly Ile Leu Met Pro Pro Asp Gly Tyr Met Glu Lys
225                 230                 235                 240

Val Lys Glu Ile Cys Glu Lys His Gly Ala Leu Leu Ile Cys Asp Glu
                245                 250                 255

Val Ile Cys Gly Phe Gly Arg Thr Gly Lys Pro Phe Gly Phe Met Asn
            260                 265                 270

Tyr Gly Val Lys Pro Asp Ile Ile Thr Met Ala Lys Gly Ile Thr Ser
        275                 280                 285

Ala Tyr Leu Pro Leu Ser Ala Thr Ala Val Arg Arg Glu Val Tyr Glu
    290                 295                 300

Ala Phe Val Gly Ser Asp Asp Tyr Asp Arg Phe Arg His Val Asn Thr
305                 310                 315                 320

Phe Gly Gly Asn Pro Ala Ala Cys Ala Leu Ala Leu Lys Asn Leu Glu
                325                 330                 335

Ile Met Glu Asn Glu Lys Leu Ile Glu Arg Ser Lys Glu Leu Gly Glu
            340                 345                 350

Arg Leu Leu Tyr Glu Leu Glu Asp Val Lys Glu His Pro Asn Val Gly
        355                 360                 365

Asp Val Arg Gly Lys Gly Leu Leu Leu Gly Ile Glu Leu Val Glu Asp
    370                 375                 380

Lys Gln Thr Lys Glu Pro Ala Ser Ile Glu Lys Met Asn Lys Val Ile
385                 390                 395                 400

Asn Ala Cys Lys Glu Lys Gly Leu Ile Ile Gly Lys Asn Gly Asp Thr
                405                 410                 415

Val Ala Gly Tyr Asn Asn Ile Leu Gln Leu Ala Pro Pro Leu Ser Ile
            420                 425                 430

Thr Glu Glu Asp Phe Thr Phe Ile Val Lys Thr Met Lys Glu Cys Leu
        435                 440                 445

Ala Gln Leu
    450

<210> SEQ ID NO 17
<211> LENGTH: 1350
<212> TYPE: DNA
<213> ORGANISM: Artificial Sequence
<220> FEATURE:
<223> OTHER INFORMATION: Synthetic nucleic acid

<400> SEQUENCE: 17
gagctgggcc agacattcct tcatagtctt gacgatgaag gtgaagtcct cttcggtgat      60
ggacagcgga gggcgagct gcaggatgtt gttgtagccg ccacggtgt cgccgttctt      120 gccgatgatc agacccttct ctttgcaggc gttgatgacc ttgttcatct tttcgatgga      180
ggcgggctct tggtctgct tatcctcgac gagttcgata cccagcagga ggcccttgcc      240
gcggacgtcc ccgacgttgg ggtgctcttt gacgtcctcc aactcgtaca gcaggcgctc      300
gcccagttct ttggaccgct cgatgagctt ctcgttttcc atgatctcga ggttcttcag      360

```
ggccagcgcg caggcggcag ggttgccgcc gaaggtgttg acatggcgga agcggtcgta    420
gtcgtcggag ccgacgaagg cctcgtagac ctcgcggcgg accgcggtgg cagacagcgg    480
caggtaggcc gaggtgatac ccttggccat ggtgataatg tcgggcttga cgccgtagtt    540
catgaagcca aagggcttgc cggtgcgacc gaagccgcag atgacctcgt cgcagatcag    600
cagggcgccg tgcttttcgc agatctcttt gacctttccc atgtagccgt ccggcggcat    660
caggatgcca ccaccggtga tgatgggttc atgatgacg ccggcgacgg tctgggacag    720
ctcccaggtc atgacgcggt cgatttcttc ggcggaggcc agggtgtgca cgtcctcggg    780
gttgcgatag gtgtccggag gggccacgtg caggaagccc tgaccgaggg gctcgtactt    840
gtacttgcgc tgggcctgac cggtcgcggc cagggcaccc atggagttgc cgtggtaggc    900
gcggtagcga gagatgaact tgtagcggcc gtggtcaccc ttctgctggt ggtactggcg    960
ggcgatcttg aaggcggttt cgttggcctc cgagccggga ttggagaaga agatgacgta   1020
ctcgtcgtcc agccactcgt tcagcttctc ggccagcttg atggcgggga cgtgcgactg   1080
cgtcagcggg aagtacggca tctcttccag ctgctcgaag gcagcgcgag ccagctcttt   1140
gcggccgtag ccgacgttga cgcaccacag gccggacatg ccgtccaggt agcggttgcc   1200
gtcgatgtcg gtgacccacg cgccttcggc cttggtgatg atcaggttgg tcggactcgg   1260
agcggcaccg cgcatggcgt gccacaggta cttctcgtcg gttttcttca ggctctgggt   1320
ctgctcggtg acctggacga tcatcagttc                                    1350

<210> SEQ ID NO 18
<211> LENGTH: 747
<212> TYPE: DNA
<213> ORGANISM: Escherichia coli

<400> SEQUENCE: 18
atgatcgttt tagtaactgg agcaacggca ggttttggtg aatgcattac tcgtcgtttt     60
attcaacaag ggcataaagt tatcgccact ggccgtcgcc aggagcggtt gcaggagtta    120
aaagacgaac tgggagataa tctgtatatc gcccaactgg acgttcgcaa ccgcgccgct    180
attgaagaga tgctggcatc gcttcctgcc gagtggtgca atattgatat cctggtaaat    240
aatgccggct tggcgttggg catggagcct gcgcataaag ccagcgttga agactgggaa    300
acgatgattg ataccaacaa caaaggcctg gtatatatga cgcgcgccgt cttaccgggt    360
atggttgaac gtaatcatgg tcatattatt aacattggct caacggcagg tagctggccg    420
tatgccggtg gtaacgttta cggtgcgacg aaagcgtttg ttcgtcagtt tagcctgaat    480
ctgcgtacgg atctgcatgg tacggcggtg cgcgtcaccg acatcgaacc gggtctggtg    540
ggtggcaccg agttttccaa tgtccgcttt aaaggcgatg acggtaaagc ggaaaaaacc    600
tatcaaaata ccgttgcatt gacgccagaa gatgtcagcg aagccgtctg gtgggtgtca    660
acgctgcctg ctcacgtcaa tatcaatacc ctggaaatga tgccggttac ccaaagctat    720
gccggactga atgtccaccg tcagtaa                                        747

<210> SEQ ID NO 19
<211> LENGTH: 248
<212> TYPE: PRT
<213> ORGANISM: Unknown
<220> FEATURE:
<223> OTHER INFORMATION: Enterobacteriaceae
```

<400> SEQUENCE: 19

Met Ile Val Leu Val Thr Gly Ala Thr Ala Gly Phe Gly Glu Cys Ile
1               5                   10                  15

Thr Arg Arg Phe Ile Gln Gln Gly His Lys Val Ile Ala Thr Gly Arg
            20                  25                  30

Arg Gln Glu Arg Leu Gln Glu Leu Lys Asp Glu Leu Gly Asp Asn Leu
        35                  40                  45

Tyr Ile Ala Gln Leu Asp Val Arg Asn Arg Ala Ala Ile Glu Glu Met
    50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
            100                 105                 110

Met Thr Arg Ala Val Leu Pro Gly Met Val Glu Arg Asn His Gly His
        115                 120                 125

Ile Ile Asn Ile Gly Ser Thr Ala Gly Ser Trp Pro Tyr Ala Gly Gly
    130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
        195                 200                 205

Pro Glu Asp Val Ser Glu Ala Val Trp Trp Val Ser Thr Leu Pro Ala
    210                 215                 220

His Val Asn Ile Asn Thr Leu Glu Met Met Pro Val Thr Gln Ser Tyr
225                 230                 235                 240

Ala Gly Leu Asn Val His Arg Gln
                245

<210> SEQ ID NO 20
<211> LENGTH: 741
<212> TYPE: DNA
<213> ORGANISM: Artificial Sequence
<220> FEATURE:
<223> OTHER INFORMATION: codon optimized synthetic cDNA of E. coli HPDH

<400> SEQUENCE: 20
atcgtgctgg tcacgggcgc gaccgccggt tcggcgagt gcatcacccg ccgcttcatc      60
cagcagggcc acaaggtgat cgctaccgga cgccgccaag agcgcctcca agagctgaag     120
gatgagctgg gcgacaacct gtacattgcc cagctggacg tgcgcaaccg ggctgccatc     180
gaagaaatgc tcgcctcgct gcccgccgag tggtgcaaca tcgacatcct ggtcaacaac     240
gccggtctgg ccctcggcat ggaaccggcg cacaaggcca gcgtcgagga ctgggaaacc     300
atgatcgaca ccaacaacaa gggactcgtc tacatgaccc gcgctgtgct gcccggcatg     360
gtcgagcgca ccacggcca catcatcaac atcggctcca ccgctggcag ctggccctac     420
gctggcggca acgtctatgg cgcgaccaag gcgttcgtcc gccagttctc cctgaacctg     480
cgcaccgacc tgcacggcac cgccgtccgc gtgaccgaca ttgagcccgg tctggtcggc     540

```
ggcaccgagt tcagcaacgt ccgcttcaag ggcgacgacg gcaaggccga gaaaacctac    600
cagaacaccg tcgctctgac ccctgaggat gtcagcgagg ccgtctggtg ggtcagcact    660
ctgcccgcgc acgtcaacat caacaccctc gagatgatgc ccgtcacgca gtcctacgcc    720
ggcctgaacg tccaccgcca a                                              741

<210> SEQ ID NO 21
<211> LENGTH: 8478
<212> TYPE: DNA
<213> ORGANISM: Artificial Sequence
<220> FEATURE:
<223> OTHER INFORMATION: Synthetic nucleic acid

<400> SEQUENCE: 21
tgcagcccgg gggatccact agttctagag cggccgccac cgcggtggag ctccagcttt     60
tgttcccttt agtgagggtt aattgcgcgc ttggcgtaat catggtcata gctgtttcct    120
gtgtgaaatt gttatccgct cacaattcca cacaacatac gagccggaag cataaagtgt    180
aaagcctggg gtgcctaatg agtgagctaa ctcacattaa ttgcgttgcg ctcactgccc    240
gctttccagt cgggaaacct gtcgtgccag ctgcattaat gaatcggcca acgcgcgggg    300
agaggcggtt tgcgtattgg gcgctcttcc gcttcctcgc tcactgactc gctgcgctcg    360
gtcgttcggc tgcggcgagc ggtatcagct cactcaaagg cggtaatacg gttatccaca    420
gaatcagggg ataacgcagg aaagaacatg tgagcaaaag gccagcaaaa ggccaggaac    480
cgtaaaaagg ccgcgttgct ggcgtttttc cataggctcc gcccccctga cgagcatcac    540
aaaaatcgac gctcaagtca gaggtggcga acccgacag gactataaag ataccaggcg    600
tttccccctg gaagctccct cgtgcgctct cctgttccga ccctgccgct taccggatac    660
ctgtccgcct ttctcccttc gggaagcgtg gcgctttctc atagctcacg ctgtaggtat    720
ctcagttcgg tgtaggtcgt tcgctccaag ctgggctgtg tgcacgaacc ccccgttcag    780
cccgaccgct gcgccttatc cggtaactat cgtcttgagt ccaacccggt aagacacgac    840
ttatcgccac tggcagcagc cactggtaac aggattagca gagcgaggta tgtaggcggt    900
gctacagagt tcttgaagtg gtggcctaac tacggctaca ctagaaggac agtatttggt    960
atctgcgctc tgctgaagcc agttaccttc ggaaaaagag ttggtagctc ttgatccggc   1020
aaacaaacca ccgctggtag cggtggtttt tttgtttgca agcagcagat tacgcgcaga   1080
aaaaaaggat ctcaagaaga tcctttgatc ttttctacgg ggtctgacgc tcagtggaac   1140
gaaaactcac gttaagggat tttggtcatg agattatcaa aaaggatctt cacctagatc   1200 ctttttaaatt aaaaatgaag ttttaaatca atctaaagta tatatgagta aacttggtct   1260
gacagttacc aatgcttaat cagtgaggca cctatctcag cgatctgtct atttcgttca   1320
tccatagttg cctgactccc cgtcgtgtag ataactacga tacgggaggg cttaccatct   1380
ggccccagtg ctgcaatgat accgcgagac ccacgctcac cggctccaga tttatcagca   1440
ataaaccagc cagccggaag ggccgagcgc agaagtggtc ctgcaacttt atccgcctcc   1500
atccagtcta ttaattgttg ccgggaagct agagtaagta gttcgccagt taatagtttg   1560
cgcaacgttg ttgccattgc tacaggcatc gtggtgtcac gctcgtcgtt tggtatggct   1620
tcattcagct ccggttccca acgatcaagg cgagttacat gatcccccat gttgtgcaaa   1680
aaagcggtta gctccttcgg tcctccgatc gttgtcagaa gtaagttggc cgcagtgtta   1740
tcactcatgg ttatggcagc actgcataat tctcttactg tcatgccatc cgtaagatgc   1800
ttttctgtga ctggtgagta ctcaaccaag tcattctgag aatagtgtat gcggcgaccg   1860
```

```
agttgctctt gcccggcgtc aatacgggat aataccgcgc cacatagcag aactttaaaa    1920
gtgctcatca ttggaaaacg ttcttcgggg cgaaaactct caaggatctt accgctgttg    1980
agatccagtt cgatgtaacc cactcgtgca cccaactgat cttcagcatc ttttactttc    2040
accagcgttt ctgggtgagc aaaaacagga aggcaaaatg ccgcaaaaaa gggaataagg    2100
gcgacacgga aatgttgaat actcatactc ttcctttttc aatattattg aagcatttat    2160
cagggttatt gtctcatgag cggatacata tttgaatgta tttagaaaaa taaacaaata    2220
ggggttccgc gcacatttcc ccgaaaagtg ccacctgacg cgcctgtag cggcgcatta    2280
agcgcggcgg gtgtggtggt tacgcgcagc gtgaccgcta cacttgccag cgccctagcg    2340
cccgctcctt tcgctttctt cccttccttt ctcgccacgt tcgccggctt tccccgtcaa    2400
gctctaaatc gggggctccc tttagggttc cgatttagtg ctttacggca cctcgacccc    2460
aaaaaacttg attagggtga tggttcacgt agtgggccat cgccctgata acggttttt    2520
cgcccttga cgttggagtc cacgttcttt aatagtggac tcttgttcca aactggaaca    2580
acactcaacc ctatctcggt ctattctttt gatttataag ggattttgcc gatttcggcc    2640
tattggttaa aaaatgagct gatttaacaa aaatttaacg cgaattttaa caaaatatta    2700
acgcttacaa tttccattcg ccattcaggc tgcgcaactg ttgggaaggg cgatcggtgc    2760
gggcctcttc gctattacgc cagctggcga aggggatg tgctgcaagg cgattaagtt    2820
gggtaacgcc agggttttcc cagtcacgac gttgtaaaac gacggccagt gagcgcgcgt    2880
aatacgactc actataggc gaattgggta ccggggccccc cctcgaggtc gacggtatcg    2940
atagttaaa cgttgaccta gctgattctg gagtgaccca gagggtcatg acttgagcct    3000
aaaatccgcc gcctccacca tttgtagaaa aatgtgacga actcgtgagc tctgtacagt    3060
gaccggtgac tctttctggc atgcggagag acggacggac gcagagagaa gggctgagta    3120
ataagccact ggccagacag ctctggcggc tctgaggtgc agtggatgat tattaatccg    3180
ggaccggccg cccctccgcc ccgaagtgga aaggctggtg tgcccctcgt tgaccaagaa    3240
tctattgcat catcggagaa tatggagctt catcgaatca ccggcagtaa gcgaaggaga    3300
atgtgaagcc agggtgtat agccgtcggc gaaatagcat gccattaacc taggtacaga    3360
agtccaattg cttccgatct ggtaaaagat tcacgagata gtaccttctc cgaagtaggt    3420
agagcgagta cccggcgcgt aagctcccta attgcccat ccggcatctg tagggcgtcc    3480
aaatatcgtg cctctcctgc tttgcccggt gtatgaaacc ggaaaggccg ctcaggagct    3540
ggccagcggc gcagaccggg aacacaagct ggcagtcgac ccatccggtg tctgcactc    3600
gacctgctga ggtccctcag tccctggtag gcagctttgc cccgtctgtc gcccggtgt    3660
gtcggcgggg ttgacaagt cgttgcgtca gtccaacatt tgttgccata ttttcctgct    3720
ctccccacca gctgctcttt tctttttctct ttcttttccc atcttcagta tattcatctt    3780
cccatccaag aaccttatt tccctaagt aagtactttg ctacatccat actccatcct    3840
tcccatccct tattcctttg aaccttcag ttcgagcttt cccacttcat cgcagcttga    3900
ctaacagcta ccccgcttga gcagacatca ccatgacgag agacgagcac gatgttactt    3960
cctcgcggac ctccagcgac gaagatgtga tctccttgga ggagcagcca acgcgcgacg    4020
accatgccaa tggagcgcta gaaaagcaga gcacggtcgc ctccggactg tcgaggttgg    4080
agagtcgcgc gcagtctgta atttcgcgca tccgcagccg cgagcctggt caaacggcgc    4140
gctttacgca tccgctgtcg cataccaaaa cgtcgcccga cgtgattgtg gattttgacg    4200
```

```
ggccggacga tccatatcgg cctatgaact ggactttcag gaaaaaggcc gtgacaactg    4260
tgttgtatgg cttgacaaca atgggcgcca cttgggcaag ttccatgtat gtctagcccc    4320
cctctctcct accatttgcg aattgcgact caggtatact aatgatgcgc agtttctcga    4380
caggcacgca gcaagtgagt aaacagtacc atgtcggcga ggaggttggc actctcggca    4440
ccactctact tctactcggc ttcggtaagt cgttccatca tgatgtcttc ggtgcatatg    4500
cggactgatc actcacatct catcttgcga tacaggtctg ggtcctctgg tctgggcccc    4560
attgtccgag gtatacggcc gcaaaccggc cgtcttagcg ccctacttta tcgccgcgat    4620
attctcgttc ggaaccgcaa ccgctaaaga tatccaaacc attatgatca cccgtttctt    4680
caccggattc ttcggctcag cccccgtcac caacaccggt ggtgtgcttg gcgatatctg    4740
gtccgccgaa gaacgggcg ccgctatcgt cggatacgcc atggctgtcg tgggcgggcc    4800
agttctgggc cccattgttg gtggcgccat cgtacaaagc tacctgcgat ggcgatggac    4860
agaatacgtg cgtaattcga atcccccggc gaacacacgc cacccccggt catcagatac    4920
taacttcgcc ccccgtacac agatcaccgg catcatgatg ttcttcttcc tgctcatgga    4980
cgtcgtgttc ctcgacgaaa gctacccgcc cgtcctcctc gtgtacaaag cacggcgcct    5040
gcgctacgac acgggcaact gggccctgca cgcgaagcac gaagaatggg acgtcacctt    5100
caaggagctc ggcaacaagt acctcatccg ccccttcgcc ctcctcgcca cgcccatctg    5160
cttcctcgtc gccttgtacg cctccttcgt ctacggcatc ctctacctca gtctggcctc    5220
cttccccgtc gagtttcagg aagtgcgcgg cttttccccgt ccccgaggcc cgcctccctc    5280
ccatgatgct cggctctgtc ctcttcgccg caggcctctt catcttcggc tggaccggcc    5340
gcccggatat ccactggatc ggccccatca tcggcgccgt ctccatgggc ttcggcttct    5400
tcacgatctt ccaggccgcc ctgaactatc tcatcgatac cttccagaag gtcgcggcca    5460
gcgctgtggc cgccaacacc ttcctccgca gcgttttcgc cgggtgcttc ccgctgttcg    5520
cgacgatcat gttccgcaga ctcggtgtcg actgggcctc gagtgtgttg gggttcgtcg    5580
ccgtcgcgtt gatcccgatc ccgtacctgt tctatatctt cggaaagcgg atcagagcga    5640
gagggaagtg gtcacgcgct tctgtttacg gctactgaag tagatgccga ccgcgggatc    5700
cacttaacgt tactgaaatc atcaaacagc ttgacgaatc tggatataag atcgttggtg    5760
tcgatgtcag ctccggagtt gagacaaatg gtgttcagga tctcgataag atacgttcat    5820
ttgtccaagc agcaaagagt gccttctagt gatttaatag ctccatgtca acaagaataa    5880
aacgcgtttt cgggtttacc tcttccagat acagctcatc tgcaatgcat taatgcattg    5940
actgcaacct agtaacgcct ttcaggctcc ggcgaagaga agaatagctt agcagagcta    6000
ttttcatttt cgggagacga gatcaagcag atcaacggtc gtcaagagac ctacgagact    6060
gaggaatccg ctcttggctc cacgcgacta tatttgtc tctaattgta ctttgacatg    6120
ctcctcttct ttactctgat agcttgacta tgaaaattcc gtcaccagct cctgggttcg    6180
caaagataat tgcatgtttc ttccttgaac tctcaagcct acaggacaca cattcatcgt    6240
aggtataaac ctcgaaatca tttcctacta agatggtata caatagtaac catgcatggt    6300
tgcctagtga atgctccgta acacccaata cgccggccga aacttttta caactctcct    6360
atgagtcgtt tacccagaat gcacaggtac acttgtttag aggtaatcct tctttctaga    6420
agtcctcgtg tactgtgtaa gcgcccactc cacatctcca ctcgatctga cagacgggca    6480
attgattacg ggatcccatt ggtaacgaaa tgtaaaagct aggagatcgt ccgccgatgt    6540
caggatgatt tcacttgttt cttgtccggc tcaccggtca aagctaaaga ggagcaaaag    6600
```

```
gaacggatag aatcgggtgc cgctgatcta tacggtatag tgcccttatc acgttgactc   6660
aacccatgct atttaactca acccctcctt ctgaacccca ccatcttctt ccttttcctc   6720
tcatcccaca caattctcta tctcagattt gaattccaaa agtcctcgga cgaaactgaa   6780
caagtcttcc tcccttcgat aaaccttttgg tgattggaat aactgaccat cttctatagt   6840
tcccaaacca accgacaatg taaatacact cctcgattag ccctctagag ggcatacgat   6900
ggaagtcatg gaatactttt ggctggactc tcacaatgat caaggtatct taggtaacgt   6960 cttttggcgtg ggccggtgtt cgttcccagt catcgatgca ttcacatgcc ctccctaagc   7020
tgggccctag actctaggat cctagtctag aaggacatgg catcgatgga ctgggttcgt   7080
tctgagatta tacggctaaa acttgatctg gataatacca gcgaaaaggg tcatgccttc   7140
tctcgttctt cctgttgatg gaatggctaa cagatgatag tcattgcaac ttgaaacatg   7200
tctcctccag ctgccatcta cgaacccact gtggccgcta ccggcctcaa gggtaaggtc   7260
gtggtttctg agaccgtccc cgttgaggga gcttctcaga ccaagctgtt ggaccatttc   7320
ggtggcaagt gggacgagtt caagttcgcc cctatccgcg aaagccaggt ctctcgtgcc   7380
atgaccagac gttactttga ggacctggac aagtacgctg aaagtgacgt tgtcattgtt   7440
ggtgctggtt cctgcggtct gagcactgcg tacgtcttgg ccaaggctcg tccggacctg   7500
aagattgcta tcgtcgaggc cagcgtctct cctggtcagt agtccatgat ggattgcctt   7560
gcactcagct ttccggaact aacgtgcaat aggtggcggt gcctggttgg gtggccaact   7620
cttttctgct atggtcatgc gccgtcccgc ggaagtcttc ctgaacgagc tgggtgttcc   7680
ttacgaagag gacgcaaacc ccaactacgt tgtcgtcaag cacgcctccc tgtttacctc   7740
gacactcatg tcgaaggttc tctccttccc caatgtcaag ctcttcaatg ctaccgctgt   7800
tgaggacttg atcacccgtc cgaccgagaa cggcaacccc cagattgctg gtgttgtcgt   7860
caactggacg ctggtcaccc ttcaccacga tgatcactcc tgcatggacc ccaacactat   7920
caacgctcct gtcatcatca gtaccactgg tcacgatggg ccattcggcg ccttctgtgc   7980
gaagcgcttg gtgtccatgg gcagcgtcga caagctaggt ggcatgcgtg gtctcgacat   8040
gaactcggcc gaggatgcca tcgtcaagaa cacccgcgag gttactaagg gcttgataat   8100
cggcggtatg gagctgtctg aaattgatgg ctttaaccgc atgggcccta ccttcggtgc   8160
catggttctc agtggtgtca aggctgccga ggaggcattg aaggtgttcg acgagcgtca   8220
gcgcgagtgt gctgagtaaa tgactcacta cccgaatggg ttcagtgcat gaaccggatt   8280
tgtcttacgg tctttgacga taggggaatg atgattatgt gatagttctg agatttgaat   8340
gaactcgtta gctcgtaatc cacatgcata tgtaaatggc tgtgtcccgt atgtaacggt   8400
ggggcattct agaataatta tgtgtaacaa gaaagacagt ataatacaaa caaagatgca   8460
agagcggctc gtttaaac                                                8478

<210> SEQ ID NO 22
<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 22
ctccagtaac agaaccgacc                                                 20

<210> SEQ ID NO 23
```

```
<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 23
gaacttcact gccgcattgg                                              20

<210> SEQ ID NO 24
<211> LENGTH: 21
<212> TYPE: DNA
<213> ORGANISM: Artificial Sequence
<220> FEATURE:
<223> OTHER INFORMATION: Synthetic nucleic acid

<400> SEQUENCE: 24
ggacactcca agaggataag g                                            21

<210> SEQ ID NO 25
<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 25
gctcatcaca ttgtttgccg                                              20

<210> SEQ ID NO 26
<211> LENGTH: 50
<212> TYPE: DNA
<213> ORGANISM: Artificial Sequence
<220> FEATURE:
<223> OTHER INFORMATION: Synthetic nucleic acid

<400> SEQUENCE: 26
tgacctccac tagctccagc ggtcaattta agaggacgat cttcgctgcg             50

<210> SEQ ID NO 27
<211> LENGTH: 50
<212> TYPE: DNA
<213> ORGANISM: Artificial Sequence
<220> FEATURE:
<223> OTHER INFORMATION: Synthetic nucleic acid

<400> SEQUENCE: 27
aatagagtag atgccgaccg tcagcctgga caggctcacc gacattagcc             50

<210> SEQ ID NO 28
<211> LENGTH: 50
<212> TYPE: DNA
<213> ORGANISM: Artificial Sequence
<220> FEATURE:
<223> OTHER INFORMATION: Synthetic nucleic acid

<400> SEQUENCE: 28
cgcagcgaag atcgtcctct taaattgacc gctggagcta gtggaggtca             50

<210> SEQ ID NO 29
<211> LENGTH: 50
<212> TYPE: DNA
<213> ORGANISM: Artificial Sequence
<220> FEATURE:
<223> OTHER INFORMATION: Synthetic nucleic acid
```

<400> SEQUENCE: 29

```
ggctaatgtc ggtgagcctg tccaggctga cggtcggcat ctactctatt        50
```

<210> SEQ ID NO 30
<211> LENGTH: 813
<212> TYPE: DNA
<213> ORGANISM: Aspergillus niger

<400> SEQUENCE: 30

```
ctactatgaa agaccgcgat gggccgatag tagtagttac ttccattaca tcatctcatc        60
cgcccggttc ctcgcctccg cggcagtcta cgggtaggat cgtagcaaaa acccgggga       120
tagacccgtc gtcccgagct ggagttccgt ataacctagg tagaaggtat caattgaacc       180
cgaacaactg gcaaaacatt ctcgagatcg taggagtgag tacccggcgt gatggagggg       240
gagcacgctc attggtccgt acggcagctg ccgaggggga gcaggagatc caaatatcgt       300
gagtctcctg ctttgcccgg tgtatgaaac cggaaaggac tgctggggaa ctggggagcg       360
gcgcaagccg ggaatcccag ctgacaattg acccatcctc atgccgtggc agagcttgag       420
gtagcttttg ccccgtctgt ctcccggtg tgcgcattcg actgggcgcg catctgtgc       480
ctcctccagg agcggaggac ccagtagtaa gtaggcctga cctggtcgtt gcgtcagtcc       540
agaggttccc tcccctaccc tttttctact tccctcccc cgccgctcaa cttttctttc       600
cctttacttt tctctctctc ttcctcttca tccatcctct cttcatcact tccctcttcc       660
cttcatccaa ttcatcttcc aagtgagtct tcctcccat ctgtccctcc atctttccca       720
tcatcatctc ccttcccagc tcctcccctc ctctcgtctc ctcacgaagc ttgactaacc       780
attaccccgc cacatagaca catctaaaca atg                                    813
```

<210> SEQ ID NO 31
<211> LENGTH: 1040
<212> TYPE: DNA
<213> ORGANISM: Aspergillus niger

<400> SEQUENCE: 31

```
tgatgggttg gatgacgatg acttcatgtg attttgttat ttagaatatt ttatattcc        60
ttttcttctt ctcaccaccg atcccttaa cactcttgct tcatttgctt cagatttctc       120
ggtttcttct ttttcttct ccccagttat ccactatatc tttgctagac cggcctgcgc       180
cctggcatgc atcataaaat catgtccgtt ggtcatcatc tgttttgtat atccgtcata       240
taaagtattc ttttattccc tccccctcg gtcgtctttc gctgtcccgc ttcctacctc       300
cggtttatag agcatggttc atctcttccg tacatttccg ttggtactag catttatgtc       360
ttcagctagt atagaagctg ccgcagttgt tcgcttacta cctgcctaag tccttaactt       420
tttaaagtgt ttaacctata cgtagtgtta aacgagtact gggaggtggt gaggtagaaa       480
atgttctgca cgggcagtgg gtatttggta gtgtgtaagg cggttattta tcaggctgac       540
gctaaagact tctatgggag cagtatggga tcgcggctca tagaagtaca caaatctaa       600
gagtcgtttg ataattaatt gattcccggc agggtcttct tgggattgag agaactggtt       660
actttgattt gagatattgt aaagcttaag gctcttaaca cgtacgagcg aaacagcagg       720
ggggaaatcg ggaaaagggg cgtgggtga ataaaaagt tgaaataaga cactgtatct       780
tgctgggggt gaataaagag agaataaaag agaggtaaat tccactcagc ccctttcctt       840
cgctctccaa acatcaaact ccgccggccg acccacagga tcccgaacaa gtggaagata       900
```

```
tgtgccggtc cagacccttc gcacagctaa aagcagacct tcataagcgt ttccgggtag      960
tattcgcaca cctgaactgg cacgtcgggg acacaactgt ttttgataca caagaacaca     1020
caccacccat ctaggactca                                                 1040

<210> SEQ ID NO 32
<211> LENGTH: 704
<212> TYPE: DNA
<213> ORGANISM: Aspergillus niger

<400> SEQUENCE: 32
catgttgatg gactggaggg ggatgagtta tggatcagtg aaactgggag aaaacaaaga       60
tggcaaaggg agaacatggc ccagatatag gaaaaaacgg aggaggcaaa aatgtaagcg      120
ctccggactt gctgtttcgg tgtgcactag cagcagcggg ggggaaggtg gtgagtgttc      180
accgaggacc caaaaagaat gagcggatgg cggatgagtg acggagaagg gaaggacggg      240
gggggaatta gaggtggaga ggtccgatcc atcaaataga ccaggctcgg cacagccaag      300
tttcccaaat gatcaactaa tcaatgggac ttggtgctaa atccggagat gccagatcat      360
tgatagacag acaggatgga gtgatggcat atagacagga ggatggatgg atggatagat      420
ggaggggtca agcacaacat ggtgggatga tggcggggtc atgactagca gctaagagga      480
agaagaggag gatgaaatgg acagagaaag atgggagggg tgataaaatg agtatatggg      540
acaagtcata cttacaggac cttgaagatg gtggttgtac tatctaagaa aggctttttt      600
tgagagtact cttaacacaa gaggaggagg gaggagggggg aagtagtaga taaataataa      660
acacgaccac agacttgcta caggctactt cttgtaagct cgag                      704

<210> SEQ ID NO 33
<211> LENGTH: 885
<212> TYPE: DNA
<213> ORGANISM: Aspergillus nidulans

<400> SEQUENCE: 33
tctgtacagt gaccggtgac tctttctggc atgcggagag acggacggac gcagagagaa       60
gggctgagta ataagccact ggccagacag ctctggcggc tctgaggtgc agtggatgat      120
tattaatccg ggaccggccg cccctccgcc ccgaagtgga aaggctggtg tgcccctcgt      180
tgaccaagaa tctattgcat catcggagaa tatggagctt catcgaatca ccggcagtaa      240
gcgaaggaga atgtgaagcc aggggtgtat agccgtcggc gaaatagcat gccattaacc      300
taggtacaga agtccaattg cttccgatct ggtaaaagat tcacgagata gtaccttctc      360
cgaagtaggt agagcgagta cccggcgcgt aagctcccta attggcccat ccggcatctg      420
tagggcgtcc aaatatcgtg cctctcctgc tttgcccggt gtatgaaacc ggaaaggccg      480
ctcaggagct ggccagcggc gcagaccggg aacacaagct ggcagtcgac ccatccggtg      540
ctctgcactc gacctgctga ggtccctcag tccctggtag gcagctttgc cccgtctgtc      600
cgcccggtgt gtcggcgggg ttgacaaggt cgttgcgtca gtccaacatt tgttgccata      660
ttttcctgct ctccccacca gctgctcttt tcttttctct ttcttttccc atcttcagta      720
tattcatctt cccatccaag aacctttatt tcccctaagt aagtactttg ctacatccat      780
actccatcct tcccatccct tattcctttg aacctttcag ttcgagcttt cccacttcat      840
cgcagcttga ctaacagcta ccccgcttga gcagacatca ccatg                     885

<210> SEQ ID NO 34
<211> LENGTH: 45
```

```
<212> TYPE: DNA
<213> ORGANISM: Artificial sequence
<220> FEATURE:
<223> OTHER INFORMATION: Synthetic nucleic acid

<400> SEQUENCE: 34
aggtcgacgg tatcgatagt ttaaacgtga aagagattga ggatc          45

<210> SEQ ID NO 35
<211> LENGTH: 29
<212> TYPE: DNA
<213> ORGANISM: Artificial sequence
<220> FEATURE:
<223> OTHER INFORMATION: Synthetic nucleic acid

<400> SEQUENCE: 35
gtctgtcaga ccaatagata ccaatgagg                            29

<210> SEQ ID NO 36
<211> LENGTH: 29
<212> TYPE: DNA
<213> ORGANISM: Artificial sequence
<220> FEATURE:
<223> OTHER INFORMATION: Synthetic nucleic acid

<400> SEQUENCE: 36
tatctattgg tctgacagac gggcaattg                            29

<210> SEQ ID NO 37
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 37
cattgcagag gagccgctct tgcatctttg                           30

<210> SEQ ID NO 38
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 38
agagcggctc ctctgcaatg gatggccttc                           30

<210> SEQ ID NO 39
<211> LENGTH: 43
<212> TYPE: DNA
<213> ORGANISM: Artificial sequence
<220> FEATURE:
<223> OTHER INFORMATION: Synthetic nucleic acid

<400> SEQUENCE: 39 gatccccgg gctgcagttt aaacgtggcg aggtgaacat ctc             43

<210> SEQ ID NO 40
<211> LENGTH: 45
<212> TYPE: DNA
<213> ORGANISM: Artificial sequence
<220> FEATURE:
<223> OTHER INFORMATION: Synthetic nucleic acid
```

-continued

<400> SEQUENCE: 40
aggtcgacgg tatcgatagt ttaaaccagt tccaacagtg gagtg                45

<210> SEQ ID NO 41
<211> LENGTH: 29
<212> TYPE: DNA
<213> ORGANISM: Artificial sequence
<220> FEATURE:
<223> OTHER INFORMATION: Synthetic nucleic acid

<400> SEQUENCE: 41
gtctgtcaga ggatacccat cgtgggatg                                  29

<210> SEQ ID NO 42
<211> LENGTH: 29
<212> TYPE: DNA
<213> ORGANISM: Artificial sequence
<220> FEATURE:
<223> OTHER INFORMATION: Synthetic nucleic acid

<400> SEQUENCE: 42
atgggtatcc tctgacagac gggcaattg                                  29

<210> SEQ ID NO 43
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 43
catcccgcac gagccgctct tgcatctttg                                 30

<210> SEQ ID NO 44
<211> LENGTH: 28
<212> TYPE: DNA
<213> ORGANISM: Artificial sequence
<220> FEATURE:
<223> OTHER INFORMATION: Synthetic nucleic acid

<400> SEQUENCE: 44
agagcggctc gtgcgggatg gggtgtga                                   28

<210> SEQ ID NO 45
<211> LENGTH: 44
<212> TYPE: DNA
<213> ORGANISM: Artificial sequence
<220> FEATURE:
<223> OTHER INFORMATION: Synthetic nucleic acid

<400> SEQUENCE: 45 ggatccccg ggctgcagtt taaacactgt cccagaggtc cgtc                  44

<210> SEQ ID NO 46
<211> LENGTH: 44
<212> TYPE: DNA
<213> ORGANISM: Artificial sequence
<220> FEATURE:
<223> OTHER INFORMATION: Synthetic nucleic acid

<400> SEQUENCE: 46
aggtcgacgg tatcgatagt ttaaacggta atctcggaat tcgc                 44

<210> SEQ ID NO 47

```
<211> LENGTH: 29
<212> TYPE: DNA
<213> ORGANISM: Artificial sequence
<220> FEATURE:
<223> OTHER INFORMATION: Synthetic nucleic acid

<400> SEQUENCE: 47
gtctgtcaga aggaggacat tgtgagtag                                    29

<210> SEQ ID NO 48
<211> LENGTH: 29
<212> TYPE: DNA
<213> ORGANISM: Artificial sequence
<220> FEATURE:
<223> OTHER INFORMATION: Synthetic nucleic acid

<400> SEQUENCE: 48
atgtcctcct tctgacagac gggcaattg                                    29

<210> SEQ ID NO 49
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 49
tgaaccagac gagccgctct tgcatctttg                                   30

<210> SEQ ID NO 50
<211> LENGTH: 31
<212> TYPE: DNA
<213> ORGANISM: Artificial sequence
<220> FEATURE:
<223> OTHER INFORMATION: Synthetic nucleic acid

<400> SEQUENCE: 50
agagcggctc gtctggttca agtgaagctt g                                 31

<210> SEQ ID NO 51
<211> LENGTH: 45
<212> TYPE: DNA
<213> ORGANISM: Artificial sequence
<220> FEATURE:
<223> OTHER INFORMATION: Synthetic nucleic acid

<400> SEQUENCE: 51 ggatccccccg ggctgcagtt taaacctcct cgagagctgg agaac                 45

<210> SEQ ID NO 52
<211> LENGTH: 44
<212> TYPE: DNA
<213> ORGANISM: Artificial sequence
<220> FEATURE:
<223> OTHER INFORMATION: Synthetic nucleic acid

<400> SEQUENCE: 52
aggtcgacgg tatcgatagt ttaaacgcac gacacaacac agtc                   44

<210> SEQ ID NO 53
<211> LENGTH: 30
<212> TYPE: DNA
<213> ORGANISM: Artificial sequence
<220> FEATURE:
<223> OTHER INFORMATION: Synthetic nucleic acid
```

```
<400> SEQUENCE: 53
gtctgtcaga tcgacggcat gttcaagttg                              30

<210> SEQ ID NO 54
<211> LENGTH: 29
<212> TYPE: DNA
<213> ORGANISM: Artificial sequence
<220> FEATURE:
<223> OTHER INFORMATION: Synthetic nucleic acid

<400> SEQUENCE: 54
atgccgtcga tctgacagac gggcaattg                               29

<210> SEQ ID NO 55
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 55
aacgcaccag gagccgctct tgcatctttg                              30

<210> SEQ ID NO 56
<211> LENGTH: 28
<212> TYPE: DNA
<213> ORGANISM: Artificial sequence
<220> FEATURE:
<223> OTHER INFORMATION: Synthetic nucleic acid

<400> SEQUENCE: 56
agagcggctc ctggtgcgtt gatggagc                                28

<210> SEQ ID NO 57
<211> LENGTH: 45
<212> TYPE: DNA
<213> ORGANISM: Artificial sequence
<220> FEATURE:
<223> OTHER INFORMATION: Synthetic nucleic acid

<400> SEQUENCE: 57
gatccccggg gctgcagttt aaacctcttg actatcgcgt atcac             45

<210> SEQ ID NO 58
<211> LENGTH: 45
<212> TYPE: DNA
<213> ORGANISM: Artificial sequence
<220> FEATURE:
<223> OTHER INFORMATION: Synthetic nucleic acid

<400> SEQUENCE: 58
aggtcgacgg tatcgatagt ttaaacagac gcattgctgt tctac             45

<210> SEQ ID NO 59
<211> LENGTH: 28
<212> TYPE: DNA
<213> ORGANISM: Artificial sequence
<220> FEATURE:
<223> OTHER INFORMATION: Synthetic nucleic acid

<400> SEQUENCE: 59
gtctgtcaga tcgtgctcgt ctctcgtc                                28

<210> SEQ ID NO 60
```

```
<211> LENGTH: 29
<212> TYPE: DNA
<213> ORGANISM: Artificial sequence
<220> FEATURE:
<223> OTHER INFORMATION: Synthetic nucleic acid

<400> SEQUENCE: 60
acgagcacga tctgacagac gggcaattg                                   29

<210> SEQ ID NO 61
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 61
caacatgctc gagccgctct tgcatctttg                                  30

<210> SEQ ID NO 62
<211> LENGTH: 28
<212> TYPE: DNA
<213> ORGANISM: Artificial sequence
<220> FEATURE:
<223> OTHER INFORMATION: Synthetic nucleic acid

<400> SEQUENCE: 62
agagcggctc gagcatgttg aatgttgc                                    28

<210> SEQ ID NO 63
<211> LENGTH: 44
<212> TYPE: DNA
<213> ORGANISM: Artificial sequence
<220> FEATURE:
<223> OTHER INFORMATION: Synthetic nucleic acid

<400> SEQUENCE: 63
ggatcccccg ggctgcagtt taaacaagtc ctcgacatgg tctg                  44

<210> SEQ ID NO 64
<211> LENGTH: 45
<212> TYPE: DNA
<213> ORGANISM: Artificial sequence
<220> FEATURE:
<223> OTHER INFORMATION: Synthetic nucleic acid

<400> SEQUENCE: 64
ggtcgacggt atcgatagtt taaaccctgg tgatcttgta agcag                 45

<210> SEQ ID NO 65
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 65
gtctgtcaga gggagatcat ggtctggatg                                  30

<210> SEQ ID NO 66
<211> LENGTH: 29
<212> TYPE: DNA
<213> ORGANISM: Artificial sequence
<220> FEATURE:
<223> OTHER INFORMATION: Synthetic nucleic acid
```

<400> SEQUENCE: 66
atgatctccc tctgacagac gggcaattg                               29

<210> SEQ ID NO 67
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 67
tccccgatgg gagccgctct tgcatctttg                              30

<210> SEQ ID NO 68
<211> LENGTH: 29
<212> TYPE: DNA
<213> ORGANISM: Artificial sequence
<220> FEATURE:
<223> OTHER INFORMATION: Synthetic nucleic acid

<400> SEQUENCE: 68
agagcggctc ccatcgggga tggcctaag                               29

<210> SEQ ID NO 69
<211> LENGTH: 43
<212> TYPE: DNA
<213> ORGANISM: Artificial sequence
<220> FEATURE:
<223> OTHER INFORMATION: Synthetic nucleic acid

<400> SEQUENCE: 69 ggatccccg ggctgcagtt taaactccac acgactgtcg aag                43

<210> SEQ ID NO 70
<211> LENGTH: 44
<212> TYPE: DNA
<213> ORGANISM: Artificial sequence
<220> FEATURE:
<223> OTHER INFORMATION: Synthetic nucleic acid

<400> SEQUENCE: 70
aggtcgacgg tatcgatagt ttaaacgcga gagactagtc gttg              44

<210> SEQ ID NO 71
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 71
gtgatgccat tacacggtag                                         20

<210> SEQ ID NO 72
<211> LENGTH: 39
<212> TYPE: DNA
<213> ORGANISM: Artificial sequence
<220> FEATURE:
<223> OTHER INFORMATION: Synthetic nucleic acid

<400> SEQUENCE: 72
ctaccgtgta atggcatcac tctgacagac gggcaattg                    39

<210> SEQ ID NO 73

```
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 73
cggcagtcct gagccgctct tgcatctttg                                      30

<210> SEQ ID NO 74
<211> LENGTH: 29
<212> TYPE: DNA
<213> ORGANISM: Artificial sequence
<220> FEATURE:
<223> OTHER INFORMATION: Synthetic nucleic acid

<400> SEQUENCE: 74
agagcggctc aggactgccg gagttgttg                                       29

<210> SEQ ID NO 75
<211> LENGTH: 43
<212> TYPE: DNA
<213> ORGANISM: Artificial sequence
<220> FEATURE:
<223> OTHER INFORMATION: Synthetic nucleic acid

<400> SEQUENCE: 75 ggatccccg ggctgcagtt taaacctcat ccaacgcaac ggc                        43

<210> SEQ ID NO 76
<211> LENGTH: 44
<212> TYPE: DNA
<213> ORGANISM: Artificial sequence
<220> FEATURE:
<223> OTHER INFORMATION: Synthetic nucleic acid

<400> SEQUENCE: 76
aggtcgacgg tatcgatagt ttaaacccgg gtattagatg tgcg                      44

<210> SEQ ID NO 77
<211> LENGTH: 28
<212> TYPE: DNA
<213> ORGANISM: Artificial sequence
<220> FEATURE:
<223> OTHER INFORMATION: Synthetic nucleic acid

<400> SEQUENCE: 77
gtctgtcaga ctgtggacat tgtgcggg                                        28

<210> SEQ ID NO 78
<211> LENGTH: 29
<212> TYPE: DNA
<213> ORGANISM: Artificial sequence
<220> FEATURE:
<223> OTHER INFORMATION: Synthetic nucleic acid

<400> SEQUENCE: 78
atgtccacag tctgacagac gggcaattg                                       29

<210> SEQ ID NO 79
<211> LENGTH: 30
<212> TYPE: DNA
<213> ORGANISM: Artificial sequence
<220> FEATURE:
<223> OTHER INFORMATION: Synthetic nucleic acid
```

-continued

```
<400> SEQUENCE: 79
ggacatggaa gagccgctct tgcatctttg                                          30

<210> SEQ ID NO 80
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 80
agagcggctc ttccatgtcc atctatcatg                                          30

<210> SEQ ID NO 81
<211> LENGTH: 43
<212> TYPE: DNA
<213> ORGANISM: Artificial sequence
<220> FEATURE:
<223> OTHER INFORMATION: Synthetic nucleic acid

<400> SEQUENCE: 81 ggatccccccg ggctgcagtt taaacggttc atgacaatgg atg                          43

<210> SEQ ID NO 82
<211> LENGTH: 41
<212> TYPE: DNA
<213> ORGANISM: Artificial sequence
<220> FEATURE:
<223> OTHER INFORMATION: Synthetic nucleic acid

<400> SEQUENCE: 82
cgaggtcgac ggtatcgata gtttaaacgt tgacctagct g                             41

<210> SEQ ID NO 83
<211> LENGTH: 28
<212> TYPE: DNA
<213> ORGANISM: Artificial sequence
<220> FEATURE:
<223> OTHER INFORMATION: Synthetic nucleic acid

<400> SEQUENCE: 83
ctctcgtcat ggtgatgtct gctcaagc                                            28

<210> SEQ ID NO 84
<211> LENGTH: 28
<212> TYPE: DNA
<213> ORGANISM: Artificial sequence
<220> FEATURE:
<223> OTHER INFORMATION: Synthetic nucleic acid

<400> SEQUENCE: 84
agacatcacc atgacgagag acgagcac                                            28

<210> SEQ ID NO 85
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 85
ggcatctact tcagtagccg taaacagaag                                          30

<210> SEQ ID NO 86
```

```
<211> LENGTH: 28
<212> TYPE: DNA
<213> ORGANISM: Artificial sequence
<220> FEATURE:
<223> OTHER INFORMATION: Synthetic nucleic acid

<400> SEQUENCE: 86
cggctactga agtagatgcc gaccgcgg                                        28

<210> SEQ ID NO 87
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 87
gtctgtcaga tcgagtggag atgtggagtg                                      30

<210> SEQ ID NO 88
<211> LENGTH: 29
<212> TYPE: DNA
<213> ORGANISM: Artificial sequence
<220> FEATURE:
<223> OTHER INFORMATION: Synthetic nucleic acid

<400> SEQUENCE: 88
ctccactcga tctgacagac gggcaattg                                       29

<210> SEQ ID NO 89
<211> LENGTH: 44
<212> TYPE: DNA
<213> ORGANISM: Artificial sequence
<220> FEATURE:
<223> OTHER INFORMATION: Synthetic nucleic acid

<400> SEQUENCE: 89
agtggatccc ccgggctgca gtttaaacga gccgctcttg catc                      44
```